US008642257B2

(12) United States Patent
Szalay et al.

(10) Patent No.: US 8,642,257 B2
(45) Date of Patent: Feb. 4, 2014

(54) VACCINIA VIRUS FOR DIAGNOSIS AND THERAPY OF TUMORS

(75) Inventors: Aladar A. Szalay, Highland, CA (US); Yong A. Yu, San Diego, CA (US); Shahrokh Shabahang, Redland, CA (US); Tatyana Timiryasova, Scotrun, PA (US)

(73) Assignee: Genelux Corporation, San Diego, CA (US)

( * ) Notice: Subject to any disclaimer, the term of this patent is extended or adjusted under 35 U.S.C. 154(b) by 432 days.

(21) Appl. No.: 10/485,179

(22) PCT Filed: Jul. 31, 2002

(86) PCT No.: PCT/IB02/04767
§ 371 (c)(1),
(2), (4) Date: Nov. 5, 2004

(87) PCT Pub. No.: WO03/014380
PCT Pub. Date: Feb. 20, 2003

(65) Prior Publication Data
US 2005/0069491 A1    Mar. 31, 2005

(30) Foreign Application Priority Data

Jul. 31, 2001 (EP) .................................... 01118417
Oct. 30, 2001 (EP) .................................... 01125911

(51) Int. Cl.
C12Q 1/70 (2006.01)
C12Q 1/68 (2006.01)
C12Q 1/66 (2006.01)
A61B 5/055 (2006.01)
A61K 48/00 (2006.01)

(52) U.S. Cl.
USPC ............ 435/5; 435/6.14; 435/6.18; 435/6.19; 435/8; 424/9.3; 424/93.2

(58) Field of Classification Search
USPC .................. 435/4, 5, 6.1, 6.14, 6.18, 6.19, 8; 424/9.3, 93.2
See application file for complete search history.

(56) References Cited

U.S. PATENT DOCUMENTS

| | | | |
|---|---|---|---|
| 4,216,226 A * | 8/1980 | Fukuyasu et al. ............. 514/546 |
| 4,315,914 A * | 2/1982 | Arakawa et al. ............ 424/281.1 |
| 4,442,203 A | 4/1984 | Varshavsky ........................ 435/6 |
| 4,603,112 A | 7/1986 | Paoletti et al. ............. 435/235.1 |
| 4,722,848 A | 2/1988 | Paoletti et al. ............. 424/199.1 |
| 4,769,330 A | 9/1988 | Paoletti et al. ................. 435/436 |
| 4,778,759 A | 10/1988 | Szalay et al. ................... 435/477 |
| 5,110,587 A | 5/1992 | Paoletti et al. ............. 435/235.1 |
| 5,155,020 A | 10/1992 | Paoletti ........................ 435/69.1 |
| 5,221,623 A | 6/1993 | Legocki et al. ............. 435/252.3 |
| 5,283,187 A | 2/1994 | Aebischer et al. ............. 435/182 |
| 5,300,436 A | 4/1994 | Goldstein et al. ............. 435/190 |
| 5,364,773 A | 11/1994 | Paoletti et al. ................. 435/69.1 |
| 5,368,855 A | 11/1994 | Boyle et al. ................. 435/320.1 |
| 5,378,457 A | 1/1995 | Paoletti et al. ............. 424/205.1 |
| 5,550,050 A | 8/1996 | Holland et al. ................. 435/382 |
| 5,639,275 A | 6/1997 | Baetge et al. ............. 604/891.1 |
| 5,646,298 A | 7/1997 | Powell et al. ................. 548/427 |
| 5,650,135 A | 7/1997 | Contag et al. ................. 424/9.1 |
| 5,650,148 A | 7/1997 | Gage et al. ................. 424/93.2 |
| 5,653,975 A | 8/1997 | Baetge et al. ................. 424/93.1 |
| 5,656,481 A | 8/1997 | Baetge et al. ................. 435/325 |
| 5,676,943 A | 10/1997 | Baetge et al. ............. 424/93.21 |
| 5,693,533 A | 12/1997 | Raney et al. ................. 435/366 |
| 5,704,910 A | 1/1998 | Humes ........................ 604/502 |
| 5,710,137 A | 1/1998 | Fisher ............................. 514/44 |
| 5,718,902 A | 2/1998 | Yilma et al. ................. 424/211.1 |
| 5,750,103 A | 5/1998 | Cherksey ................. 424/93.21 |
| 5,756,455 A | 5/1998 | Kinzler et al. ................. 514/12 |
| 5,762,959 A | 6/1998 | Soon-Shiong et al. ........ 424/451 |
| 5,795,790 A | 8/1998 | Schinstine et al. ............. 435/382 |
| 5,798,113 A | 8/1998 | Dionne et al. ................. 424/422 |
| 5,800,828 A | 9/1998 | Dionne et al. ................. 424/422 |
| 5,800,829 A | 9/1998 | Dionne et al. ................. 424/422 |
| 5,830,702 A | 11/1998 | Portnoy et al. ................. 435/69.3 |
| 5,833,975 A | 11/1998 | Paoletti et al. ................. 424/93.2 |
| 5,833,979 A | 11/1998 | Schinstine et al. .......... 424/93.21 |
| 5,834,001 A | 11/1998 | Dionne et al. ................. 424/422 |
| 5,837,234 A | 11/1998 | Gentile et al. ................. 424/93.7 |
| 5,840,576 A | 11/1998 | Schinstine et al. ............. 435/325 |
| 5,842,431 A | 12/1998 | Wu .............................. 112/232 |
| 5,853,385 A | 12/1998 | Emerich et al. ................. 604/500 |
| 5,853,717 A | 12/1998 | Schinstine et al. .......... 424/93.21 |

(Continued)

FOREIGN PATENT DOCUMENTS

AU     709336       9/1994
EP     0 037 441 A1   10/1981

(Continued)

OTHER PUBLICATIONS

Rehemtulla et al, Neoplasia. 2000; 2(6):491-5.*
Chernajovsky et al BMJ. 2006; 332(7534): 170-2.*
Kim et al Gene Ther. 2000; 7(10): 815-6.*
Pfeifer and Verma 2001, Annual Review of Genomics and Human Genetics.2: 177-211.*
Gura Science, 1997, 278: 1041-1042.*
Kelland et al European Journal of Cancer, 2004, 40, 827-836.*
Kerbel et al Cancer Biology & Therapy 2: 4 suppl. 1, S134-139.*
Rubanyi et al Molecular Aspects of Medicine, 2001, 22, 113-142.*
Gautam et al Am J Respir Med, 2002;1(1):35-46.*
McCluskie et al (1999) Mol. Med. 5:287-300.*
Puhlmann et al Cancer Gene Ther. 2000; 7(1): 66-73.*

(Continued)

*Primary Examiner* — Anoop Singh
(74) *Attorney, Agent, or Firm* — McKenna Long & Aldridge, LLP; Stephanie Seidman

(57) ABSTRACT

Described are diagnostic and pharmaceutical compositions comprising a microorganism or cell containing a DNA sequence encoding a detectable protein or a protein capable of inducing a detectable signal, e.g. a luminescent or fluorescent protein, and, in a particular embodiment, furthermore (a) DNA sequence(s) encoding (a) protein(s) suitable for tumor therapy and/or elimination of metastatic tumors, e.g. a cytotoxic or cytostatic protein.

17 Claims, 11 Drawing Sheets

(56) References Cited

U.S. PATENT DOCUMENTS

| | | | | |
|---|---|---|---|---|
| 5,861,290 | A | 1/1999 | Goldsmith et al. | 435/456 |
| 5,866,131 | A | 2/1999 | Ramshaw et al. | 424/186.1 |
| 5,976,796 | A | 11/1999 | Szalay et al. | 435/6 |
| 6,007,806 | A | 12/1999 | Lathe et al. | 424/93.2 |
| 6,025,155 | A | 2/2000 | Hadlaczky et al. | 435/69.1 |
| 6,045,802 | A | 4/2000 | Schlom et al. | 424/199.1 |
| 6,077,697 | A | 6/2000 | Hadlaczky et al. | 435/172.3 |
| 6,080,849 | A | 6/2000 | Bermudes et al. | 536/23.7 |
| 6,093,700 | A | 7/2000 | Mastrangelo et al. | 514/44 |
| 6,099,848 | A | 8/2000 | Frankel et al. | |
| 6,150,170 | A | 11/2000 | Powell et al. | 435/455 |
| 6,190,657 | B1 | 2/2001 | Pawelek et al. | 424/93.1 |
| 6,217,847 | B1 | 4/2001 | Contag et al. | 424/9.1 |
| 6,232,523 | B1 | 5/2001 | Tan et al. | 800/10 |
| 6,235,967 | B1 | 5/2001 | Tan et al. | 800/10 |
| 6,235,968 | B1 | 5/2001 | Tan et al. | 800/10 |
| 6,251,384 | B1 | 6/2001 | Tan et al. | 424/93.21 |
| 6,265,189 | B1 | 7/2001 | Paoletti et al. | 435/70.1 |
| 6,265,557 | B1 | 7/2001 | Diamond et al. | 536/23.1 |
| 6,359,189 | B1 | 3/2002 | Fleischmann | 602/41 |
| 6,416,754 | B1 | 7/2002 | Brown et al. | 424/93.21 |
| 6,428,968 | B1 | 8/2002 | Molnar-Kimber et al. | 435/7.23 |
| 6,455,673 | B1 | 9/2002 | Collier | 530/350 |
| 6,491,905 | B1 | 12/2002 | Sorscher et al. | 435/325 |
| 6,503,703 | B1 | 1/2003 | Palese et al. | 435/5 |
| 6,511,967 | B1 | 1/2003 | Weissleder et al. | 514/44 |
| 6,537,594 | B1 | 3/2003 | Paoletti et al. | 424/93.2 |
| 6,548,068 | B1 | 4/2003 | Schlom et al. | 424/199.1 |
| 6,589,531 | B1 | 7/2003 | Andino-Pavlovsky et al. | |
| 6,596,279 | B1 | 7/2003 | Paoletti et al. | 424/199.1 |
| 6,627,190 | B2 | 9/2003 | Wold et al. | 424/93.2 |
| 6,649,143 | B1 | 11/2003 | Contag et al. | 424/9.1 |
| 6,649,159 | B2 | 11/2003 | Yang et al. | 424/93.21 |
| 6,652,849 | B2 | 11/2003 | Brown et al. | 424/93.2 |
| 6,685,935 | B1 | 2/2004 | Pawelek et al. | 424/93.2 |
| 6,713,293 | B1 | 3/2004 | Grummt et al. | 435/182 |
| 6,743,967 | B2 | 6/2004 | Hadlaczky et al. | 800/25 |
| 6,759,038 | B2 | 7/2004 | Tan et al. | 424/93.21 |
| 6,884,414 | B1 | 4/2005 | Palese et al. | 424/93.2 |
| 6,916,462 | B2 | 7/2005 | Contag et al. | 424/9.6 |
| 6,984,374 | B2 | 1/2006 | Szalay et al. | |
| 7,045,313 | B1 | 5/2006 | Moss et al. | 435/69.1 |
| 7,588,767 | B2 | 9/2009 | Szalay et al. | 424/199 |
| 7,588,771 | B2 | 9/2009 | Szalay et al. | 424/232 |
| 7,662,398 | B2 | 2/2010 | Szalay et al. | 424/232.1 |
| 7,754,221 | B2 | 7/2010 | Szalay et al. | 424/199.1 |
| 8,021,662 | B2 | 9/2011 | Szalay et al. | 424/138.1 |
| 8,052,968 | B2 | 11/2011 | Chen et al. | 424/199.1 |
| 8,066,984 | B2 | 11/2011 | Szalay et al. | 424/93.21 |
| 8,221,769 | B2 | 7/2012 | Szalay et al. | 424/232.1 |
| 8,323,959 | B2 | 12/2012 | Szalay et al. | 435/320.1 |
| 8,357,486 | B2 | 1/2013 | Stritzker et al. | 435/4 |
| 2001/0008025 | A1 | 7/2001 | Hadlaczky et al. | 800/8 |
| 2001/0029023 | A1 | 10/2001 | Szalay et al. | 435/7.1 |
| 2002/0054865 | A1 | 5/2002 | Fujimori et al. | 424/93.21 |
| 2002/0160410 | A1 | 10/2002 | Hadlaczky et al. | 435/6 |
| 2002/0160970 | A1 | 10/2002 | Hadlaczky et al. | 514/44 |
| 2003/0009015 | A1 | 1/2003 | Ulrich et al. | 536/23.1 |
| 2003/0031628 | A1 | 2/2003 | Zhao et al. | 424/9.6 |
| 2003/0031681 | A1 | 2/2003 | Mc Cart et al. | 424/186.1 |
| 2003/0033617 | A1 | 2/2003 | Hadlaczky et al. | 800/6 |
| 2003/0044384 | A1 | 3/2003 | Roberts et al. | 424/93.2 |
| 2003/0059400 | A1 | 3/2003 | Szalay | 424/93.2 |
| 2003/0083293 | A1 | 5/2003 | Hadlaczky et al. | 514/44 |
| 2003/0086906 | A1 | 5/2003 | Mastrangelo et al. | 424/93.2 |
| 2003/0101480 | A1 | 5/2003 | Hadlaczky et al. | 800/278 |
| 2003/0133949 | A1 | 7/2003 | Szalay et al. | 424/200.1 |
| 2003/0161788 | A1 | 8/2003 | Zhao et al. | 424/9.6 |
| 2003/0165465 | A1 | 9/2003 | Roberts et al. | 424/93.2 |
| 2003/0165477 | A1 | 9/2003 | Balloul et al. | 424/93.21 |
| 2003/0198627 | A1 | 10/2003 | Arts et al. | 424/93.21 |
| 2003/0213007 | A1 | 11/2003 | Slattery et al. | 800/15 |
| 2003/0228261 | A1 | 12/2003 | Szalay et al. | 424/9.34 |
| 2003/0228330 | A1 | 12/2003 | Falkner et al. | 424/232.1 |
| 2004/0076622 | A1 | 4/2004 | Studeny et al. | 424/93.21 |
| 2004/0091995 | A1 | 5/2004 | Schlom et al. | 435/235.1 |
| 2004/0143861 | A1 | 7/2004 | Hadlaczky et al. | 800/14 |
| 2004/0213741 | A1 | 10/2004 | Szalay et al. | 424/9.6 |
| 2004/0234455 | A1 | 11/2004 | Szalay et al. | 424/9.6 |
| 2005/0025745 | A1 | 2/2005 | Fujimori | |
| 2005/0025747 | A1 | 2/2005 | Laidlaw et al. | 424/93.2 |
| 2005/0031643 | A1 | 2/2005 | Szalay et al. | 424/199.1 |
| 2005/0063993 | A1 | 3/2005 | Schlom et al. | 424/199.1 |
| 2005/0069491 | A1 | 3/2005 | Szalay et al. | 424/1.11 |
| 2005/0249670 | A1 | 11/2005 | Szalay et al. | |
| 2006/0051370 | A1 | 3/2006 | Szalay et al. | |
| 2006/0099224 | A1 | 5/2006 | Kirn | 424/199.1 |
| 2006/0147420 | A1 | 7/2006 | Fueyo et al. | 424/93.2 |
| 2007/0025981 | A1 | 2/2007 | Szalay et al. | 424/130.1 |
| 2007/0202572 | A1 | 8/2007 | Szalay et al. | 435/69.1 |
| 2007/0212727 | A1 | 9/2007 | Szalay et al. | 435/6 |
| 2008/0193373 | A1 | 8/2008 | Stritzker et al. | 424/1.17 |
| 2009/0053244 | A1 | 2/2009 | Chen et al. | 424/174.1 |
| 2009/0081639 | A1 | 3/2009 | Hill | 435/5 |
| 2009/0098529 | A1 | 4/2009 | Chen et al. | 435/5 |
| 2009/0117034 | A1 | 5/2009 | Chen et al. | 424/1.17 |
| 2009/0117047 | A1 | 5/2009 | Szalay et al. | 424/9.3 |
| 2009/0117048 | A1 | 5/2009 | Szalay et al. | 424/9.3 |
| 2009/0117049 | A1 | 5/2009 | Szalay et al. | 424/9.3 |
| 2009/0123382 | A1 | 5/2009 | Szalay et al. | 424/9.6 |
| 2009/0136917 | A1 | 5/2009 | Szalay et al. | 435/5 |
| 2009/0155287 | A1 | 6/2009 | Chen et al. | 424/158 |
| 2009/0162288 | A1 | 6/2009 | Chen et al. | 424/9.3 |
| 2009/0175830 | A1 | 7/2009 | Fueyo et al. | 424/93.2 |
| 2009/0180955 | A1 | 7/2009 | Stritzker et al. | 424/1.73 |
| 2009/0180987 | A1 | 7/2009 | Stritzker et al. | 424/93.2 |
| 2009/0311664 | A1 | 12/2009 | Fong et al. | 435/5 |
| 2010/0008946 | A1 | 1/2010 | Szalay et al. | 424/199.1 |
| 2010/0062016 | A1 | 3/2010 | Szalay et al. | 424/199.1 |
| 2010/0196325 | A1 | 8/2010 | Szalay et al. | 424/93.6 |
| 2010/0233078 | A1 | 9/2010 | Szalay et al. | 424/1.17 |
| 2011/0064650 | A1 | 3/2011 | Szalay | 424/1.11 |
| 2011/0293527 | A1 | 12/2011 | Chen et al. | 424/9.3 |
| 2011/0300176 | A1 | 12/2011 | Szalay et al. | 424/199.1 |
| 2012/0276010 | A1 | 11/2012 | Szalay et al. | 424/9.1 |
| 2012/0308484 | A1 | 12/2012 | Szalay et al. | 424/9.3 |
| 2013/0129614 | A9 | 5/2013 | Szalay et al. | 424/1.11 |
| 2013/0130292 | A1 | 5/2013 | Szalay et al. | 435/18 |

FOREIGN PATENT DOCUMENTS

| | | |
|---|---|---|
| EP | 0 037 441 B1 | 5/1984 |
| EP | 0 861 093 | 9/1998 |
| EP | 1020197 | 7/2000 |
| EP | 1 146 125 | 10/2001 |
| EP | 1 281 772 A1 | 2/2003 |
| EP | 1 281 777 A1 | 2/2003 |
| EP | 1 281 767 | 5/2003 |
| EP | 03 013 826.7 | 6/2003 |
| EP | 03735553.4 | 6/2003 |
| EP | 03 018 478.2 | 8/2003 |
| EP | 03 024 283.8 | 10/2003 |
| EP | 1 369 491 | 12/2003 |
| EP | 1 414 994 | 5/2004 |
| EP | 1 254 250 | 3/2005 |
| EP | 1 512 746 | 3/2005 |
| EP | 1 526 185 | 4/2005 |
| JP | 55035004 | 3/1980 |
| JP | 09-502993 | 3/1997 |
| JP | 2002097144 | 4/2002 |
| WO | WO 88/00617 | 1/1988 |
| WO | WO 90/13658 | 11/1990 |
| WO | 91/07989 | 6/1991 |
| WO | WO 92/22327 | 12/1992 |
| WO | WO 93/01296 | 1/1993 |
| WO | 94/10302 | 5/1994 |
| WO | 95/31105 | 11/1995 |
| WO | 96/11279 | 4/1996 |
| WO | WO 96/40238 | 12/1996 |
| WO | 97/18841 | 5/1997 |
| WO | WO 97/35997 | 10/1997 |
| WO | WO 97/40183 | 10/1997 |
| WO | WO 98/14605 | 4/1998 |
| WO | WO 99/13053 | 3/1999 |

(56) References Cited

FOREIGN PATENT DOCUMENTS

| | | |
|---|---|---|
| WO | WO 99/18799 | 4/1999 |
| WO | 99/32646 | 7/1999 |
| WO | 00/47237 | 8/2000 |
| WO | WO 00/62735 | 10/2000 |
| WO | WO 00/73479 | 12/2000 |
| WO | 01/05229 | 1/2001 |
| WO | 01/12234 | 2/2001 |
| WO | 01/14579 | 3/2001 |
| WO | 01/18195 | 3/2001 |
| WO | 01/20989 | 3/2001 |
| WO | 01/24637 | 4/2001 |
| WO | 01/25399 | 4/2001 |
| WO | WO 01/25397 | 4/2001 |
| WO | WO 01/35970 | 5/2001 |
| WO | 01/55444 | 8/2001 |
| WO | 03/006069 | 1/2003 |
| WO | 03/014380 | 2/2003 |
| WO | 03/045153 A1 | 6/2003 |
| WO | PCT/EP03/05907 | 6/2003 |
| WO | WO 03/049117 | 6/2003 |
| WO | 03/057007 | 7/2003 |
| WO | 03/063593 | 8/2003 |
| WO | 03/092600 | 11/2003 |
| WO | 03/102168 A1 | 12/2003 |
| WO | 03/102169 | 12/2003 |
| WO | 03/104485 A2 | 12/2003 |
| WO | WO 2004/030631 | 4/2004 |
| WO | 2004/044175 | 5/2004 |
| WO | 2005/047458 | 5/2005 |
| WO | 2005/057488 | 6/2005 |
| WO | 2005/072622 | 8/2005 |
| WO | WO 2008/100292 | 8/2008 |

OTHER PUBLICATIONS

Timiryasova et al (Bioluminescence & Chemiluminescence, Proceedings of the International Symposium, 11th, Pacific Grove, CA, United States, Sep. 6-10, 2000, Meeting Date 2000, 457-460.*
Lu et al Cancer Gene Ther. Jan.-Feb. 1999; 6(1): 64-72.*
Weng et al Am J Physiol Lung Cell Mol Physiol. 2000; 278(6):L1273-9).*
Contang et al Photochem Photobiol. 1997; 66(4): 523-31.*
Zhang et al Cancer Res. 2007, 67, 10038-10046.*
Gentschev et al Apr. 2009;16(4):320-8.*
"Generation of Recombinant Vaccinia Viruses," Unit 16.17 in *Short Protocols in Molecular Biology 2nd edition: a compendium of Methods from Current Protocols in Molecular Biology*, Green Publishing and Wiley-Interscience Supplement 15:16.71-16.82 (1992).
Adonai et al., "Ex vivo cell labeling with $^{64}$Cu-pyruvaldehyde-bis($N^4$-methylthiosemicarbazone) for imaging cell trafficking in mice with positron-emission tomography," Proc. Natl. Acad. Sci. USA 99: 3030-3035 (2002).
Altschul et al., "Basic local alignment search tool," J Molec Biol 215:403-410 (1990).
Ando, N. and M. Matumoto, "Unmasking of growth of dermovaccinia strain dairen I in L cells by acid treatment of cells after virus adsorption," Japan. J. Microbiol. 14(3): 181-186 (1979).
Antoine et al., "The complete genomic sequence of the modified vaccinia Ankara strain: comparison with other orthopoxviruses," Virology 244: 365-396 (1998).
ATCC Accession No. 59324.
ATCC Accession No. 59325.
ATCC Accession Nos. CCL-121.
ATCC Accession Nos. CRL-12011.
ATCC Accession Nos. CRL-12012.
ATCC catalog No. 700294.
ATCC No. CCL-107.
ATCC No. CRL-6475.
ATCC under Accession No. VR-1549.
Barrett et al., "Yellow Fever Vaccines," Biologicals 25:17-25 (1997).
Bauerschnitz et al., "Treatment of Ovarian Cancer with a Tropism Modified Oncolytic Adenovirus," Cancer Research 62: 1266-1270 (2002).
Benes et al., "M13 and pUC vectors with new unique restriction sites for cloning," Gene 130: 151-152 (1993).
Bernards et al., "Effective tumor immunotherapy directed against an oncogene-encoded produt using a vaccinia virus vector," Proc. Natl. Acad. Sci. USA 84: 6854-6858 (1987).
Beshara et al., "Kinetic analysis of $^{52}$Fe-labelled iron(III) hydroxide-sucrose complex following blous administration using positron emission tomography," Br. J. Haematol. 104: 288-295 (1999).
Beshara et al., "Pharmacokinetics and red cell utilization of iron(III) hydroxide-sucrose complex in anaemic patients: a study using positron emission tomography," Br. J. Haematol. 104: 296-302 (1999).
Bisno et al., "Streptococcal infections of skin and soft tissues," N. Engl. J. Med. 334(4): 240-245 (1996).
Blakemore, "Magnetotactic Bacteria," Annu. Rev. Microbiol. 36: 217-238 (1982).
Broder, C.C. and P.L. Earl, "Recombinant Vaccinia Viruses," Mol. Biotechnol. 13: 223-245 (1999).
Brouqui, P. and D. Raoult, "Endocarditis due to rare and fastidious bacteria," Clinical Microbiology Reviews 14(1): 177-207 (2001).
Calonder et al., "Kinetic modeling of $^{52}$Fe/$^{52m}$Mn-Citrate at the Blood-Brain Barrier by Positron Emission Tomography," J. Neurochem. 73: 2047-2055 (1999).
Carrillo and Lipman et al., "The Multiple Sequence Alignment Problem in Biology," SIAM J Applied Math 48:1073-1082 (1988).
Chakrabarti et al., "Vaccinia virus expression vector: coexpression of β-galactosidase provides visual screening of recombinant virus plaques," Mol. Cell Biol. 5:3403-3409 (1985).
Chakrabarti et al., "Compact, Synthetic, Vaccinia Virus Early/Late Promoter for Protein Expression," BioTechniques 23(6): 1094-1097 (1997).
Chamberlain et al., "Costimulation enhances the active immunotherapy effect of recombinant anticancer vaccines," Cancer Res. 56: 2832-2836 (1996).
Child et al., "Insertional inactivation of the large subunit of ribonucleotide reductase encoded by vaccinia virus is associated with reduced virulence in vivo," Virology 174:625-629 (1990).
Colinas et al., "A DNA ligase gene in the copenhagen strain of vaccinia virus is nonessential for viral replication and recombination," Virology 179: 267-275 (1990).
Cusumano et al., "Synergic activities of streptococcal pyrogenic exotoxin A and lipoteichoic acid in cytokine induction," Microbiologica 23(1): 37-45 (2000).
Davison, A. J. and B. Moss, "Structure of Vaccinia Virus Early Promoters," J. Mol. Biol. 210: 749-769 (1989).
Davison et al., "New vaccinia virus recombination plasmids incorporating a synthetic late promoter for high level expression of foreign proteins," Nucleic Acids Research 18: 4285-4286 (1990).
Devereux, J., et al., "A comprehensive set of sequence analysis programs for the VAX," Nucleic Acids Research 12(1): 387-95 (1984).
Earl et al., "T-Lymphocyte Priming and Protection Against Friend Leukemoa by Vaccinia-Retrovirus *env* Gene Recombinant," Science 234: 728-731 (1986).
Ebert et al., "Oncolytic vesicular stomatitis virus for treatment of orthotopic hepatocellular carcinoma in immune-competent rats," Cancer Research 63: 3605-3611 (2003).
Ebert et al., "Syncytia induction enhances the oncolytic potential of vesicular stomatitis virus in virotherapy for cancer," Cancer Research 64: 3265-3270 (2004).
Estin et al, "Recombinant vaccinia virus vaccine against the human melanoma antigen p97 for use in immunotherapy," Proc. Natl. Acad. Sci. USA 85: 1052-1056 (1988).
Ferretti et al., "Complete genome sequence of an M1 strain of *Streptococcus pyogenes*," Proc. Natl. Acad. Sci. USA 98(8):4658-4663 (2001).
Flexner et al., "Successful vaccination with a polyvalent live vector despite existing immunity to an expressed antigen," Nature 355:259-262 (1988).
Flexner et al., "Characterization of Human Immunodeficiency Virus *gag/pol* Gene Products Expressed by Recombinant Vaccinia Viruses," Virology 166: 339-349 (1988).

(56) References Cited

OTHER PUBLICATIONS

Giedlin et al., "Vesicular stomatitis virus: an exciting new therapeutic oncolytic virus candidate for cancer or just another chapter from *Field's Virology*?" Cancer Cell 4: 241-243 (2003).
Goebel et al., "The complete DNA sequence of vaccinia virus," Virology 179:247-266 (1990).
Goebel et al., "Appendix to 'The complete DNA Sequence of Vaccinia Virus,'" Virology 179: 517-563 (1990).
Green et al., "Necrotizing Fasciitis," Chest 110(1):219-229 (1996).
Greinwald et al., "Treatment of lymphangiomas in children: an update of Picibanil (Ok-432) sclerotherapy," Otolaryngol Head Neck Surg 121(4): 381-387 (1999).
Gribskov et al., "Sigma factors from *E. coli*, *B. subtilis*, phage SP01, and phage T4 are homologous proteins," Nucl. Acids Res. 14:6745-6763 (1986).
Huang et al., "Oncolysis of hepatic metastasis of colorectal cancer by recombinant vesticular stomatitis virus in immune-competent mice," Mol. Ther. 8(3): 434-440 (2003).
Hurst et al., "A novel model of a metastatic human breast tumour xenograft line," Br. J. Cancer 68: 274-276 (1993).
Isaacs et al., "Vaccinia virus complement-control protein prevents antibody-dependent complement-enhanced neutralization of infectivity and contributes to virulence," Proc Natl Acad Sci U S A. 89:628-632 (1992).
Johnson et al., "An update on the vaccinia virus genome," Virology 196: 381-401 (1993).
Kantor et al., "Antitumor Activity and Immune Responses Induced by a Recombinant Carcinoembryonic Antigen-Vaccinia Virus Vaccine," J. Natl. Cancer Inst. 84: 1084-1091 (1992).
Katz et al., "Mutations in the vaccinia virus A33R and B5R envelope proteins that enhance release of extracellular virions and eliminate formation of actin-containing microvilli without preventing tyrosine phosphorylation of the A36R protein," J. Virology 77:12266-12275 (2003).
Kotwal et al., "Mapping and Insertional Mutagenesis of a Vaccinia Virus Gene Encoding a 13, 800-Da Secreted Protein," Virology 171:579-587 (1989).
Kozak, M., "Structural features in Eukaryotic mRNAs that modulate the Initiation of Translation," J. Biol. Chem. 266:19867-19870 (1991).
Lamberton et al., "Construction and characterization of a bioluminescent *Streptococcus pyogene*, Proceedings of the 12th International Symposium on Bioluminescence and Chemiluminescence" Progress & Current Appications, Stanley, P.E. and L.J. Kricka et al (Eds). World Scientific Publishing Co. Pte. Ltd., pp. 85-88 (2002).
Lamberton et al., "Generation and characterization of a bioluminescent *Streptococcus pyogenes*," Proceedings of the 12th International Symposium on Bioluminescence & Chemiluminescence: Apr. 5-9, 2002, Robinson College, University of Cambridge, UK, p. 3.22 (2002).
Lathe et al., "Tumour prevention and rejection with recombinant vaccinia," Nature (London) 326: 878-880 (1987).
Lee et al. "Prodrug and antedrug: two diametrical approaches in designing safer drugs," Arch. Pharm. Res. 25(2): 111-136 (2002).
Lee et al., "Molecular attenuation of vaccinia virus: mutant generation and animal characterization," Journal of Virology 66:2617-2630 (1992).
Leenders et al., "Blood to brain iron uptake in one Rhesus monkey using [Fe-52]-citrate and positron emission tomography (PET): influence of haloperidol," J. Neural.Transm.Suppl. 43: 123-132 (1994).
Lemmon et al., "Anaerobic bacteria as a gene delivery system that is controlled by the tumor microenvironment," Gene Therapy 4: 791-796 (1997).
Lemmon et al., "Anaerobic bacteria as a gene delivery system to tumors," Proceedings of the 85th Annual Meeting of the American Association for Cancer Research, San Francisco, CA Apr. 10-13, 1994, published in: Proc. Am. Cancer Research Assn 35: 374 (1994).
Lewis et al., "Comparison of Four $^{64}$Cu-Labeled Somatostatin Analogues in Vitro and in a Tumor-Bearing Rat Model: Evaluation of New Derivatives for Positron Emission Tomography Imaging and Targeted Radiotherapy," J. Med. Chem. 42: 1341-1347 (1999).
Li et al., "*Bifidobacterium adolescentis* as a delivery system of endostatin for cancer gene therapy: Selective Inhibitor of angiogenesis and hypoxic tumor growth," Cancer Gene Therapy 10: 105-111 (2003).
Liau et al., "Treatment of intracranial gliomas with bone marrow-derived dendritic cells pulsed with tumor antigens," J. Neurosurg. 90(6): 1115-1124 (1999).
Liu et al., "An E1B-19 kDa gene deletion mutant adenovirus demonstrates tumor necrosis factor-enhanced cancer selectivity and enhanced oncolytic potency," Molecular Therapy 9(6): 786-803 (2004).
Lopez et al., "Infections in children with malignant disease in Argentina," Cancer 47(5): 1023-1030 (1981).
Mayford et al., "CaMKII Regulates the Frequency-Response Function of Hippocampal Synapses for the Production of Both LTD and LTP," Cell 81: 891-904 (1995).
Mayr et al., "The Smallpox Vaccination Strain MVA: Marker, Genetic Structure, Experience Gained with the Parenteral Vaccination and Behavior in Organisms with a Debilitated Defense Mechanism," Zentbl. Bakteriol. Hyg. Abt 1 Orig. B 167: 375-390 (1978) [In German, English abstract on first page of article].
McAllister et al., "Recombinant yellow fever viruses are effective therapeutic vaccines for treatment of murine experimental solid tumors and pulmonary metastases," J. Virol. 74:9197-9205 (2000).
McAneny et al., "Results of a Phase I trial of a recombinant vaccinia virus that expresses carcinoembryonic antigen in patients with advanced colorectal cancer,"Ann. Surg. Oncol. 3(5): 495-500 (1996).
Mikryukov et al., "Structural-functional organization of segment of vaccinia virus genome," Soviet Biotechnology (Biotekhnologiya) 4: 19-25 (1988) [corresponds to pp. 442-449 in the Russian language edition].
Moore et al., "Steroid hormone synthesis by a vaccinia enzyme: a new type of virus virulence factor," EMBO J. 1992 11:1973-1980, corrigendum in The EMBO Journal 11(9): 3490 (1992).
Moss, B., "Genetically engineered poxviruses for recombinant gene expression, vaccination, and safety," Proc. Natl. Acad. Sci. USA 93: 11341-11348 (1996).
Moss, B., "Poxvirus vectors: cytoplasmic expression of transferred genes," Curr. Opin. Genet. Dev. 3: 86-90 (1993).
Mullen et al., "Viral Oncolysis," The Oncologist 7: 106-119 (2002).
Mulryan et al., "Attenuated recombinant vaccinia virus expressing oncofetal antigen (tumor-associated antigen) 5T4 induces active therapy of established tumors," Mol Cancer Ther 1(12): 1129-1137 (2002).
Munagala et al., "The purine nucleoside phosphorylase from *Trichomonas vaginalis* is a homologue of the bacterial enzyme," Biochemistry 41(33): 10382-10389 (2002).
NCBI Protein AAA48282.
NCBI Nucleotide AF012825.
NCBI Nucleotide. AF095689.
NCBI Nucleotide AF380138.
NCBI Nucleotide AX003206.
NCBI Nucleotide. AY009089.
NCBI Nucleotide AY243312.
NCBI Nucleotide AY484669.
NCBI Nucleotide AY603355.
NCBI Nucleotide M35027.
NCBI Nucleotide M57977.
NCBI Nucleotide U94848.
NCBI Nucleotide X69198.
NCBI Nucleotide X94355.
Needleman et al., "A general method applicable to the search for similarities in the amino acid sequences of two proteins," J. Mol. Biol. 48:443-453 (1970).
Nogrady, T., *Medicinal Chemistry A Biochemical Approach*, New York: Oxford University Press, pp. 388-392 (1985).
Oertli et al., "Non-replicating recombinant vaccinia virus encoding murine B-7 molecules effective costimulation of naive CD4+ splenocytes in vitro," J. Gen. Virol. 77: 3121-3125 (1996).

(56) References Cited

OTHER PUBLICATIONS

Okamoto et al., "Severe impairment of anti-cancer effect of lipoteichoic acid-relatedmolecule isolated from a penicillin-killed *Streptococcus pyogenes* in toll-like receptor 4-deficient mice," International Immunopharmacology 1(9-10): 1789-1795 (2001).
Patel et al., "A poxvirus-derived vector that directs high levels of expression of cloned genes in mammalian cells," Proc. Natl. Acad. Sci. USA 85: 9431-9435 (1988).
Pawelek et al., "Tumor-targeted *Salmonella* as a Novel Anticancer Vector," Cancer Therapy 57: 4537-4544 (1997).
Pearson et al., "Improved tools for biological sequence comparison," Proc. Natl. Acad. Sci. USA 85:2444-2448 (1988).
Pilcher, H., "GM Bug activates cancer drug: Bacteria targets medicine to shrivel mouse tumours," news @ nature.com, Published online: Apr. 22, 2004; http://www.nature.com/news/2004/040419/full/040419-9.html, (accessed on Nov. 18, 2004).
Pinkert et al., "An albumin enhancer located 10 kb upstream functions along with its promoter to direct efficient, liver-specific expression in transgenic mice," Genes & Dev. 1: 268-76 (1987).
Pluciennczak et al., "Nucelotide sequence of a cluster and late genes in a conserved segment of the vaccinia virus genome," Nucleic Acids Research 13(3): 993-998 (1985).
Puhlmann et al., "Vaccinia virus as a vector for tumor-directed gene therapy: biodistribution of a thymidine kinase-deleted mutant," Cancer Gene Therapy 7(1): 66-73 (2000).
Qin, H. and S.K. Chatterjee, "Cancer gene therapy using tumor cells infected with recombinant vaccinia virus expressing GM-CSF," Human Gene Ther. 7: 1853-1860 (1996).
Rao et al., "Il-12 is an effective adjuvant to recombinant vaccinia virus-based tumor vaccines," J. Immunol. 156: 3357-3365 (1996).
Rodriguez et al., "Highly attenuated vaccinia virus mutants for the generation of safe recombinant viruses," Proc. Natl. Acad. Sci. USA 86: 1287-1291 (1989).
Rolston et al., "In vitro activity of LY264826, a new glycopeptide antibiotic, against gram-positive bacteria isolated from patients in cancer," Antimicrob. Agents Chemother. 34(11):2137-2141 (1990).
Roseman et al., "The vaccinia virus *Hin*dIII fragment: nucleotide sequence of the left 6.2kb," Virology 178: 410-418 (1990).
Roth et al,, "p53 as a target for cancer vaccines: recombinant canarypox virus vectors expressing p53 protect mice against lethal tumor cell challenge," Proc. Natl. Acad. Sci. USA 93: 4781-4786 (1996).
Schwartz and Dayhoff, eds., Atlas of Protein Sequence and Structure, National Biomedical Research Foundation, pp. 353-358 (1979).
Shilo, B. and R.A. Weinberg, "DNA sequences homologous to vertebrate oncogenes are conserved in *Drosophila melanogaster*," Proc. Natl. Acad. Sci. USA 78:6789-6792 (1981).
Shinozaki et al., "Oncolysis of multifocal hepatocellular carcinoma in the rat liver by hepatic artery infusion of vesicular stomatitis virus," Mol. Ther. 9(3): 368-376 (2004).
Silva et al., "Cloning, overexpression, and purification of functional human purine nucleoside phosphorylase," Protein Expr. Purif. 27(1): 158-164 (2003).
Smith, T.F. and M.S.Waterman, "Comparison of biosequences," Adv. Appl. Math. 2:482-489 (1981).
Sorscher et al., "Tumor cell bystander killing in colonic carcinoma utilizing the *Escherichia coli DeoD* gene to generate toxic purines," Gene Therapy 1(4): 233-238 (1994).
Stevens, D.L., "Stretoccocal toxic-shock syndrome: spectrum of disease, pathogenesis, and new concepts in treatment," Emerg. Infect. Dis. 1(3): 69-78 (1995).
Sugimoto, M. and K.Yamanouchi., "Characteristics of an attenuated vaccinia virus strain, LC16m0, and its recombinant virus vaccines," Vaccine 12(8): 675-681 (1994).
Sugimoto et al., "Gene structures of low-neurovirulent vaccinia virus LC16m0, LC16m8, and their Lister Original (LO) strains," Microbial. Immuol. 29: 421-428 (1985).
Suvorov et al., "Physical and genetic chromosomal map of an M type 1 strain of *Streptococcus pyogenes*," J. Bacteriol. 178(18): 5546-5549 (1996).

Suzuki et al., "Management of orbital lymphangioma using intralesional injection of OK-432," Br. J. Opthalmol. 84(6): 614-617 (2000).
Sze et al., "Dr. Gary J. Becker. Young Investigator Award: intraarterial adenovirus for metastatic gastrointestinal cancer: activity, radiographic response, and survival," J. Vasc. Interv. Radiol. 14(3): 279-290 (2003).
Takahashi-Nishimaki et al., "Genetic analysis of vaccinia virus Lister strain and its attenuated mutant LC16m8: production of intermediate variants by homologous recombination," J. Gen. Virol. 68: 2705-2710 (1987).
Theys et al., "Tumor-specific gene delivery using genetically engineered bacteria," Curr Gene Ther 3(3): 207-221 (2003).
Timiriasova et al., "[Analysis of reporter gene expression at different segments of the vaccinia virus genome]," Mol. Biol. (Mosk.) 27(2): 392-401 (1993) [article in Russian, English abstract on last page of article].
Timiryasova et al., "Construction of recombinant vaccinia viruses using PUV-inactivated virus as a helper," BioTechniques 31: 534-540 (2001).
Toth et al., "An oncolytic adenovirus vector combining enhanced cell-to-cell spreading, mediated by the ADP cytolytic protein, with selective replication in cancer cells with deregulated *Wnt* signaling," Cancer Research 64: 3638-3644 (2004).
Tsung et al. "Gene expression and cytopathic effect of vaccinia virus inactivated by psoralen and long-wave UV light," J. Virol. 70: 165-171 (1996).
Umphress et al., "Vaccinia virus mediated expression of human APC induces apoptosis in colon cancer cells," Transgenics 4:19-33 (2003).
Veijola et al., "Cloning, Baculovirus Expression, and Characterization of the α Subunit of Prolyl 4-Hydroxylase from the nematode *Caenorhabditis elegans*," J. Biol. Chem. 269: 26746-26753 (1994).
Vidal et al., "Tissue-specific control elements of the Thy-1 gene," EMBO J. 9(3): 833-840 (1990).
Watson et al. Molecular Biology of the Gene, 4th Edition, 1987, The Benjamin/Cummings Pub. co., p. 224.
Wolffe et al., "Deletion of the vaccinia virus B5R gene encoding a 42-kilodalton membrane glycoprotein inhibits extracellular virus envelope formation and dissemination," Journal of Virology 67(8): 4732-4741 (1993) and erratum in Journal of Virology, vol. 67, pp. 5709-5711 (1993).
Wu et al., "High resolution microPET imaging of carcino-embryonic antigen-positive xenografts by using a copper-64-labeled engineered antibody fragment," PNAS USA 97(15): 8495-8500 (2000).
Yang et al., "Whole-body optical imaging of green fluorescent protein-expressing tumors and metastases," Proc. Natl. Acad. Sci. USA 97(3):1206-1211 (2000).
Yang et al., "Effects of growth medium composition, iron sources and atmospheric oxygen concentrations on production of luciferase-bacterial magnetic particle complex by a recombinant *Magnetospirillum magneticum* AMB-1," Enzyme Microb. Technol. 29: 13-19 (2001).
Yazawa et al., "Current progress in suicide gene therapy for cancer," World J. Surg 26(7): 783-789 (2002).
Yoshida et al., "Cell growth-inhibitory action of SAGP, an antitumor glycoprotein from *Streptococcus pyogenes* (Su strain)," Jpn. J. Pharmacol. 45(2): 143-147 (1987).
Yoshida et al., "Characterization of a streptococcal antitumor glycoprotein (SAGP)," Life Sciences 62(12): 1043-1053 (1998).
Yoshida et al., "Growth-inhibitory effect of streptococcal antitumor glycoprotein on human epidermoid carcinoma A431 cells: involvement of dephosphorylation of epidermal growth factor receptor," Cancer Research 61(16): 6151-6157 (2001).
Zimmermann et al., "Independent regulatory elements in the nestin gene direct transgene expression to neural stem cells," Neuron 12: 11-24 (1994).
Zolotukhin et al., "A "Humanized" Green Fluorescent Protein cDNA adapted for high-level expression in mammalian cells," *J. Virol.* 70:4646-4654 (1996).
U.S. Appl. No. 10/872,156, filed Jun. 18, 2004.
Advisory Committee on Immunization Practices (ACIP), "Smallpox vaccination and adverse reactions: guidance for clinicians", Morbidity and Mortality Weekly Report 52(RR-4): 1-29 (Feb. 21, 2003).

(56) References Cited

OTHER PUBLICATIONS

Advisory Committee on Immunization Practices (ACIP), Vaccinia (smallpox) vaccine: recommendations of the Advisory Committee on Immunization Practices (ACIP), MMWR, 50(RR-10): 1-26 & ce1-ce7 (Jun. 22, 2001).
Aebischer et al., "Long-Term Cross-Species Brain Transplantation of a Polymer-Encapsulated Dopamine-Secreting Cell Line," Experimental Neurology 111:269-275 (1991).
Aebischer et al., "Functional Recovery in Hemiparkinsonian Primates Transplanted with Polymer-Encapsulated PC12 Cells," Experimental Neurology 126:151-158 (1994).
Aguilar, O.M. et al., The *nifEN* genes participating in FeMo cofactor biosynthesis and genes encoding dinitrogenase are part of the same operon in *Bradyrhizobium* species. Mol Gen Genet. 224(3):413-20 (1990).
Alcamí, A. et al., "Vaccinia virus strains Lister, USSR and Evans express soluble and cell-surface tumour necrosis factor receptors", J. Gen. Virol., 80: 949-959 (1999).
Antoine, G. et al., "Characterization of the vaccinia MVA hemagglutinin gene locus and its evaluation as an insertion site for foreign genes", Gene, 177: 43-46 (1996).
Arakawa, S. et al., "Clinical trial of attenuated vaccinia virus AS strain in the treatment of advanced adeocarcinoma", J. Cancer Res. Clin. Oncol., 113: 95-98 (1987).
Baeksgaard, L. and J.B. Sorensen, "Acute tumor lyssi syndrome in solid tumors—a case report and review of the literature", Cancer Chemother. Pharmacol., 51: 187-192 (2003).
Baker, R.O. et al., "Potential antiviral tehrapeutics for smallpox, monkeypox, and other *Orthopoxvirus* infections", Antiviral Research, 57: 13-23 (2003).
Balkwill, F., "Chemokine biology in cancer", Seminars in Immunol., 15: 49-55 (2003).
Baxby, D., "Poxviruses", Chapter 15 in *Principles and Practice of Clinical Virology*, Zuckerman, A.J. et al.(eds.), John Wiley & Sons Ltd., pp. 451-465 (2000).
Beebe, J.L. and E.W. Koneman, "Recovery of Uncommon Bacteria from Blood: Association with Neoplastic Disease," Clin. Microbiol. Rev., 8(3): 336-356 (1995).
Beerntsen, B.T. et al., "Genetics of Mosquito Vector Competenc," Microbiol. Mol. Biol. Rev., 64(1): 115-137 (2000).
Belas et al., "Bacterial Bioluminescence: Isolation and Expression of the Luciferase Genes from *Vibrio harveyi*," Science, 218: 791-793 (1982).
Bell, J.C. et al., "Getting oncolytic virus therapies off the ground," Cancer Cell, 4: 7-11 (2003).
Bendig, M.M., "The production of foreign proteins in mammalian cells," Genetic Engineering 7:91-127 (1988).
Bergsland, E.K. and A.P. Venook, "Shedding Old Paradigms: Developing Viruses to Treat Cancer," J. Clin. Oncol., 20(9): 2220-2222 (2002).
Bermudes et al., "Live bacteria as anticancer agents and tumor-selective protein delivery vectors," Current Opinion in Drug Discovery & Development 5(2):194-199 (2002).
Best et al., "Baboon/human homologies examined by spectral karyotyping (SKY): a visual comparison," Cytogenet Cell Genet. 82(1-2):83-7 (1998).
Bickels, J. et al., "Coley's toxin: historical perspective", Isr. Med. Assoc. J., 4(6): 471-472 (2002).
Blanchard, T.J. et al., "Modified vaccinia virus Ankara undergoes limited replication in human cells and lacks several immunomodulatory proteins: implications for use as a human vaccine," Journal of General Virology, 79: 1159-1167 (1998).
Blasco, R. and B. Moss, "Selection of recombinant vaccinia viruses on the basis of plaque formation," Gene, 158: 157-162 (1995).
Bogdahn et al., "Autocrine Tumor Cell Growth-inhibiting Activities from Human Malignant Melanoma", Cancer Research 49:5358-5363 (1989).
Borellini, F. and J.M. Ostrove, "The Transfer of Technology from the Laboratory to the Clinic: In Process Controls and Final Product Testing", Chapter 18 in *Gene Therapy Technologies, Applications and Regulations*, A. Meager (Ed.), John Wiley & Sons Ltd., pp. 359-373 (1999).
Boulanger, D. et al., "Morphogenesis and release of fowlpox virusm," Journal of General Virology, 81: 675-687 (2000).
Bouvier et al., "Functional characterization of the human dopamine D-4.2 receptor using vaccinia virus as an expression system," European Journal of Pharmacology 290(1):11-17 (1995).
Boyd, J.E., "Facilities for Large-Scale Production of Vectors under GMP Conditions", Chapter 20 in *Gene Therapy Technologies, Applications and Regulations*, A. Meager (Ed.), pp. 383-400 (1999).
Brain, J.D. et al., "Pulmonary intravascular macrophages: their contribution to the mononuclear phagocyte system in 13 species", Am. J. Physiol., 276(1 pt 1): L146-L154 (1999).
Breman, J.G. and D.A. Henderson, "Diagnosis and Management of Smallpox", N. Engl. J. Med., 346(17): 1300-1308 (2002).
Broder, C.C. et al., "Expression of foreign genes in cultured human primary macrophages using recombinant vaccinia virus vectors", Gene, 142: 167-174 (1994).
Broyles, S.S., "Vaccinia virus transcription", Journal of General Virology, 84: 2293-2303 (2003).
Brunke M et al., "Luciferase assembly after transport into mammalian microsomes involves molecular chaperones and peptidyl-prolyl cis/trans-isomerases," J Biol Chem. 271(38):23487-94 (1996).
Carroll, S.F. and R.J. Collier, "Active Site of *Pseudomonas aeruginosa* Exotoxin A," J. Biol. Chem. 262:8707-8711 (1987).
Carter, G.C. et al., "Vaccinia virus cores are transported on microtubules", Journal of General Virology, 84: 2443-2458 (2003).
Cavanagh, L.L. and U.H. von Andrian, "Travellers in many guises: The origins and destinations of dendritic cells", Immunology and Cell Biology, 80: 448-462 (2002).
Chalfie et al., "Green Fluorescent Protein as a Marker for Gene Expression," Science 263: 802-805 (1994).
Chambers, A.F. et al., "Dissemination and Growth of Cancer Cells in Metastatic Sites," Nat. Rev. Cancer, 2: 563-572 (2002).
Chambers, A.F. et al., "Molecular biology of breast cancer metastasis Clinical implications of experimental studies on metastatic inefficiency," Breast Cancer Res., 2: 400-407 (2000).
Chaudhary et al., "Role of domain II of *Pseudomonas* exotoxin in the secretion of proteins into the periplasm and medium by *Escherichia coli*," Proc. Natl. Acad. Sci. USA 85: 2939-2943 (1988).
Cheadle, E.J. and A.M. Jackson, "Bugs as Drugs for Cancer", Immunol., 107: 10-19 (2002).
Chen et al. "Evaluation of combined vaccinia virus-mediated antitumor gene therapy with p53, IL-2, and IL-12 in a glioma model." Cancer Gene Ther. 7(11):1437-47 (2000).
Chen et al. "Cancer gene therapy by direct tumor injections of a nonviral T7 vector encoding a thymidine kinase gene," Hum Gene Ther. 9(5):729-36 (1998).
Chiocca, E.A., "Oncolytic Viruses", Nat. Rev. Cancer, 2(12): 938-950 (2002).
Choi et al., "Efficient secretory production of alkaline phosphatase by high cell density culture of recombinant *Escherichia coli* using the *Bacillus* sp. endoxylanase signal sequence," Appl. Microbiol. Biotechnol. 53:640-645 (2000).
Cichutek, K., "Development and Regulation of Gene Therapy Drugs in Germany", Chapter 17 in Gene Therapy Technologies, Applications and Regulations, A. Meager (Ed.), John Wiley & Sons Ltd. pp. 347-358 (c1999).
Clairmont, C. et al., "Enhanced antitumor activity from tumor-targeting *Salmonella* expressing endostatin," American Association for Cancer Research: 91st Annual Meeting of the AACR, Apr. 1-5, 2000, 41:732 Abstract #4653 (2000).
Compton, J.L. and A.A. Szalay, "Insertion of nonhomologous DNA into the yeast genome mediated by homologous recombination with a cotransforming plasmid," Mol Gen Genet. 188(1):44-50 (1982).
Condeelis, J. and J.E. Segall, "Intravital imaging of cell movement in tumours", Nat. Rev. Cancer, 3: 921-930 (2003).
Contag et al., "Photonic detection of bacterial pathogens in living hosts," Mol. Microbiol. 18: 593-603 (1995).
Coupar, B.E.H. et al., "A general method for the construction of recombinant vaccinia viruses expressing multiple foreign genes", Gene, 68: 1-10 (1988).

(56) References Cited

OTHER PUBLICATIONS

Coussens, L.M. and Z. Werb, "Inflammation and cancer", Nature, 420: 860-867 (2002).
Craperi et al. "Increased bax expression is associated with cell death induced by ganciclovir in a herpes thymidine kinase gene-expressing glioma cell line." Hum Gene Ther. 10(4):679-688 (1999).
Cseh, S. et al., "Rapid freezing of mouse embryos in ethylene glycol at different preimplantation stages," Acta Veterinaria Hungarica 44(4):457-65 (1996).
Culver et al., "In vivo gene transfer with retroviral vector-producer cells for treatment of experimental brain tumors." Science. 256(5063):1550-2 (1992).
Davis, C. et al., "The role of inflammation in vascular injury and repair", Journal of Thrombosis and Haemostasis, 1: 1699-1709 (2003).
De Clercq, E., "Cidofovir in the therapy and short-term prophylaxis of poxvirus infections", Trends in Pharmacological Sciences, 23(10): 456-458 (2002).
Demers, G.W. et al., "Pharmacologic Indicators of Antitumor Efficacy for Oncolytic Virotherapy", Cancer Res., 63: 4003-4008 (2003).
Derwent English abstract for WO 94/10302, published May 11, 1994 entitled: "Vectors inhibiting HIV replication in potential host cells—contg. DNA encoding Pol, Gag, Env, Rev, and/or Tat in antisense direction and further DNA causing spontaneous amplification," Accession Nbr. 1994-152544 [19].
Diamond, D.C. et al. "Sequence comparison of baboon ABO histo-blood group alleles: lesions found in O alleles differ beween human and baboon," Blood Cells Mol Dis. 23(2):242-51 (1997).
Diamond, D.C., et al., "Genotying the baboon ABO histo-blood group locus by two-color fluorescence SSCP," Biotechniques 27(5):1054, 1056, 1058-59, 1061 (1999).
Dietrich, G. et al., "Delivery of antigen-encoding plasmid DNA into the cytosol of macrophages by attenuated suicide *Listeria monocytogenes*," Nat Biotechnol. 16(2):181-5 (1998).
Ding et al., "Zinc-dependent dimers observed in crystals of human endostatin," Proc. Natl. Acad. Sci. USA 95:10443-10448 (1998).
Dobbelstein, M., "Viruses in therapy—royal road or dead end?",Virus Research, 92: 219-221 (2003).
Domi, A. and B. Moss, "Cloning the vaccinia virus genome as a bacterial artificial chromosome in *Escherichia coli* and recovery of infectious virus in mammalian cells", Proc. Natl. Acad. Sci. U.S.A., 99(19): 12415-12420 (2002).
Dull et al., "Insulin-like growth factor H precursor gene organization in relation to insulin gene therapy," Nature 310: 777-781 (1984).
Eastham et al. "Prostate cancer gene therapy: herpes simplex virus thymidine kinase gene transduction followed by ganciclovir in mouse and human prostate cancer models." Hum Gene Ther. 7(4):515-23 (1996).
Ehrengruber, M.U., "Alphaviral gene transfer in neurobiology", Brain Research Bulletin, 59(1): 13-22 (2002).
Engebrecht et al., "Measuring Gene Expression with Light," Science 227: 1345-1347 (1985).
Escher, A. et al., "Bacterial luciferase αβ fusion protein is fully active as a monomer and highly sensitive in vivo to elevated temperature," Proc Natl Acad Sci U S A. 86(17):6528-32 (1989).
Escher, A et al., "The β subunit polypeptide of *Vibrio harveyi* luciferase determines light emission at 42° C.," Mol Gen Genet. 230(3):385-93 (1991).
Escher, A. and A.A. Szalay, "GroE-mediated folding of bacterial luciferases in vivo," Mol Gen Genet. 238(1-2):65-73 (1993).
Esposito, J.J. and F. Fenner, "Poxviruses", Chapter 85 in Field's Virology, 4th Edn., vol. 2, pp. 2885-2921. Edited by D. M. Knipe and P. M. Howley, Philadelphia: Lippincott Williams & Wilkins, (2001).
Fatyol, K et al., "Mer22-related sequence elements form pericentric repetitive DNA families in primates," Mol Gen Genet. 262(6):931-9 (2000).
Fatyol, K et al. "Molecular characterization of a stably transformed *Bombyx mori* cell line: identification of alternative transcriptional initiation sites of the A3 cytoplasmic actin gene." Mol Gen Genet. 260(1):1-8 (1998).

Fatyol, K et al., "An alternative intronic promoter of the *Bombyx* A3 cytoplasmic actin gene exhibits a high level of transcriptional activity in mammalian cells," Mol Gen Genet. 261(2):337-45 (1999).
Fatyol, K and A.A. Szalay, "The p14$^{ARF}$ tumor suppressor protein facilitates nucleolar sequestration of hypoxia-inducible factor-1α (HIF-1α ) and inhibits H1F-1-mediated transcription," J Biol Chem. 276(30):28421-28429 (2001).
Fernández-Piñas, F. and C.P. Wolk, "Expresssion of *luxCD-E* in *Anabaena* sp. can replace the use of exogenous aldehyde for in vivo localization of transcription by *luxAB*,"Gene 150:169-174 (1994).
Fidler, I.J., "The pathogenesis of cancer metastasis: the 'seed and soil' hypothesis revisited", Nature Cancer Research, 3: 1-6 (2003).
Foran, D.R. and W.M. Brown, "Nucleotide sequence of the LuxA and LuxB genes of the bioluminescent marine bacterium *Vibrio fischeri*," Nucleic Acids Res. 16: 777 (1988).
Forbes, N.S. et al., "Sparse Initial Entrapment of Systematically Injected *Salmonella typhimurium* Leads to Heterogenous Accumulation within Tumors," Cancer Res., 63: 5188-5193 (2003).
Fox, A.W., "Emergency and Compassionate-use INDs and Accelerated NDS or ANDA Approvals—Procedures, Benefits and Pitfalls", Chapter 26 in Principles and Practice of Pharmaceutical Medicine, A.J. Fletcher, et al.(Eds.), John Wiley & Sons, pp. 299-305, (2002).
Freed et al., "Survival of Implanted Fetal Dopamine Cells and Neurologic Improvement 12 to 46 Months After Transplantation for Parkinson's Disease," New England Journal of Medicine 327:1549-1555 (1992).
Freitag, N.E. and K.E. Jacobs, "Examination of *Listeria monocytogenes* Intracellular Gene Expression by Using Green Fluorescent Protein of *Aequorea victoria*," Infect.Immun. 67:1844-1852 (1999).
Friberg, S. and S. Mattson, "On the Growth Rates of Human Malignant Tumors: Implications for Medical Decision Making," Journal of Surgical Oncology, 65: 284-297 (1997).
Gallagher, R., "Vaccination Undermined", The Scientist, 17(22): 1-3 (2003).
Geng, J.G., "Directinal migration of leukocytes: their pathological roles in inflammation and strategies for development of anti-inflammatory therapies", Cell Res., 11(2): 85-88 (2001).
Geng, J.G., "Interaction of vascular endothelial cells with leukocytes, platelets and cancer cells in inflammation, thrombosis and cancer growth and metastasis," Acta Pharmacol. Sin, 24(12): 1297-1300 (2003).
Giacomin, L.T. and A.A. Szalay, "Expression of a PALI promoter luciferase gene function in *Arabidopsis thaliana* in response to infection by phytopathogenic bacteria," Plant Sci. 116: 59-72 (1996).
Gnant, M.F.X. et al, "Tumor-Specific Gene Delivery Using Recombinant Vaccinia Virus in a Rabbit Model of Liver Metastases", Journal of the National Cancer Institute, 91(20): 1744-1750 (1999).
Goetz et al., "Multicenter Study of Autologous Adrenal Medullary Transplantation to the Corpus Striatum in Patients with Advanced Parkinson's Disease", N. Eng. J. Med. 320:337-341 (1989).
Goetz, M et al., "Microinjection and growth of bacteria in the cytosol of mammalian host cells," Proc Natl Acad Sci U S A. 98(21):12221-12226. (2001).
Gomella, L.G. et al., "Phase I Study of Intravesical Vaccinia Virus As a Vector for Gene Therapy of Bladder Cancer", J. Urology, 166: 1291-1295 (2001).
Gómez, C.E. and M. Esteban, "Recombinant proteins produced by vaccinia virus vectors can be incorporated within the virion (IMV form) into different compartments," Arch. Virol., 146: 875-892 (2001).
Graff, C.P. and K.D. Wittnip, "Theoretical Analysis of Antibody Targeting of Tumor Spheroids: Importance of Dosage for Penetration, and Affinity for Retention", Cancer Res., 63: 1288-1296 (2003).
Gray, J.W., "Evidence emerges for early metastasis and parallel evolution of primary and metastatic tumors", Cancer Cell, 4(1): 4-6 (2003).
Green, D.R. and G.I. Evan, "A matter of life and death", Cancer Cell, 1: 19-30 (2002).
Greer III, L.F. and A.A. Szalay, "Imaging of light emission from the expression of luciferases in living cells and organisms: a review," Luminescence. 17(1):43-74 (2002).

(56) References Cited

OTHER PUBLICATIONS

Griffin, D.E., "A Review of Alphavirus Replication in Neurons", Neuroscience and Biobehavioral Reviews, 22(6): 721-723 (1998).

Guy et al., "Expression of the neu protooncogene in the mammary epithelium of transgenic mice induces metastatic disease," Proc. Natl. Acad. Sci.USA 89: 10578-10582 (1992).

Grove et al. "Virus-directed enzyme prodrug therapy using CB1954" Anti-Cancer Drug Design 14(6) 461-472 (1999).

Hacein-Bey-Abina, S. et al., "A Serious Adverse Event after Successful Gene Therapy for X-Linked Severe Combined Immunodeficiency", N. Engl. J. Med., 348(3): 255-266 (2003).

Hadley, R.G. et al., "Conservation of DNA regions adjacent to nifKDH homologous sequences in diverse slow-growing *Rhizobium* strains," J Mol Appl Genet. 2(3):225-36 (1983).

Haghighat et al. "Antitumor effect of IL-2, p53, and bax gene transfer in C6 glioma cells," Anticancer Res. 20(3A):1337-42 (2000).

Hall et al., "Adenovirus-mediated herpes simplex virus thymidine kinase gene and ganciclovir therapy leads to systemic activity against spontaneous and induced metastasis in an orthotopic mouse model of prostate cancer," Int J Cancer. 70(2):183-7 (1997).

Halsell, J.S. et al., "Myopericarditis Following Smallpox Vaccination Among Vaccinia-Naïve US Military Personnel", J. Am. Med. Assoc., 289(24): 3283-3289 (2003).

Hanahan, D. and R.A. Weinberg, "The Hallmarks of Cancer", Cell, 100: 57-70 (2000).

Hansen, R.M. and J.A. Libnoch, "Remission of Chronic Lymphocytic Leukemia After Smallpox Vaccination", Arch. Intern. Med., 138: 1137-1138 (1978).

Hawkins, L.K. et al., "Oncolytic biotherapy: a novel therapeutic platform", The Lancet Oncology, 3: 17-26 (2002).

Hemann et al., "High-Copy Expression Vector Based on Amplification-Promoting Sequences", DNA and Cell Biology 13:437-445 (1994).

Hermiston, T.W. and I. Kuhn, "Armed therapeutic viruses: Strategies and challenges to arming oncolytic viruses with therapeutic genes", Cancer Gene Therapy, 9: 1022-1035 (2002).

Hershey, P. et al., "Adjuvant Immunotherapy of Patients With High-Risk Melanoma Using Vaccinia Viral Lysates of Melanoma: Results of a Randomized Trial", Journal of Clinical Oncology, 20(20): 4181-4190 (2002).

Hess et al., "*Listeria monocytogenes* p60 supports host cell invasion by and in vivo survival of attenuated *Salmonella typhimurium*," Infect Immun. 63(5):2047-53 (1995).

Hollinshead, M. et al., "Vaccinia virus utilizes microtubules for movement to the cell surface," Journal of Cell Biology, 154: 389-402 (2001).

Holló, G et al., "Evidence for a megareplicon covering megabases of centromeric chromosome Segments," Chromosome Res. 4(3):240-7 (1996).

Hosokawa et al., "Pituitary Carcinoma of Pars Distalis as a Common Neoplasm in Fischer-344 Rats," Toxicol. Pathol. 21: 283-287 (1993).

Hughes, R.G. and N. Turner, "Financial Aspects of Clinical Trials", Chapter 42 in *Principles and Practice of Pharmaceutical Medicine*, A.J. Fletcher, et al.(eds.), pp. 501-512, John Wiley & Sons, Ltd. (2002).

Humlova, Z. et al., "Vaccinia virus induces apoptosis of infected macrophages," J. General Virol., 83: 2821-2832 (2002).

Jain, R.K. and B.T. Fenton, "Intratumoral Lymphatic Vessels: A Case of Mistaken Identity or Malfunction?", Journal of the National Cancer Institute, 94(6): 417-421 (2002).

Jain, R.K., "Molecular regulation of vessel maturation", Nat. Med., 9(6): 685-693 (2003).

Jemal, A. et al., "Cancer Statistics, 2003", CA Cancer J Clin, 53(1): 5-26 (2003).

Jeong, K.J. and S.Y. Lee, "Secretory Production of Human Leptin in *Escherichia coli*," Biotechnol.Bioeng. 67:398-407 (2000).

Kaniga et al., "Homologs of the *Shigella* IpaB and IpaC Invasins are Required for *Salmonella typhimurium* Entry into Cultured Epithelial Cells," J. Bacteriol. 177: 3965-3971 (1995).

Kawa, A. and S. Arakawa, "The Effect of Attenuated Vaccinia Virus As Strain on Multiple Myeloma; A Case Report", Japan. J. Exp. Med. 58(1): 79-81 (1987).

Keith, K.A. et al., "Evaluation of Nucleoside Phosphonates and Their Analogs and Prodrugs for Inhibition of *Orthopoxvirus* Replication," Antimicr. Agents Chemothera., 47(7): 2193-2198 (2003).

Keresó, J. et al., "De novo chromosome formations by large-scale amplification of the centromeric region of mouse chromosomes," Chromosome Res. 4(3):226-39 (1996).

Kern, E.R., "In vitro activity of potential anti-poxvirus agents", Antiviral Research 57: 35-40 (2003).

Kihara, A. and I. Pastan, "Analysis of Sequences Required for the Cytotoxic Action of a Chimeric Toxin Composed of *Pseudomonas* Exotoxin and Transforming Growth Factor α," Bioconj.Chem. 5: 532-538 (1994).

Kim, E.M. et al., "Overview analysis of adjuvant therapies for melanomaFa special reference to results from vaccinia melanoma oncolysate adjuvant therapy trials", Surgical Oncology, 10: 53-59 (2001).

Kleer, C.G. et al., "Molecular biology of breast cancer metastasis Inflammatory breast cancer: clinical syndrome and molecular determinants," Breast Cancer Res. 2: 423-429 (2000).

Kneissl, M. et al., "Interaction and assembly of murine pre-replicative complex proteins in yeast and mouse cells," J Mol Biol. 327(1):111-28 (2003).

Kolowsky K.S. et al., "Length of foreign DNA in chimeric plasmids determines the efficiency of its integration into the chromosome of the cyanobacterium *Synechococcus* R2," Gene 27(3):289-99 (1984).

Kondo et al., "Activity of.Immunotoxins Constructed with Modified *Pseudomonas* Exotoxin A Lacking the Cell Recognition Domain," J.Biol.Chem. 263: 9470-9475 (1988).

Krauss, O. et al., "An investigation of incorporation of cellular antigens into vaccinia virus particles", Journal of General Virology, 83: 2347-2359 (2002).

Kruse, M, et al., "Enzyme assembly after de novo synthesis in rabbit reticulocyte lysate involves molecular chaperones and immunophilins," J Biol Chem. 270(6):2588-94 (1995).

Kubes, P., "Introduction: The complexities of leukocyte recruitment", Seminars in Immunol., 14: 65-72 (2002).

Kunkel, E.J. and E.C. Butcher, "Plasma-cell homing", Nature Reviews Immunology, 3: 822-829 (2003).

Kwak, H. et al., "Poxviruses as vectors for cancer immunotherapy", Curr. Opin. Drug Disc. Develop., 6(2): 161-168 (2003).

Langridge W.H. et al, "Detection of baculovirus gene expression in insect cells and larvae by low light video image analysis," J Virol Methods. 61(1-2):151-6 (1996).

Langridge W.H. et al., "Uptake of DNA and RNA into cells mediated by electroporation," Methods Enzymol. 153:336-50. (1987).

Langridge, W.H. and , A.A.Szalay, "Bacterial and coelenterate luciferases as reporter genes in plant cells," Chapter 37 in Methods Mol Biol. 82:385-96.(1998).

Larson et al. "Triumph over mischance: a role for nuclear medicine in gene therapy," J Nucl Med. 38(8):1230-3 (1997).

Lawrence J.C., "The bacteriology of burns", J. of Hospital Infection 6: 3-17 (1985).

Lee et al., "The lux genes of the luminous bacterial symbiont *Photobacterium leiognathi*, of the ponyfish," Eur. J. Biochem. 201: 161-167 (1991).

Legocki et al., "Bioluminescence in soybean root nodules: Demonstration of a general approach to assay gene expression in vivo by using bacterial luciferase," Proc. Natl. Acad. Sci 83: 9080-9084 (1986).

Ley, K., "Integration of inflammatory signals by rolling neutrophils", Immunological Reviews, 186: 8-18 (2002).

Ley, K., "The role of selectins in inflammation and disease", Trends in Molec. Med., 9(6): 263-268 (2003).

Li et al "An engineered and assembled fusion protein of antitumor antibiotic lidamycin and scFV antibody directed against type IV collagenase" Yaoxue Xuebao 35(7) 488-91 (Jul. 2000) [English abstract on last page of article].

Lindvall et al., "Grafts of Fetal Dopamine Neurons Surive and Improve Motor Function in Parkinson's Disease," Science 237:574-577 (1990).

(56) References Cited

OTHER PUBLICATIONS

Liu, H et al., "Detection of GDNF secretion in glial cell culture and from transformed cell implants in the brains of live animals," Mol Genet Genomics. 266(4):614-23. (2001).

Liu, J. et al., "Visualizing and quantifying protein secretion using a *Renilla* luciferase-GFP fusion protein," Luminescence. 15(1):45-49 (2000).

Lorenz et al., "Isolation and expression of a cDNA encoding *Renilla reniformis* luciferase," PNAS USA 88: 4438-4442 (1991).

Lorenz et al., "Expression of the *Renilla reniformis* luciferase gene in mammalian cells," J Biolumin Chemilumin. 11(1):31-7 (1996).

Louie, A.Y. et al., "In vivo visualization of gene expression using magnetic resonance imaging", Nature Biotechnology, 18: 321-325 (2000).

Luscinskas, F.W. et al., "Leukocyte transendothelial migration: A junctional affair", Seminars in Immunology, 14: 105-113 (2002).

Luscinskas, F.W. et al., "The role of endothelial cell lateral junctions during leukocyte trafficking", Immunological Reviews, 186: 57-67 (2002).

Lusso, P., "Chemokines and Viruses: The Dearest Enemies", Virology, 273: 228-240 (2000).

Lyford, J., "Gene therapy 'cause T-cell leukemia': Insertional mutagenesis pinpointed as cause of T-cell Leukemia in X-SCID gene therapy trial", The Scientist, (Daily News, Oct. 20, 2003) pp. 1-4 (2003).

MacDonald, I.C. et al., "Cancer spread and micrometastasis development: quantitative approaches for in vivo models", BioEssays, 24: 885-893 (2002).

MacLaren et al. "Receptive non-invasive imaging of the dopamine D2 receptor gene in living animals" Gene Therapy (MacMillan Press)v.6 pp. 785-791, (May 1995).

MacLeod R.A .et al., "Expression of genes from the marine bacterium *Alteromonas haloplanktis* 214 in *Escherichia coli* K-12," Arch Microbiol. 142(3):248-52 (1985).

Maeda, H. et al., "Tumor vascular permeability and the EPR effect in macromolecular therapeutics: a review", J. Controlled Release, 65: 271-284 (2000).

Mahy, B.W.J., "An overview on the use of a viral pathogen as a bioterrorism agent: why smallpox?", Antivir. Res., 57: 1-5 (2003).

Maina C.V. et al., "Molecular weight determination program," Nucleic Acids Res. 12(1 Pt 2):695-702 (1984).

Makower, D. et al., "Phase II Clinical Trial of Intralesional Administration of the Oncolytic Adenovirus ONYX-015 in Patients with Hepatobiliary Tumors with Correlative p53 Studies," Clin. Cancer Res., 9: 693-702 (2003).

Mastrangelo, M.J. et al., "Poxvirus vectors: orphaned and underappreciated", J. Clin. Invest., 105(8): 1031-1034 (2000).

Matz et al., "Fluorescent proteins from nonbioluminescent Anthozoa species," Nat.Biotech. 17: 969-973 (1999).

Mayerhofer, R et al., "Monitoring of spatial expression of firefly luciferase in transformed zebrafish," J Biolumin Chemilumin. 10(5):271-5 (1995).

McCart, J.A. et al., "Complex interaction between the replicating oncolytic effect and the enzyme/prodrug effect of vaccinia-mediated tumor regression", Gene Therapy, 7: 1217-1223 (2000).

McCart, J.A. et al., "Systemic Cancer Therapy with a Tumor-selective Vaccinia Virus Mutant Lacking Thymidine Kinase and Vaccinia Growth Factor Genes", Cancer Research, 61: 8751-8757 (2001).

McDonald, D.M. and P.L. Choyke, "Imaging of angiogenesis: from microscope to clinic", Nature Medicine, 9(6): 713-725 (2003).

Meager, A. et al., "The Development of the Regulatory Process in Europe for Biological Medicines: How it Affects Gene Therapy Products", Chapter 16 in *Gene Therapy Technologies, Applications and Regulations*, A. Meager (Ed.), John Wiley & Sons Ltd., pp. 319-346 (1999).

Meighen, E.A. and R.B. Szittner, "Multiple Repetitive Elements and Organization of the *lux* Operons of Luminescent Terrestrial Bacteria," J. Bacteriol. 174(16):5371-5381 (1992).

Mengaud et al., "Expression in *Escherichia coli* and Sequence Analysis of the Listeriolysin O Determinant of *Listeria monocytogenes*," Infect.Immun. 56(4): 766-772 (1988).

Middleton, J. et al., "Leukocyte extravasation: chemokine transport and presentation by the endothelium", Blood, 100(12): 3853-3860 (2002).

Moore et al. , "Measuring transferrin receptor gene expression by NMR imaging," Biochimica et Biophysica Acta 1402(3):239-249 (1998).

Moore, A.E., "Effects of Viruses on Tumors", Annu. Rev. Microbiol., 8: 393-402 (1954).

Moretta, A., "Natural Killer Cells and Dendritic Cells: Rendezvous in Abused Tissues", Nat. Rev. Immunol., 2: 957-964 (2002).

Morris, D.W. et al., "Plasmid vectors capable of transferring large DNA fragments to yeast," DNA. 1(1):27-36 (1981).

Moss, B., "Poxviridae: the viruses and their replication," Chapter 84 in Field's Virology, $4^{th}$ Edn., vol. 2, pp. 2849-2883. Edited by D. M. Knipe and P. M. Howley, Philadelphia: Lippincott Williams & Wilkins, (2001).

Moss, B., "Poxviridae: the viruses and their replication," Chapter 83 in Fields Virology, 3rd Edn, pp. 2637-2671. Edited by B. N. Fields; D. M. Knipe & P. M. Howley. Philadelphia: Lippincott—Raven (1996).

Mountz et al. "Technetium-99m NeoTect imaging in vivo of T cells from hCAR transgenic mice," FASEB J. 16(5):A1211 March Meeting abstract (2002).

Nagahari et al. "Secretion into the culture medium of a foreign gene product from *Escherichia coli*: use of the *ompF* gene for secretion of human β-endorphin." EMBO J. 4(13A):3589-92 (1985).

Nettleton, P.F. et al., "Parapoxviruses are strongly inhibited in vitro by cidofovir," Antivir. Res., 48: 205-208 (2000).

Newton et al. "Expression and characterization of recombinant human eosinophil-derived neurotoxin and eosinophil-derived neurotoxin-anti-transferrin receptor sFv," J. Biol. Chem. 269(43):26739-45, (1994).

Neyts et al., "Therapy and short-term prophylaxis of poxvirus infections: historical background and perspectives", Antivir. Res. 57: 25-33 (2003).

Nibbering et al. "Radiolabelled antimicrobial peptides for imaging of infections: a review," Nucl Med Commun. 19(12):1117-21 (1998).

Nichterlein et al., "Clinafloxacin (CI 960) is Superior to Standard Therapeutics in the Treatment of Murine Listeriosis and Salmonellosis," Zentralbl.Bakteriol. 286: 401-412 (1997).

Nisato, R.E. et al., "Lymphangiogenesis and tumor metastasis", Thromb. Haemost., 90: 591-597 (2003).

Nolan G.P., et al., "Plasmid mapping computer program," Nucleic Acids Res. 12(1 Pt 2):717-29 (1984).

Noti J.D. et al., "Organization and characterization of genes essential for symbiotic nitrogen fixation from *Bradyrhizobium japonicum* 1110," J Bacteriol. 167(3):774-83 (1986).

Noti J.D. et al., "Site-directed Tn5 and transplacement mutagenesis: methods to identify symbiotic nitrogen fixation genes in slow-growing *Rhizobium*," Methods Enzymol. 154:197-217 (1987).

Ober, B.T. et al., "Immunogenicity and Safety of Defective Vaccinia Virus Lister:Comparison with Modified Vaccinia Virus Ankara", J. Virol., 76(15): 7713-7723 (2002).

O'Kane et al., "Visualization of Bioluminescence as a Marker of Gene Expression in *Rhizobium*-Infected Soybean Root Nodules," J. Plant Mol. Biol. 10: 387-399 (1988).

Olsson et al., "Engineering of monomeric bacterial luciferases by fusion of luxA and luxB genes in *Vibrio harveyi*," Gene 81(2):335-47 (1989).

Olsson, O. et al., "The use of the *luxA* gene of the bacterial luciferase operon as a reporter gene,"Mol Gen Genet. 215(1):1-9 (1988).

Overholser et al., "Experimental Bacterial Endocarditis after Dental Extractions in Rats with Periodontitis," J. Infect. Dis. 155(1) (1987), 107-112.

Padera, T.P. et al., "Lymphatic Metastasis in the Absence of Functional Intratumor Lymphatics", 296: 1883-1886 (2002).

Paniacli, D. et al., "Vaccinia virus vectors utilizing the /?-galactosidase assay for rapid selection of recombinant viruses and measurement of gene expression", Gene, 47: 193-199 (1986).

Pardal, R.. et al., "Applying the principles of stem-cell biology to cancer," Nature Reviews Cancer, 3: 895-902 (2003).

(56) References Cited

OTHER PUBLICATIONS

Parish, C.R., "Cancer immunotherapy: The past, the present and the future", Immunology and Cell Biology, 81: 106-113 (2003).
Pawelek, J.M. et al., "Bacteria as tumour-targeting vectors," The Lancet Oncology, 4: 548-556 (2003).
Pecora, A.L. et al., "Phase I Trial of Intravenous Administration of PV701, an Oncolytic Virus, in Patients With Advanced Solid Cancers", Journal of Clinical Oncology, 20(9): 2251-2266 (2002).
Peplinski, G.R. et al., "Vaccinia Virus for Human Gene Therapy", Surgical Oncology Clinics of North America, 7(3): 575-588 (1998).
Pluen, A. et al., "Role of tumor—host interactions in interstitial diffusion of macromolecules: Cranial vs. subcutaneous tumors", Proc. Natl. Acad. Sci. U.S.A., 98(8): 4628-4633 (2001).
Polverini et al., "Assay and Purification of Naturally Occuring Inhibitor of Angiogenesis," Methods in Enzymology 198:440-450 (1991).
Pongor S. et al., "Microcomputer programs for prediction and comparative evaluation of protein secondary structure from nucleotide sequence data: application to ribulose-1,5-bisphosphate carboxylase sequences," DNA. 4(4):319-26 (1985).
Pongor S. and A.A. Szalay, "Prediction of homology and divergence in the secondary structure of Polypeptides," Proc Natl Acad Sci U S A. 82(2):366-70 (1985).
Prasher et al., "Sequence Comparison of Complementary DNAs Encoding Aequorin Isotypes," Biochemistry 26: 1326-1332 (1987).
Prasher et al., "Primary structure of the *Aequorea victoria* green-fluorescent protein," Gene 111: 229-233 (1992).
Proudfoot, A.E.I. et al., "Strategies for Chemokine Antagonists as Therapeutics", Seminars in Immunology, 15: 57-65 (2003).
Puhlmann et al. "Thymidine kinase-deleted vaccinia virus expressing purine nucleoside phosphorylase as a vector for tumor-directed gene therapy." Hum Gene Ther. 10(4):649-57 (1999).
Quenelle, D.C. et al., "Efficacy of Multiple- or Single-Dose Cidofovir against Vaccinia and Cowpox Virus Infections in Mice", Antimicrobial Agents and Chemotherapy, 47(10): 3275-3280 (2003).
Ramirez, J.C. et al., "Tissue distribution of the Ankara strain of vaccinia virus (MVA) after mucosal or systemic administration", Arch. Virol., 148: 827-839 (2003).
Rangarajan, A. and R.A. Weinberg, "Comparative biology of mouse versus human cells: modeling human cancer in mice", Nature Reviews Cancer, 3: 952-959 (2003).
Ransohoff, R.M. et al., "Three or more routes for leukocyte migration into the central nervous system", Nat. Rev. Immunol., 3: 569-581 (2003).
Reddy et al. "Folate-mediated targeting of therapeutic and imaging agents to cancers," Crit Rev Ther Drug Carrier Syst. 15(6):587-627 (1998).
Reno, F., "Non-clinical Toxicology", Principles and Practice of Pharmaceutical Medicine, A.J. Fletcher et al.(eds.), ch.6: 55-64 (c2002) John Wiley & Sons Ltd.
Ribas, A. et al., "Current Developments in Cancer Vaccines and Cellular Immunotherapy", Journal of Clinical Oncology, 21(12): 2415-2432 (2003).
Ring, C.J.A., "Cytolytic viruses as potential anti-cancer agents", J. Gen. Virol., 83: 491-502 (2002).
Rodriguez, J.F. et al., "Expression of the firefly luciferase gene in vaccinia virus: A highly sensitive gene marker to follow virus dissemination in tissues of infected animals," Proc. Natl. Acad. Sci. U.S.A., 85: 1667-1671 (1988).
Rothenberg, M.L. et al., "Improving the evaluation of new cancer treatments: challenges and opportunities", Nat. Rev. Cancer, 3: 303-309 (2003).
Ruef et al. "Sternal wound infection after heart operations in pediatric patients associated with nasal carriage of *Staphylococcus aureus*" J. of Thoracic and Cardiovascular Surgery 112(3): 681-686 (1996).
Santoro, J. and M.E. Levison, "Rat Model of Experimental Endocarditis," Infect. Immun. 19(3): 915-918 (1978).
Schlör et al., "In vivo and in vitro studies on interactions between the components of the hemolysin (HlyA) secretion machinery of *Escherichia coli*," Mol.Gen.Genet. 256: 306-319 (1997).

Schmidt et al. "Generation of effective cancer vaccines genetically engineered to secrete cytokines using adenovirus-enhanced transferrinfection (AVET)," Gene. 190(1):211-6 (1997).
Shapiro, D. and A.W. Fox, "Biotechnology Products and Their Development", Principles and Practice of Pharmaceutical Medicine, A.J. Fletcher, et al.(eds.), ch.17: 191-201, c2002 John Wiley & Sons.
Shariatmadari et al., "Improved technique for detection of enhanced green fluorescent protein in transgenic mice," Biotechniques 30:1282-1285 (2001).
Shata, M.T. et al., "Optimization of recombinant vaccinia-based ELISPOT assay", J. Immunological Methods, 283: 281-289 (2003).
Shenk, T., "Delivery systems for gene therapy: the adenovirus", Stem Cell Biology and Gene Therapy, Quesenberry, P.J. et al. (Eds.), ch.6: pp. 161-178, c1998 Wiley-Liss, Inc.
Shepherd, A.J., "Good Laboratory Practice in the Research and Development Laboratory", Gene Therapy Technologies, Applications and Regulations, A. Meager (Ed.), ch.19: 375-381 (c1999) John Wiley & Sons Ltd.
Shimizu, Y. et al., "Immunotherapy of tumor-bearing mice utilizing virus help", Cancer Immunol. Immunother., 27: 223-227 (1988).
Sinkovics, J. and J. Horvath, "New Developments in the Virus Therapy of Cancer: A Historical Review", Intervirology, 36: 193-214 (1993).
Sinkovics, J.G. and J.C. Horvath, "Newcastle disease virus (NDV): brief history of its oncolytic strains", J. Clin. Virol., 16: 1-15 (2000).
Sinkovics, J.G. and J.C. Horvath, "Virus therapy of human cancers", Melanoma Research, 13: 431-432 (2003).
Smee, D.F. and R.W. Sidwell, "A review of compounds exhibiting anti-orthopoxvirus activity in animal models", Antiviral Research, 57: 41-52 (2003).
Smee, D.F. et al., "Effects of cidofovir on the pathogenesis of a lethal vaccinia virus respiratory infection in mice", Antivir. Res., 52: 55-62 (2001).
Smith, G.L. and B. Moss, "Infectious poxvirus vectors have capacity for at least 25000 base pairs of foreign DNA", Gene, 25: 21-28 (1983).
Smith, G.L. et al., "The formation and function of extracellular enveloped vaccinia virus", J. Gen. Virol., 83: 2915-2931 (2002).
Somia, N. and I.M. Verma, "Gene Therapy: Trial and Tribulations", Nat. Rev. Genet., 1(2): 91-99 (2000).
Spencer et al., "Unilateral Transplantation of Human Fetal Mesencephalic Tissue Into the Caudate Nucleus of Patients with Parkinson's Disease", New England Journal of Medicine 327: 1541-1548 (1992).
Stehle, G. et al., "Plasma protein (albumin) catabolism by the tumor itself—implications for tumor metabolism and the genesis of cachexia", Critical Reviews in Oncology/Hematology, 26: 77-100 (1997).
Stojdl, D.F. et al., "VSV strains with defects in their ability to shut-down innate immunity are potent systemic anti-cancer agents", Cancer Cell, 4:263-275 (2003).
Sudimack et al. "Targeted drug delivery via the folate receptor." Adv Drug Deliv Rev. 41(2):147-62 (2000).
Sutton et al. "In vivo adenovirus-mediated suicide gene therapy of orthotopic bladder cancer." Mol Ther. 2(3):211-7 (2000).
Suzuki M., Szalay A.A., "Bacterial transformation using temperature-sensitive mutants deficient in peptidoglycan synthesis," Methods Enzymol. 68:331-342 (1979).
Suzuki, S. et al. "Coexpression of the partial androgen receptor enhances the efficacy of prostate-specific antigen promoter-driven suicide gene therapy for prostate cancer cells at low testosterone concentrations," Cancer Research 61(4):1276-1279 (2001).
Symons, J.A. et al., "A study of the vaccinia virus interferon-γ receptor and its contribution to virus virulence", Journal of General Virology, 83: 1953-1964 (2002).
Szalay A.A. et al., "Separation of the complementary strands of DNA fragments on polyacrylamide gels," Nucleic Acids Res. 4(5):1569-78 (1977).
Szalay A.A .et al, "Genetic engineering of halotolerance in microorganisms: a summary," Basic Life Sci. 14:321-32 (1979).
Technology Evaluation Center, "Special Report: Vaccines for the Treatment of Malignant Melanoma", TEC Assessment Program, 16(4): 1-46 (2001).

(56) References Cited

OTHER PUBLICATIONS t'Hart, B.A. et al., "Gene thereapy in nonhuman primate models of human autoimmune disease", Gene Therapy, 10: 890-901 (2003).
Theuer et al., "A recombinant form of *Pseudomonas* exotoxin directed at the epidermal growth factor receptor that is cytotoxic without requiring proteolytic processing," J.Biol.Chem. 267(24): 16872-16877 (1992).
Timiryasova, T.M. et al., "Antitumor Effect of Vaccinia Virus in Glioma Model", Oncology Research, 11(3): 133-144 (1999).
Timiryasova, T.M. et al., "Replication-deficient vaccinia virus gene therapy vector: evalution of exogenous gene expression mediated by PUV-inactivated virus in glioma cells", Journal of Gene Medicine, 3: 468-477 (2001).
Timiryasova, T.M. et al., "Vaccinia virus-mediated expression of wild-type p53 suppresses glioma cell growth and induces apoptosis." Int J Oncol. 14(5):845-54 (1999).
Timiryasova, T.M. et al., "Visualization of Vaccinia Virus Infection Using the *Renilla*-Luciferase-GFP Fusion Protein", Bioluminescence & chemiluminescence: Proceedings of the 11th International Symposium on Bioluminescence Chemiluminescence: Asilomar Conference Grounds, Pacific Grove, Monterey, California: Sep. 6-10, 2000 / (eds.): Case, J.F. et al., World Scientific Publishing Co. (c2001), pp. 457-460.
Timpl, "Antibodies to Collagens and Procollagens," Methods Enzymol. 82: 472-498 (1982).
Tjuvajev, J. et al., "*Salmonella*-based tumor-targeted cancer therapy: tumor amplified protein expression therapy (TAPET™) for diagnostic imaging," J. Controlled Release, 74: 313-315 (2001).
Toguchi et al., "Suicide Gene Therapy of C6 Glioma Cells Mediated by Replication-Deficient and Replication Competent Vaccinia Viruses," Cancer Gene Therapy 10: S32 (2003) presented at the Eleventh International Conference on Gene Therapy of Cancer, Dec. 12-14, 2002, San Diego California.
Tokugawa et al., "A model system for the continuous production of a heterologous protein using a novel secretion promoting factor which operates in *Escherichia coli*," J.Biotechnol. 37:33-37 (1994).
Tokugawa et al., "A novel protein secretion factor from a *Vibrio* species which operates in *Escherichia coli*," J.Biotechnol. 35: 69-76 (1994).
Tonetti DA et al "Stable transfection of an estrogen receptor beta cDNA isoform into MDA-MB-231 breast cancer cells," J Steroid Biochem Mol Biol. 87(1):47-55 (2003).
Tresco et al., "Polymer-encapsulated PC12 Cells: Long-Term Survival and Associated Reduction in Lesion-Induced Rotational Behavior", Cell Transplantation 1:255-264 (1992).
Tscharke, D.C. et al., "A model for vaccinia virus pathogenesis and immunity based on intradermal injection of mouse ear pinnae", J. Gen. Virol., 80: 2751-2755 (1999).
Tscharke, D.C. et al., "Dermal infection with vaccinia virus reveals roles for virus proteins not seen using other inoculation routes", Journal of General Virology, 83: 1977-1986 (2002).
Tseng, J.-C. et al., "In Vivo Antitumor Activity of Sindbis Viral Vectors", Journal of the National Cancer Institute, 94(23): 1790-1802 (2002).
Tseng, J.-C. et al., "Systemic tumor targeting and killing by Sindbis viral vectors", Nat. Biotechnol., 22(1): 70-77 (2004).
Tsung, K. et al., "Immune Response Against Large Tumors Eradicated by Treatment with Cyclophosphamide and IL-12", J. Immunol., 160: 1369-1377 (1998).
Vanderplasschen, A. et al., "Antibodies against vaccinia virus do not neutralize extracellular enveloped virus but prevent virus release from infected cells and comet formation", Journal of General Virology, 78: 2041-2048 (1997).
Vanderplasschen, A. et al., "Intracellular and extracellular vaccinia virions enter cells by different mechanisms", Journal of General Virology, 79: 877-887 (1998).
Varghese, S. and S.D. Rabkin, "Oncolytic herpes simplex virus vectors for cancer virotherapy", Cancer Gene Therapy, 9: 967-978 (2002).

Vento, S. and F. Cainelli, "Infections in patients with cancer undergoing chemotherapy: aetiology, prevention, and treatment", Lancet, 4: 595-604 (2003).
Vestweber, D., "Regulation of endothelial cell contacts during leukocyte extravasation", Curr. Opin. Cell Biol., 14: 587-593 (2002).
Vile, R. et al., "The oncolytic virotherapy treatment platform for cancer: Unique biological and biosafety points to consider", Cancer Gene Therapy, 9: 1062-1067 (2002).
Vogel, J.R., "Outsourcing Clinical Drug Development Activities to Contract Reseach Organizations (CROs): Critical Success Factors", Principles and Practice of Pharmaceutical Medicine, A.J. Fletcher et al.(eds.), ch.40: 461-482 (c2002) John Wiley & Sons Ltd.
Voisey et al. Elimination of internal restriction enzyme sites from a bacterial luminescence (luxCDABE) operon. Biotechniques 24(1):56, 58 (1998).
Wallack, M.K. et al., "A Phase III Randomized, Double-Blind, Multiinstitutional Trial of Vaccinia Melanoma Oncolysate-Active Specific Immunotherapy for Patients with Stage II Melanoma", Cancer, 75(1): 34-42 (1995).
Wallack, M.K. et al., "Increased Survival of Patients Treated With a Vaccinia Melanoma Oncolysate Vaccine", Annals of Surgery, 226(2): 198-206 (1997).
Wallack, M.K. et al., "Surgical Adjuvant Active Specific Immunotherapy for Patients with Stage III Melanoma: The Final Analysis of Data From a Phase III, Randomized, Double-Blind, Multicenter Vaccinia Melanoma Oncolysate Trial", J. Am. Coll. Surg., 187(1): 69-79 (1998).
Wang Y. et al., "A study of protein-protein interactions in living cells using luminescence resonance energy transfer (LRET) from *Renilla* luciferase to *Aequorea* GFP," Mol Gen Genet. 264(5):578-87 (2001).
Wang Y. et al., "*Renilla* luciferase—*Aequorea* GFP (Ruc-GFP) fusion protein, a novel dual reporter for real-time imaging of gene expression in cell cultures and in live animals," Mol Genet Genomics. 268(2):160-8 (2002).
Wang, Y. et al., "The *Renilla* Luciferase-Modified GFP Fusion Protein is Functional in Transformed Cells", Bioluminescence & chemiluminescence: Proceedings of the 9th International Symposium on Bioluminescence Chemiluminescence: Woods Hole, Massachusetts, Oct. 1996 / (eds.) Hastings, J.W. et al., John Wiley & Sons Ltd., pp. 419-422 (c1997).
Warrington et al. "Developing VDEPT for DT-diaphorase (NQO1) using an AAV vector plasmid," Int J Radiat Oncol Biol Phys. 42(4):909-12 (1998).
Wegner et al., "Cis-acting suquences from mouse rDNA promote plasmid DNA amplification and persistence in mouse cells: implication of HMG-I in their function", Nucleic Acids Research 17:9909-9932 (1989).
Weissleder et al. "Drug targeting in magnetic resonance imaging," Magnetic Resonance Quarterly. 8(1):55-63 (1992).
Weissleder, T. et al., "In vivo magnetic resonance imaging of transgene expression", Nat. Med. , 6(3): 351-354 (2000).
Welling et al "Technetium-99m labelled antimicrobial peptides discriminate between bacterial infections and sterile inflammations." Eur J Nucl Med. 27(3):292-301 (2000).
Welling et al "Radiochemical and biological characteristics of 99mTc-UBI 29-41 for imaging of bacterial infections." Nucl Med Biol. 29(4):413-22 (2002).
West et al. "Identification of a somatodendritic targeting signal in the cytoplasmic domain of the transferrin receptor." J Neurosci. 17(16):6038-47 (1997).
Wharton, M. et al., "Recommendations for Using Smallpox Vaccine in a Pre-Event Vaccination Program", MMWR, 52(RR-7): 1-16 (2003).
Whitley, R.J., "Smallpox: a potential agent of bioterrorism", Antiviral Research 57: 7-12 (2003).
Williams J.G. and Szalay A.A., "Stable integration of foreign DNA into the chromosome of the cyanobacterium *Synechococcus* R2," Gene. 24(1):37-51 (1983).
Winn et al., "Behavioral Recovery following Intrastriatal Implantation of Microencapsulated PC12 Cells", Experimental Neurology 113:322-329 (1991).
Winn, S.R. et al., Polymer-encapsulated cells genetically modified to secrete human nerve growth factor promote the survival of

(56) References Cited

OTHER PUBLICATIONS axotomized septal cholinergic neurons, Proceedings of the National Academy of Science, 91:2324-2328 (1994).
Wisher, M., "Biosafety and product release testing issues relevant to replication-competent oncolytic viruses", Cancer Gene Therapy, 9: 1056-1061 (2002).
Wittrup, D., "Tumor Targeting Theory", IBC's 15th Annual International Antibody Engineering Conference entitled Antibody Engineering: Forging the Future of Antibody Therapeutics, Nov. 30-Dec. 3, 2003—The Paradise Point Resort—San Diego, CA, pp. 1-17.
Wlodaver, C.G. et al., "Laboratory-acquired vaccinia infection", Journal of Clinical Virology, xxx: 1-5 (2003).
Wong, M.M. and E.N. Fish, "Chemokines: attractive mediators of the immune response", Semin. Immunol. 15: 5-14 (2003).
Yadav, R. et al., "Migration of leukocytes through the vessel wall and beyond," Thromb. Haemost., 90: 598-606 (2003).
Yansura, D.G. and Henner D.J., "Use of the *Escherichia coli* lac repressor and operator to control gene expression in *Bacillus subtilis*," Proc. Natl. Acad. Sci USA 81: 439-443 (1984).
Yu Y.A., "Visualization of molecular and cellular events with green fluorescent proteins in developing embryos: a review," Luminescence. 18(1):1-18 (2003) Erratum in: Luminescence. Jul.-Aug. 2003; 18(4):243.
Yu Y.A. et al., "A *Renilla* luciferase-*Aequorea* GFP (*ruc-gfp*) fusion gene construct permits real-time detection of promoter activation by exogenously administered *mife*pristone in vivo," Mol Genet Genomics. 268(2):169-78 (2002).
Yu Y.A. et al., "Optical imaging: bacteria, viruses, and mammalian cells encoding light-emitting proteins reveal the locations of primary tumors and metastases in animals,"Anal Bioanal Chem. 377(6):964-72 (2003).
Yu, Y.A. et al. "Visualization of tumors and metastases in live animals with bacteria and vaccinia virus encoding light-emitting proteins," Nat Biotech. 22(3): 313-320 (2004).
Yun A.C. et al. "Nitrogenase promoter-*lacZ* fusion studies of essential nitrogen fixation genes in *Bradyrhizobium japonicum* I110," J Bacteriol. 167(3):784-91 (1986).
Zamir et al. "Stable chromosomal integration of the entire nitrogen fixation gene cluster from *Klebsiella pneumoniae* in yeast," Proc Natl Acad Sci U S A. 78(6):3496-500 (1981).
Zaucha, G.M. et al., "The Pathology of Experimental Aerosolized Monkeypox Virus Infection in Cynomolgus Monkeys (*Macaca fascicularis*)", Lab. Invest., 81: 1581-1600 (2001).
Zeh, H.J. and D.L. Bartlett, "Development of a replication-selective, oncolytic poxvirus for the treatment of human cancers", Cancer Gene Therapy, 9: 1001-1012 (2002).
Zhang et al., "Urothelium-specific Expression of an Oncogene in Transgenic Mice Induced the Formation of Carcinoma in Situ and Invasive Transitional Cell Carcinoma," Cancer Res.59: 3512-3517 (1999).
Zhu et al., "Smad3 Mutant Mice Develop Metastatic Colorectal Cancer," Cell 94: 703-714 (1998).
Zinkernagel, R.M., "Uncertainties—discrepancies in immunology", Immunological Reviews, 185: 103-125 (2002).
Zinn et al., "Simulataneous evaluation of dual gene transfer to adherent cells by gamma-ray imaging," Nuclear Medicine and Biology 28(2):135-144 (2001).
Zinn et al. "Noninvasive monitoring of gene transfer using a reporter receptor imaged with a high-affinity peptide radiolabeled with 99mTc or 188Re," J Nucl Med. May 2000;41(5):887-95.
Aboody et al., "Neural stem cells display extensive tropism for pathology in adult brain: evidence from intracranial gliomas," Proc Natl Acad Sci U S A. 97(23):12846-51 (2000).
Aksac S., "[Antibody formation against *Agrobacterium tumefaciens* in patients with various cancers]," Turk Hij Tecr Biyol Derg. 34(1-2):48-51 (1974) [Article in Italian].
Al'tshtein et al., "[Isolation of a recombinant vaccinia virus based on the LIVP strain inducing the surface antigen of the hepatitis B virus]," Dokl Akad Nauk SSSR. 285(3):696-9 (1985) [Article in Russian].

Anaissie et al., "*Pseudomonas putida*. Newly recognized pathogen in patients with cancer," Am J Med. 82(6):1191-4 (1987).
Anand, A and A.E. Glatt, "*Clostridium difficile* infection associated with antineoplastic chemotherapy: a review," Clin Infect Dis. 17(1):109-13 (1993).
Arab et al., "Verotoxin induces apoptosis and the complete, rapid, long-term elimination of human astrocytoma xenografts in nude mice," Oncol Res. 11(1):33-9 (1999).
Arakawa et al., "Clinical trial of attenuated vaccinia virus AS strain in the treatment of advanced adenocarcinoma. Report on two cases," J Cancer Res Clin Oncol. 113(1):95-8 (1987).
ATCC Accession No. 11842.
ATCC Accession No. 11863.
ATCC Accession No. 13124.
ATCC Accession No. 15696.
ATCC Accession No. 15697.
ATCC Accession No. 15707.
ATCC Accession No. 15955.
ATCC Accession No. 17583.
ATCC Accession No. 17836.
ATCC Accession No. 19401.
ATCC Accession No. 19402.
ATCC Accession No. 19404.
ATCC Accession No. 25527.
ATCC Accession No. 25752.
ATCC Accession No. 25923.
ATCC Accession No. 27337.
ATCC Accession No. 27555.
ATCC Accession No. 29212.
ATCC Accession No. 35782.
ATCC Accession No. 3624.
ATCC Accession No. 37253.
ATCC Accession No. 393.
ATCC Accession No. 43142.
ATCC Accession No. 47054.
ATCC Accession No. 51299.
ATCC Accession No. 700057.
ATCC Accession No. 824.
ATCC Accession No. 9338.
ATCC Accession No. 9714.
ATCC Accession No. BAA-250D.
ATCC Accession No. CCL-70.
Azmi et al., "In situ localization of endogenous cytokinins during shooty tumor development on *Eucalyptus globulus* Labill," Planta 213(1):29-36 (2001).
Baker, S.J. and E.P. Reddy, "Transducers of life and death: TNF receptor superfamily and associated proteins," Oncogene 12(1):1-9 (1996).
Banerjee et al., "*Bacillus* infections in patients with cancer," Arch Intern Med. 148(8):1769-74 (1988).
Bentires-Alj et al., "Cytosine deaminase suicide gene therapy for peritoneal carcinomatosis," Cancer Gene Ther. 7(1):20-6 (2000).
Bermudes et al., "Tumor-targeted *Salmonella*: Highly selective delivery vectors," Adv Exp Med Biol. 465:57-63 (2000).
Beyer et al., "Oncoretrovirus and lentivirus vectors pseudotyped with lymphocytic choriomeningitis virus glycoprotein: generation, concentration, and broad host range," J Virol. 76(3):1488-95 (2002).
Biffi et al., "Antiproliferative effect of fermented milk on the growth of a human breast cancer cell line," Nutr Cancer. 28(1):93-9 (1997).
Block et al., "Gene therapy of metastatic colon carcinoma: regression of multiple hepatic metastases by adenoviral expression of bacterial cytosine deaminase," Cancer Gene Ther. 7(3):438-45 (2000).
Bodey et al., "Clostridial bacteremia in cancer patients. A 12-year experience," Cancer 67(7):1928-42 (1991).
Bogdanov et al., "Antitumour glycopeptides from *Lactobacillus bulgaricus* cell wall," FEBS Lett. 57(3):259-61 (1975).
Bogdanov et al., "Antitumor action of glycopeptides from the cell wall of *Lactobacillus bulgaricus*," Bulletin of Experimental Biology and Medicine. 84(12): 1750-1753 (1977); translated from the original Russian article: Byulleten' Éksperimental'noi Biologii I Meditsiny 84(12):709-12 (1977).

(56) References Cited

OTHER PUBLICATIONS

Certified English translation of Timiryasova et al., "Analysis of Reporter Gene Expression in Various Regions of the Genome of the Vaccinia Virus," Molecular Biology 27(2): 2-11 (1993).
Chang et al., "Differential apoptotic susceptibility to anti-Fas IgM and anticancer drugs in a human endometrial adenocarcinoma cell line HHUA on laminin and type I collagen," Osaka City Med J. 44(2):173-80 (1998).
Chatterjee, B.D. and C.K. Chakraborti, "Non-sporing anaerobes in certain surgical group of patients," J Indian Med Assoc. 93(9):333-5, 339 (1995).
Chen et al., "Low-dose vaccinia virus-mediated cytokine gene therapy of glioma," J Immunother. 24(1):46-57 (2001).
Clairmont et al., "Biodistribution and genetic stability of the novel antitumor agent VNP20009, a genetically modified strain of *Salmonella typhimurium*," J Infect Dis. 181(6):1996-2002 (2000).
Cole, A.M. and T. Ganz, "Human antimicrobial peptides: analysis and application," Biotechniques. 29(4):822-6, 828, 830-1 (2000).
Collins, J.L. and C.J. Wust, "Suppression of SV40 tumors after immunization with group a *Streptococcus pyogenes* and *Bordetella pertussis*," Cancer Res. 34(5):932-7 (1974).
Dang et al., "Combination bacteriolytic therapy for the treatment of experimental tumors," Proc Natl Acad Sci U S A. 98(26):15155-60 (2001).
de Lorenzo V., "Isolation and characterization of microcin E492 from *Klebsiella pneumoniae*," Arch Microbiol. 139(1):72-5 (1984).
Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-31 (2000).
Djeha et al., Combined adenovirus-mediated nitroreductase gene delivery and CB1954 treatment: a well-tolerated therapy for established solid tumors. Mol Ther. Feb. 2001;3(2):233-40.
Duncan, J.R. and M.J. Welch, "Intracellular metabolism of indium-111-DTPA-labeled receptor targeted proteins," J Nucl Med. 34(10):1728-38 (1993).
Dunn et al., "Cancer immunoediting: from immunosurveillance to tumor escape.," Nat Immunol. 3(11):991-8 (2002).
Eliopoulos et al., "CD40 induces apoptosis in carcinoma cells through activation of cytotoxic ligands of the tumor necrosis factor superfamily," Mol Cell Biol. 20(15):5503-15 (2000).
Essbauer, S. and W. Ahne, "Viruses of lower vertebrates," J Vet Med B Infect Dis Vet Public Health. 48(6):403-75 (2001).
Farkas-Himsley et al., "The bacterial colicin active against tumor cells in vitro and in vivo is verotoxin 1," Proc Natl Acad Sci U S A. 92(15):6996-7000 (1995).
Feng et al, "The antitumor activity of a mixed bacterial vaccine against mouse hepatoma," Chinese Pharmaceutical Journal 30(7): 405-407 (1995) [Article in Chinese].
Fodor et al., "Vaccinia virus mediated p53 gene therapy for bladder cancer in an orthotopic murine model," J. Urol. 173(2):604-9 (2005).
Friedlos et al., "Three new prodrugs for suicide gene therapy using carboxypeptidase G2 elicit bystander efficacy in two xenograft models," Cancer Res. 62(6):1724-1729 (2002).
Gnant et al., "Systemic administration of a recombinant vaccinia virus expressing the cytosine deaminase gene and subsequent treatment with 5-fluorocytosine leads to tumor-specific gene expression and prolongation of survival in mice," Cancer Res. 59(14):3396-3403 (1999).
Golstein, P., "Cell death: TRAIL and its receptors," Curr Biol. 7(12):R750-R753 (1997).
Greco et al., "Development of a novel enzyme/prodrug combination for gene therapy of cancer: horseradish peroxidase/indole-3-acetic acid," Cancer Gene Ther. 7(11):1414-20 (2000).
Gridley et al., "Evaluation of radiation effects against C6 glioma in combination with vaccinia virus-p53 gene therapy," Int J Oncol. 13(5):1093-8 (1998).
Gridley et al., "Proton radiation and TNF-α/Bax gene therapy for orthotopic C6 brain tumor in Wistar rats," Technol Cancer Res Treat. 3(2):217-27 (2004).

Grote et al., "Live attenuated measles virus induces regression of human lymphoma xenografts in immunodeficient mice," Blood 97(12):3746-54 (2001).
Hall et al., "In vitro efficacy of transferrin-toxin conjugates against glioblastoma multiforme," J Neurosurg. 76(5):838-44 (1992).
Hall et al., "In vivo efficacy of intrathecal transferrin-*Pseudomonas* exotoxin A immunotoxin against LOX melanoma," Neurosurgery 34(4):649-55; discussion 655-6 (1994).
Hansen, R.M. and J.A. Libnoch, "Remission of chronic lymphocytic leukemia after smallpox vaccination," Arch Intern Med. 138(7):1137-8 (1978).
Harrison et al., "Gene-modified PA1-Stk cells home to tumor sites in patients with malignant pleural mesothelioma," Ann Thorac Surg. 70(2):407-11 (2000).
Hasegawa et al., "Avoidance of bone marrow suppression using A-5021 as a nucleoside analog for retrovirus-mediated herpes simplex virus type I thymidine kinase gene therapy,." Cancer Gene Ther. 7(4):557-62 (2000).
Herrlinger et al., "Neural precursor cells for delivery of replication-conditional HSV-1 vectors to intracerebral gliomas," Mol Ther. 1(4):347-57 (2000).
Hetz et al., "Microcin E492, a channel-forming bacteriocin from *Klebsiella pneumoniae*, induces apoptosis in some human cell lines," Proc Natl Acad Sci U S A. 99(5):2696-701 (2002).
Hostanska et al., "Aqueous ethanolic extract of St. John's wort (*Hypericum perforatum* L.) induces growth inhibition and apoptosis in human malignant cells in vitro," Pharmazie 57(5):323-31 (2002).
Hsueh et al., "Outbreak of *Pseudomonas fluorescens* bacteremia among oncology patients," J Clin Microbiol. 36(10):2914-7 (1998).
Huang et al., "Impact of liver P450 reductase suppression on cyclophosphamide activation, pharmacokinetics and antitumoral activity in a cytochrome P450-based cancer gene therapy model," Cancer Gene Ther. 7(7):1034-42 (2000).
Ianaro et al., "A nitric oxide synthase inhibitor reduces inflammation, down-regulates inflammatory cytokines and enhances interleukin-10 production in carrageenin-induced oedema in mice," Immunology. 82(3):370-5 (1994).
Jiang et al. "Apoptosis in human hepatoma cell lines by chemotherapeutic drugs via Fas-dependent and Fas-independent pathways," Hepatology. 29(1):101-10 (1999).
Johnson et al., "Improved tumor-specific immunotoxins in the treatment of CNS and leptomeningeal neoplasia," J Neurosurg. 70(2):240-8 (1989).
Jordan et al., "Melanocyte-Directed enzyme prodrug therapy (MDEPT): development of second generation prodrugs for targeted treatment of malignant melanoma," Bioorg Med Chem. 9(6):1549-58 (2001).
Kaklij et al., "Antitumor activity of *Streptococcus thermophilus* against fibrosarcoma: role of T-cells,"Cancer Lett. 56(1):37-43 (1991).
Kaklij, G.S. and S.M. Kelkar, "Tumor-specific transplantation resistance in mice after treatment of initial tumors with *Streptococcus thermophilus*," Microbiol Immunol. 40(1):55-8 (1996).
Kammertoens et al., "Combined chemotherapy of murine mammary tumors by local activation of the prodrugs ifosfamide and 5-fluorocytosine," Cancer Gene Ther. 7(4):629-36 (2000).
Kan et al., "Direct retroviral delivery of human cytochrome P450 2B6 for gene-directed enzyme prodrug therapy of cancer," Cancer Gene Ther. 8(7):473-82 (2001).
Kato et al., "Antitumor activity of *Lactobacillus casei* in mice," Gann. 72(4):517-23 (1981).
Kato et al., "Correlation between increase in 1a-bearing macrophages and induction of T cell-dependent antitumor activity by *Lactobacillus casei* in mice," Cancer Immunol Immunother. 26(3):215-21 (1988).
Kawamura et al., "Expression of *Escherichia coli* uracil phosphoribosyltransferase gene in murine colon carcinoma cells augments the antitumoral effect of 5-fluorouracil and induces protective immunity," Cancer Gene Ther. 7(4):637-43 (2000).
Kelkar et al., "Antitumor activity of lactic acid bacteria on a solid fibrosarcoma, sarcoma-180 and Ehrlich ascites carcinoma, " Cancer Lett. 42(1-2):73-7 (1988).

(56) References Cited

OTHER PUBLICATIONS

Ketlinsky et al., "[Mechanism of the anti-tumoral effect of the blastolysin fraction isolated from *Lactobacillus bulgaricus*]," Vopr Onkol. 33(3):51-6 (1987) [Article in Russian].
Kimura et al., "Selective localization and growth of *Bifidobacterium bifidum* in mouse tumors following intravenous administration," Cancer Res. 40(6):2061-8 (1980).
Kohwi et al., "Antitumor effect of *Bifidobacterium infantis* in mice," Gann. 69(5):613-8 (1978).
Kokkinakis et al., "Effect of long-term depletion of plasma methionine on the growth and survival of human brain tumor xenografts in athymic mice," Nutr Cancer. 29(3):195-204 (1997).
Kopylova-Sviridova et al., "Transient expression assay in a baculovirus system using firefly luciferase gene as a reporter," Virus Genes. 6(4):379-86 (1992).
Koyama et al., "Combined suicide gene therapy for human colon cancer cells using adenovirus-mediated transfer of *scherichia coli* cytosine deaminase gene and *Escherichia coli* uracil phosphoribosyltransferase gene with 5-fluorocytosine," Cancer Gene Ther. 7(7):1015-22 (2000).
Kunik et al., "Genetic transformation of HeLa cells by *Agrobacterium*," Proc Natl Acad Sci U S A. 98(4):1871-6 (2001).
Lachmann, R.H. and S. Efstathiou, "Gene transfer with herpes simplex vectors," Curr Opin Mol Ther. 1(5):622-32 (1999).
Lamensans et al., "Enhancement of immunity against murine syngeneic tumors by a fraction extracted from non-pathogenic mycobacteria," Proc Natl Acad Sci U S A. 72(9):3656-60 (1975).
Lammertyn et al., "Evaluation of a novel subtilisin inhibitor gene and mutant derivatives for the expression and secretion of mouse tumor necrosis factor alpha by *Streptomyces lividans*," Appl Environ Microbiol. 63(5):1808-13 (1997).
Li et al., "Enzyme/prodrug gene therapy approach for breast cancer using a recombinant adenovirus expressing *Escherichia coli* cytosine deaminase," Cancer Gene Ther. 4(2):113-7 (1997).
Liu et al., "Anticancer efficacy of systemically delivered anaerobic bacteria as gene therapy vectors targeting tumor hypoxia/necrosis," Gene Ther. 9(4):291-6 (2002).
Martino et al., "Bacteremia due to glucose non-fermenting gram-negative bacilli in patients with hematological neoplasias and solid tumors," Eur J Clin Microbiol Infect Dis. 15 (7):610-5 (1996).
McIntosh et al., "A probiotic strain of *L. acidophilus* reduces DMH-induced large intestinal tumors in male Sprague-Dawley rats," Nutr Cancer. 35(2):153-9 (1999).
Meadows et al., "Some biological properties and an in vivo evaluation of tyrosine phenol-lyase on growth of B-16 melanoma," Cancer Res. 36(1):167-7 (1976).
Meck et al., "A virus-directed enzyme prodrug therapy approach to purging neuroblastoma cells from hematopoietic cells using adenovirus encoding rabbit carboxylesterase and CPT-11," Cancer Res. 61(13):5083-9 (2001).
Micheau et al., "Sensitization of cancer cells treated with cytotoxic drugs to fas-mediated cytotoxicity," J Natl Cancer Inst. 89(11):783-9 (1997).
Michl et al., "Claudin-4: a new target for pancreatic cancer treatment using *Clostridium perfringens* enterotoxin," Gastroenterology 121(3):678-84 (2001).
Miki et al., "Methioninase gene therapy of human cancer cells is synergistic with recombinant methioninase treatment," Cancer Res. 60(10):2696-702 (2000).
Milbrandt, E., "A novel source of enterococcal endocarditis," Clin Cardiol. 21(2):123-6 (1998).
Minton et al., "Chemotherapeutic tumour targeting using clostridial spores," FEMS Microbiol Rev. 17(3):357-64 (1995).
Mirzadeh et al., "Radiometal labeling of immunoproteins: covalent linkage of 2-(4-isothiocyanatobenzyl)diethylnetriaminepentaacetic acid ligands to immunoglobulin," Bioconjug Chem. 1(1):59-65 (1990).
Mizutani, T and T. Mitsuoka, "Inhibitory effect of some intestinal bacteria on liver tumorigenesis in gnotobiotic C3H/He male mice," Cancer Lett. 11(2):89-95 (1980).

Mizutani et al., "Doxorubicin sensitizes human bladder carcinoma cells to Fas-mediated cytotoxicity," Cancer. 79(6):1180-9 (1997).
Mizutani et al., "Sensitization of human bladder cancer cells to Fas-mediated cytotoxicity by cis-diamminedichloroplatinum (II)," J Urol. 160(2):561-70 (1998).
Mohr et al., "Rabbit cytochrome P450 4B1: A novel prodrug activating gene for pharmacogene therapy of hepatocellular carcinoma," Cancer Gene Ther. 7(7):1008-14 (2000).
Moolten, F.L., "Tumor chemosensitivity conferred by inserted herpes thymidine kinase genes: paradigm for a prospective cancer control strategy," Cancer Res. 46(10):5276-81 (1986).
Mukherjee et al., "Replication-restricted vaccinia as a cytokine gene therapy vector in cancer: persistent transgene expression despite antibody generation," Cancer Gene Ther. 7(5):663-70 (2000).
Murosaki et al., "Antitumor effect of heat-killed *Lactobacillus plantarum* L-137 through restoration of impaired interleukin-12 production in tumor-bearing mice," Cancer Immunol Immunother. 49(3):157-64 (2000).
Myklebust et al., "Eradication of small cell lung cancer cells from human bone marrow with immunotoxins," Cancer Res. 53(16):3784-8 (1993).
Nakamura et al., "Induction of apoptosis in HL60 leukemic cells by anticancer drugs in combination with anti-Fas monoclonal antibody," Anticancer Res. 17(1A):173-9 (1997).
Nakao, H. and T. Takeda, "*Escherichia coli* Shiga toxin," J Nat Toxins. 9(3):299-313 (2000).
Nauciel, C. and A.F. Goguel, "Inhibition of tumor growth by the peptidoglycan from *Bacillus megaterium*," J Natl Cancer Inst. 59(6):1723-6 (1977).
Nuyts et al., "*Clostridium* spores for tumor-specific drug delivery," Anticancer Drugs. 13(2):115-25 (2002).
O'Brien et al., "Shiga toxin: biochemistry, genetics, mode of action, and role in pathogenesis," Curr Top Microbiol Immunol. 180:65-94'(1992).
O'Mahony et al., "Probiotic impact on microbial flora, inflammation and tumour development in IL-10, knockout mice," Aliment Pharmacol Ther. 15(8):1219-25 (2001).
Paul et al., "Redirected cellular cytotoxicity by infection of effector cells with a recombinant vaccinia virus encoding a tumor-specific monoclonal antibody," Cancer Gene Ther. 7(4):615-23 (2000).
Pawelek et al., "Tumor-targeted *Salmonella* as a novel anticancer vector," Cancer Res. 57(20):4537-4544 (1997).
Pekhov AA, Zhukova OS, Ivanova TP, Zanin VA, Dobrynin IaV. [Cytotoxic effect of methionine-gamma-lyase on neoplastic cells in culture] Biull Eksp Biol Med. 95(5):87-8 (1983) [Article in Russian].
Picot et al., "*Pseudomonas fluorescens* as a potential pathogen: adherence to nerve cells," Microbes Infect. 3(12):985-95 (2001).
Rezmer et al., "Identification and localization of transformed cells in *Agrobacterium tumefaciens*-induced plant tumors," Planta. 209(4):399-405 (1999).
Saito, H. and T. Watanabe T., "Effects of a bacteriocin from *Mycobacterium smegmatis* on BALB/3T3 and simian virus 40-transformed BALB/c mouse cells," Microbiol Immunol. 25(1):13-22 (1981).
Schempp et al., "Inhibition of tumour cell growth by hyperforin, a novel anticancer drug from St. John's wort that acts by induction of apoptosis," Oncogene 21(8):1242-50 (2002).
Schirrmacher et al., "Antitumor effects of Newcastle Disease Virus in vivo: local versus systemic effects," Int J Oncol. 18(5):945-52 (2001).
Schoen et al., "Bacterial delivery of functional messenger RNA to mammalian cells," Cell Microbiol. 7(5):709-24 (2005).
Schroder, J.M., "Epithelial antimicrobial peptides: innate local host response elements," Cell Mol Life Sci. 56(1-2):32-46 (1999).
Schuller et al., "Investigation and management of *Clostridium difficile* colonisation in a paediatric oncology unit.," Arch Dis Child. 72(3):219-222 (1995).
Sekine et al., "Analysis of antitumor properties of effector cells stimulated with a cell wall preparation (WPG) of *Bifidobacterium infantis*," Biol Pharm Bull. 18(1):148-53 (1995).
Sekine et al., "A new morphologically characterized cell wall preparation (whole peptidoglycan) from *Bifidobacterium infantis* with a higher efficacy on the regression of an established tumor in mice," Cancer Res. 45(3):1300-7 (1985).

(56) References Cited

OTHER PUBLICATIONS

Sharma et al., "Death the Fas way: regulation and pathophysiology of CD95 and its ligand," Pharmacol Ther. 88(3):333-47 (2000).
Shimizu et al, "Significance of priming of hosts with virus in the tumor-specific immunotherapy model utilizing virus-reactive helper T cell activity," Nippon Gan Chiryo Gakkai Shi. May 20, 1989;24(5):1007-14. [Article in Japanese].
Shimizu et al., "Immunotherapy of tumor-bearing mice utilizing virus help," Cancer Immunol Immunother. 27(3):223-7 (1988).
Simon et al., "Surveillance for nosocomial and central line-related infections among pediatric hematology-oncology patients," Infect Control Hosp Epidemiol. 21(9):592-6 (2000).
Simonds et al., "Deoxyribonucleic acid hybridization among strains of *Lactobacilli*," J Bacteriol. 107(1):382-4 (1971).
Sivanandham et al., "Colon cancer cell vaccine prepared with replication-deficient vaccinia viruses encoding B7.1 and interleukin-2 induce antitumor response in syngeneic mice," Cancer Immunol Immunother 46(5):261-7 (1998).
Smyth et al., "Bovine enterovirus as an oncolytic virus: foetal calf serum facilitates its infection of human cells," Int J Mol Med. 10(1):49-53 (2002).
Soby et al., "Catabolite-repressor-like protein regulates the expression of a gene under the control of the *Escherichia coli* lac promoter in the plant pathogen *Xanthomonas campestris* pv. *campestris*," Appl Microbiol Biotechnol. 46(5-6):559-61 (1996).
Spooner et al., "In suicide gene therapy, the site of subcellular localization of the activating enzyme is more important than the rate at which it activates prodrug," Cancer Gene Ther. 7(10):1348-56 (2000).
Steffens et al., "Enhanced green fluorescent protein fusion proteins of herpes simplex virus type 1 thymidine kinase and cytochrome P450 4B1: applications for prodrug-activating gene therapy," Cancer Gene Ther. 7(5):806-12 (2000).
Tanaka et al, "Preliminary evaluation of intratumoral injection of a *Streptococcus pyogenes* preparation in patients with malignant brain tumors," Cancer 46(7):1688-94 (1980).
Tartaglia et al., "NYVAC: a highly attenuated strain of vaccinia virus," Virology 188(1):217-32 (1992).
Thatcher et al., "The potential of acetaminophen as a prodrug in gene-directed enzyme prodrug therapy," Cancer Gene Ther. 7(4):521-5 (2000).
Theys et al., "Specific targeting of cytosine deaminase to solid tumors by engineered *Clostridium acetobutylicum*," Cancer Gene Ther. 8(4):294-7 (2001).
Theys et al., "Stable *Escherichia coli-Clostridium acetobutylicum* shuttle vector for secretion of murine tumor necrosis factor alpha," Appl Environ Microbiol. 65(10):4295-4300 (1999).
Tietze et al., "Highly selective glycosylated prodrugs of cytostatic CC-1065 analogues for antibody-directed enzyme tumor therapy," Chembiochem. 2(10):758-65 (2001).
Timiryasova et al., "Radiation enhances the anti-tumor effects of vaccinia-p53 gene therapy in glioma," Technol Cancer Res Treat. 2(3):223-35 (2003).
Toso et al, "Phase I study of the intravenous administration of attenuated *Salmonella typhimurium* to patients with metastatic melanoma," J Clin Oncol. 20(1):142-52 (2002).
Ullrich C.I. and R. Aloni, "Vascularization is a general requirement for growth of plant and animal tumours," Journal of Experimental Botany 51(353):1951-60 (2000).
Webley et al., "Measurement of the critical DNA lesions produced by antibody-directed enzyme prodrug therapy (ADEPT) in vitro, in vivo and in clinical material," Br J Cancer. 84(12):1671-6 (2001).
Weedon et al., "Sensitisation of human carcinoma cells to the prodrug CB1954 by adenovirus vector-mediated expression of *E. coli* nitroreductase," Int J Cancer. 86(6):848-54 (2000).
Wehl et al., "Trends in infection morbidity in a pediatric oncology ward, 1986-1995," Med Pediatr Oncol. 32(5):336-43 (1999).
Westphal et al., "The nitroreductase/CB1954 combination in Epstein-Barr virus-positive B-cell lines: induction of bystander killing in vitro and in vivo," Cancer Gene Ther. 7(1):97-106 (2000).
Wollowski et al., "Protective role of probiotics and prebiotics in colon cancer," Am J Clin Nutr. 73 (2 Suppl):451S-455S (2001).
Wu et al., "Biological purging of breast cancer cells using an attenuated replication-competent herpes simplex virus in human hematopoietic stem cell transplantation," Cancer Res. 61(7):3009-15 (2001).
Yamamoto et al., "Production of L-forms of *Streptococcus pyogenes* and their antitumor effects," Jpn J Exp Med. 50(5):383-8 (1980).
Yazawa et al., "*Bifidobacterium longum* as a delivery system for cancer gene therapy: Selective localization and growth in hypoxic tumors," Cancer Gene Ther. 7(2):269-74 (2000).
Yazawa et al., *Bifidobacterium longum* as a delivery system for gene therapy of chemically induced rat mammary tumors. Breast Cancer Res Treat. 66(2):165-70 (2001).
Yu et al., . Visualization of tumors and metastases in live animals with bacteria and vaccinia virus encoding light-emitting proteins, Nature Biotechnology 22(3):313-320 (2004).
Zambryski et al., "Tumor induction by *Agrobacterium tumefaciens*: analysis of the boundaries of T-DNA," J Mol Appl Genet. 1(4):361-70 (1982).
Zheng et al., "Tumor amplified protein expression therapy: *Salmonella* as a tumor-selective protein delivery vector," Oncology Research 12(3):127-135 (2000).
zur Hausen, H., Papillomaviruses and cancer: from basic studies to clinical application. Nature Reviews Cancer 2(5):342-50 (2002).
"WHO Collaborating Centre for Orthopoxvirus Diagnosis and Repository for Variola Virus Strains and DNA," VECTOR: Ministry of Public Health and Social Development of Russian Federation, State Research Center of Virology and Biotechnology http://www.vector.nsc.ru/DesktopDefault.aspx?lcid=9&tabid=294&tabindex=1 (accessed on Sep. 12, 2005).
"A New Way to Kill Cancer: SLU Research Shows Viruses can destroy lung, colon tumors," Science Daily: Your link to the latest research news http://www.sciencedaily.com./releases/2004/05/040517071951.htm (accessed on May 17, 2004).
Advani et al., "Replication-competent, Nonneuroinvasive Genetically Engineered Herpes Virus Is Highly Effective in the Treatment of Therapy-resistant Experimental Human Tumors," Cancer Research 59: 2055-2058 (1999).
Altenbrunn et al., "Scintographic Tumor Localization in Mice with Radioiodinated Anti-*Clostridium* Antibodies," Int. J. Nucl. Med. Biol. 8(1): 90-93 (1981).
Bennett et al., "Positron emission tomography imaging for herpes virus infection: Implications for oncolytic viral treatments of cancer," Nature Med 7(7): 859-863 (2001).
Berger, F. and S.S. Gambhir, "Recent advances in imaging endogenous or transferred gene expression utilizing radionuclide technologies in living subjects," Breast Cancer Research 3: 28-35 (2001).
Blasberg, R.G. and J.G. Tjuvajev, "Herpes simplex virus thymidine kinase as a marker/reporter gene for PET imaging of gene therapy," Q J Nucl Med 43(2): 163-169 (1999).
Boland et al., "Adenovirus-mediated Transfer of the Thyroid Sodium/Iodide Symporter Gene into Tumors for a Targeted Radiotherapy," Cancer Research 60: 3484-3492 (2000).
Bonnekoh et al., "Adenoviral-Mediated Herpes Simplex Virus-Thymidine Kinase Gene Transfer in Vivo for Treatment of Experimental Human Melanoma," J .Invest. Dermatol. 106(6): 1163-1168 (1996).
Brockstedt et al., "Development of Anti-tumor Immunity against a Non-immunogenic Mammary Carcinoma through in Vivo Somatic GM-CSF, IL-2, and HSVtk Combination Gene Therapy," Mol. Ther. 6(5): 627-636 (2002).
Certified English translation of abstract for Aksac S., "[Antibody formation against *Agrobacterium tumefaciens* in patients with various cancers]," Turk Hij Tecr Biyol Derg. 34(1-2):48-51 (1974) [Article in Italian].
Certified English translation of journal article for Al'tshtein [Altshteyn] et al., "[Isolation of a recombinant vaccinia virus based on the LIVP strain inducing the surface antigen of the hepatitis B virus]," Dokl Akad Nauk SSSR. 285(3):696-9 (1985) [Article in Russian].

(56) References Cited

OTHER PUBLICATIONS

Chaudhuri et al., "Light-based imaging of green fluorescent protein-positive ovarian cancer xenografts during therapy," Gynecol. Oncol. 82(3): 581-589 (2001).

Derwent English abstract for Japanese Patent Publication JP 55035004, published Feb. 3, 1987, entitled, "Cellular immuno-potentiator—contg. Vaccinia attenuated virus showing no infectivity to man or rabbit and has lost humoral immunity," Derwent Accession No. 2512008.

Fabricius et al., "Quantitative investigations into the elimination of in vitro-obtained spores of the non-pathogenic *Clostridium butyricum* strain CNRZ 528, and their persistence in organs of different species following intravenous spore administration," Res. Microbiol. 144: 741-753 (1993).
Francis et al., "Monitoring bioluminescent *Staphyloccus aureus* infections in living mice using a novel *lux*ABCDE construct," Infection and Immunity 68(6): 3594-3600 (2000).
Gambhir et al., "Imaging transgene expression with radionuclide imaging technologies," Neoplasia 2(1-2): 118-138 (2000).
Gnant et al., "Regional Versus Systemic Delivery of Recombinant Vaccinia Virus as Suicide Gene Therapy for Murine Liver Metastases," Annals of Surgery 230(3): 352-361 (1999).
Gnant et al., "Sensitization of tumor necrosis factor α-resistant human melanoma by tumor-specific in vivo transfer of the gene encoding endothelial monocyte-activating polypeptide II using recombinant vaccinia virus," Cancer Research 59: 4668-4674 (1999).
Hamblin et al., "Rapid control of wound infections by targeted photodynamic therapy monitored by in vivo bioluminescence imaging," Photochemistry and Photobiology 75(1): 51-57 (2002).
Hansen et al., "Assessment of GFP fluorescence in cells of *Streptococcus gordonii* under conditions of low pH and low oxygen concentration," Microbiology 147: 1383-1391 (2001).
Hasegawa et al., "In vivo tumor delivery of the green fluorescent protein gene to report future occurrence of metastasis," Cancer Gene Therapy 7: 1336-1340 (2000).
Hiller et al., "Characterization of Intracellular and Extracellular Vaccinia Virus Variants: $N_1$-Isonicotinoyl-$N_2$-3-Methyl-4-Chlorobenzoylhydrazine Interferes with Cytoplasmic Virus Dissemination and Release," Journal of Virology 39(3): 903-913 (1981).
lanaro et al., "Expression of TGF-β in attenuated *Salmonella typhimurium*: oral administration leads to the reduction of inflammation, II-2 and IFN-γ, but enhancement of IL-10, in carrageein-induced oedema in mice," Immunology 84:8-15 (1995).
Jacobs et al., "Positron Emission Tomography-based Imaging of Transgene Expression Mediated by Replication-conditional, Oncolytic Herpes Simplex Virus Type I Mutant Vectors in Vivo," Cancer Research 61: 2983-2995 (2001).
Jain, R.K. and N.S. Forbes, "Can engineered bacteria help control cancer," Proc. Natl. Acad. Sci. USA 98(26): 14748-14750 (2001).
Joklik, W.K., "The Purification of Four Strains of Poxviruses," Virology 18:9-18 (1962).
Kaplitt et al.,, "Mutant herpes simplex virus induced regression of tumors growing in immunocompetent rats," J. Neurooncol 19(2): 137-147 (1994).
Kirn, D.H. and F. McCormick, "Replicating viruses as selective cancer therapeutics," Mol Med Today 2(12): 519-527 (1996).
Kutinova et al., "Search for optimal parent for recombinant vaccinia virus vaccines. Study of three vaccinia virus vaccinal strains and several virus lines derived from them," Vaccine 13(5): 487-493 (1995).
Lattime et al., "In Situ Cytokine Gene Transfection Using Vaccinia Virus Vectors," Semin Oncol 23(1): 88-100 (1996).
Mackenzie et al., "Human mesenchymal stem cells persist, demonstrate site-specific multipotential differentiation, and are present in sites of wound healing and tissue regeneration after transplantation into fetal sheep," Blood Cells, Molecules, and Diseases 27(3): 601-604 (2001).
McCart et al., "Oncolytic Vaccinia Virus Expressing the Human Somatostatin Receptor SSTR2: Molecualr Imaging after Systemic Delivery Using $^{111}$In-Pentetreotide," Molecular Therapy 10(3): 553-61 (2004).
Meyer et al., "Mapping of deletions in the genome of the highly attenuated vaccinia virus MVA and their influence on virulence," Journal of General Virology 72(Pt 5): 1031-1038 (1991).
Muravlev et al., "Protective activity of vaccinia virus envelope proteins isolated with the use of nonionic detergents," Voprosy Virusologii 40(4): 154-8 (1995) ) [article in Russian, English summary on last page of article].
Netesova et al., "Structural and functional studies of the *Hind*III-I-Genome Fragment of Vaccinia virus Strain L-IVP," Mol Biol (Mosk.) Nov.-Dec.; 25(6): 1526-32 (1991) ) [article in Russian, English summary on last page of article].
Norton et al., "Expression of Secreted Platelet-Derived Growth Factor-B by Recombinant Nonreplicating and Noncytopathic Vaccinia Virus," Annals of Surgery 224(4):555-562 (1996).
Overwijk et al., "Vaccination with a recombinant vaccinia virus enclding a 'self' antigen induces autoimmune vitiligo and tumor cell destruction in mice: Requirement for CD4+ T lymphocytes," Proc. Natl. Acad. Sci. USA 96: 2982-2987 (1999).
Pak et al., "Cloning of the growth factor gene from vaccinia virus LIVP strain in *Escherichia coli* cells," Mol Gen Mikrobiol Virusol Sep.-Oct.; (9-10):19-21 (1992) ) [article in Russian, English summary on last page of article].
Pan et al., "Regression of Established B16F10 Melanoma with a Recombinant *Listeria monocytogenes* Vaccine," Cancer Research 59:5264-5269 (1999).
Peplinski et al., "In vivo gene therapy of a murine pancreas tumor with recombinant vaccinia virus encoding human interleukin-1beta," Surgery 118:185-191 (1995).
Phillips-Jones, M.K., "Bioluminescence (*lux*) expression in the anaerobe *Clostridium perfringens*," FEMS Microbiology Letters 106: 265-270 (1993).
Phillips-Jones, M.K., "Use of *lux* reporter system for monitoring rapid changes in α-toxin gene expression in *Clostridium perfringens* during growth," FEMS Microbiology Letters 188: 29-33 (2000).
Poptani et al., "Monitoring thymidine kinase and ganciclovir-induced changes in rat malignant glioma in vivo by nuclear magnetic resonance imaging," Cancer Gene Ther 5(2): 101-109 (1998).
Prikhod'ko, G. G. et al., "Cloning, Sequencing and Translation Analysis of the Vaccinia Virus LIVP HindIII N Fragment," Genetika 27(6): 955-963 (1991) ) [article in Russian, English summary on last page of article].
Prikhod'ko, G. G. and IV Babkin, "5'-variable genome sequence of vaccinia virus LIVP. Possible role of short direct repeats in formation of DNA deletions," Genetika 27(1): 13-26 (1991) [article in Russian, English summary on last page of article].
Qazi et al, "Real-time monitoring of intracellular *Staphylococcus aureus* replication," J Bacteriol. 186(4): 1065-1077 (2004).
Rocchetta et al., "Validation of a Noninvasive, Real-Time Imaging Technology Using Bioluminescent *Escherichia coli* in the Neutropenic Mouse Thigh Model of Infection," Antimicrobial Agents and Chemotherapy 45(1): 129-137 (2001).
Scholl et al., "Recombinant Vaccinia Virus Encoding Human *MUC1* and *IL2* as Immunotherapy in Patients with Breast Cancer," J. Immunother 23(5): 570-580 (2000).
Shchelkunov et al., "The gene encoding the late nonstructural 36K protein of vaccinia virus is essential for virus reproduction," Virus Research 28: 273-283 (1993).
Shimizu et al., "Antitumor activity of marine bacteria, *Vibrio anguillarum*, in mice," Gann 70: 429-433 (1979).
Shimizu et al., "Antitumor activity of 2-keto-3-deoxyoctonate-free lipopolysaccharide of *Vibrio anguillarum* in mice," Gann 74(2): 279-284 (1983).
Studeny et al., "Bone Marrow-derived Mesenchymal Stem Cells as Vehicles for Interferon-β Delivery into Tumors," Cancer Research 62: 3603-3608 (2002).
Thome, S. H. and D. H. Kim, "Future directions for the field of oncolytic virotherapy: a perspective on the use of vaccinia virus," Expert Opin Biol Ther 4(8): 1307-1321 (2004).

(56) References Cited

OTHER PUBLICATIONS

Tjuvajev et al., "Noninvasive Imaging of Herpes Virus Thymidine Kinase Gene Therapy and Expression: A Potential Method for Monitoring Clinical Gene Therapy," Cancer Res 56(18): 4087-4095 (1996).
Tjuvajev et al., "Imaging the Expression of Transfected Genes in Vivo," Cancer Res. 55(24): 6126-6132 (1995).
Tjuvajev et al., "Imaging Adenoviral-mediated Herpes Virus Thymidine Kinase Gene Transfer and Expression in Vivo," Cancer Research 59: 5186-5193 (1999).
Tjuvajev et al., "Imaging Herpes Virus Thymidine Kinase Gene Transfer and Expression by Positron Emission Tomography,"Cancer Res. 58(19): 4333-4341 (1998).
Vogt et al., "Untersuchungen über die Möglichkeit der Tumorlokalisation in vivo auf ser Basis eines szintigrafischer Klostridienstäbchen-Nachweises mit $^{131}$J-markierten Antikörpern and F(ab')$_2$-Antikörperfragmenten," Zeitschrift für Experimentelle Chirurgie 12(4): 209-215 (1979) [article in German, English summary on the last page of the article].
Volm et al., "Enhancement of Incorporation of $^{131}$Iododeoxyuridine into Tumors after Application of *Clostridium oncolyticum s. butyricum* (M 55)," Eur. J. Nuc). Med. 2(2): 117-120 (1977).
Xie et al., "Adenovirus-mediated Tissue-targeted Expression of a Caspase-9-based Artificial Death Switch for the Treatment of Prostate Cancer," Cancer Research 61: 6795-6804 (2001).
Yang et al., "Visualizing gene expression by whole-body fluorescence imaging," PNAS 97(22): 12278-12282 (2000).
Zhao et al., "Spatial-temporal imaging of bacterial infection and antibiotic response in intact animals," Proceeding of the National Academy of Sciences 98(17): 9814-9818 (2001).
Zinoviev et al., "Identification of the gene encoding vaccinia virus immunodominant protein p35," Gene 147: 209-214 (1994).
Chen et al., "Evaluation of Cytokine Toxicity Induced by Vaccinia Virus-mediated IL-2 and IL-2 Antitumor Immunotherapy," Cytokine (2001) 15(61):305-314.
Hatta, "Antitumor Mechanisms of *Eubacterium lentum* and its Components," Asian Pacific Journal of Allergy and Immunology 13: 129-137 (1995).
Morinaga et al., "Antitumor Activity and its Properties of *Eubacterium lentum*," Jpn. J. Cancer Res. (Gann) 79: 117-124 (1988).
Sakamoto et al., "Antitumor Effect of Normal Intestinal Microflora on Ehrlich Ascites Tumor," Jpn. J. Cancer Res. (Gann) 79: 109-116 (1988).
Pace, "Strep Throat," JAMA, 284(22):2964 (2000).
U.S. Appl. No. 10/516,785, filed Jun. 27, 2005.
U.S. Appl. No. 11/238,025, filed Sep. 27, 2005.
Chaloupka, I., et al., "Comparative Analysis of Six European Influenza Vaccinesm," European Journal of Microbiology and Infectious Disease, 15(2):121-127, (1996).
Cioffi, L., et al., "A novel endothelial cell-based gene therapy platform for the in vivo delivery of apolipoprotein E," Gene Therapy, 6:1153-1159, (1999).
Crystal, R.G., "Transfer of Genes to Humans: Early Lessons and Obstacles to Success," Science, 270:404-410, (1995).
Davis, C.G., "The Many Faces of Epidermal Growth Factor Repeats," The New Biologist, 2(5):410-419, (1990).
Deng, W., et al., "Engineering Ex Vivo-Expanded Marrow Stromal Cells to Secrete Calcitonin Gene-Related Peptide Using Adenoviral Vector," Stem Cells, 22:1279-1291, (2004).
Eck et al., "Gene-Based Therapy," *The Pharmacological Basis of Therapeutics*, Ch. 1, Eds., Goodman and Gilman, Macmillan Publishing Co., New York, N.Y., pp. 77-101, (1996).
Gorecki, D., "Prospects and problems of gene therapy: an update," Expert Opinions in Emerging Drugs, 6(2):187-198, (2001).
Kaufman, H., et al., "A recombinant vaccinia virus expressing human carcinoembryonic antigen CEA", International Journal of Cancer, 48(6):900-907, (1991).

Kaufman et al., "Insertion of interleukin-2 (IL-2) and interleukin-12 (IL-12) genes into vaccinia virus results in effective anti-tumor responses without toxicity," Vaccine, 20:1862-1869, (2002).
Kaye F.J., et al., "A single amino acid substitution results in a retinoblastoma protein defective in phosphorylation and oncoprotein binding",Proceedings of the National Academy of Sciences of the United States of America, 87:6922-6926, (1990).
Kutinova, L., et al., "Hepatitis B virus proteins expressed by recombinant vaccinia viruses: influence of preS2 sequence on expression surface and nucleocapsid proteins in human diploid cells," Archives of Virology, 134:1-15, (1994).
Mutschler, E., et al., "10. Chemotherapy of Malignant Tumors,"*Drug Actions: Basic Principles and Therapeutic Aspects*, Medpharm CRC Press, Suttgart, Germany, pp. 595-612, (1995).
Parrish, E.P., et al., "Targeting widespread sites of damage in dystrophic muscle: engrafted macrophages as potential shuttles," Gene Therapy, 3:13-20, (1996).
Perkus, M., et al., "Recombinant Vaccinia Virus: Immunization Against Multiple Pathogens," Science, 229(4717):981-984, (1985).
Pfleiderer, M., et al., "A novel vaccinia virus expression system allowing construction of recombinants without the need for selection markers, plasmids and bacterial hosts," Journal of General Virology, 76:2957-2962, (1995).
Rudinger, J., "Characteristics of the amino acids as components of a peptide hormone sequence", *Peptide Hormones*, Ed., J.A. Parsons, University Park Press, Baltimore, p. 1-7, (1976).
Sivanandham, M. et al., "Therapeutic effect of a vaccinia colon oncolysate prepared with interleukin-2-gene encoded vaccinia virus studied in a syngeneic CC-36 murine colon hepatic metastasis model," Cancer Immunological Immunotherapy, 38:259-264, (1994).
Skolnick, J., et al., "From genes to protein structure and function: novel applications of computational approaches in the genomic era," Trends in Biotechnology, 18:34-39, (2000).
Torrente, Y., et al. "Intraarterial injection of muscle-derived CD34+Sca-1+ stem cells restores dystrophin in mdx mice," Journal of Cellular Biology, 152(2):335-348, (2001).
Van Damme, A., et al., "Bone marrow stromal cells as targets for gene therapy," Current Gene Therapy, 2:195-209, (2002).
Verma, I, et al., "Gene therapy—promises, problems and prospects," Nature, 389:239-242, (1997).
Williams, R. Senders, "Southwestern Internal Medicine Conference: Prospects for Gene Therapy of Ischemic Heart Disease," The American Journal of the Medical Sciences, 306(2):129-136, (1993).
Bevis, B. and B. Glick, "Rapidly maturing variants of the Discoma red fluorescent protein (DsRed)," Nat. Biotechnol. 20:83-87 (2002).
Certified English translation of Chernos et al., "Tests for safety, 'Take'—Rate, Reactogenicity and Antigenic Properties of a Live Recombinant Smallpox-Hepatitis B Vaccine in Volunteers," Vopr. Virusol. (Moscow) 35:132-135 (1990).
Chen, Y., "Orthopedic applications of gene therapy," J Orthop Sci 6:199-207 (2001).
Chernos et al., "Tests for safety, 'Take'—Rate, Reactogenicity and Antigenic Properties of a Live Recombinant Smallpox-Hepatitis B Vaccine in Volunteers", Vopr. Virusol. (Moscow) 35:132-135 (1990). [article in the Russian language].
Chkheidze et al., "Identification of DNA binding proteins in vaccinia virus by DNA-protein crosslinking," FEBS 336(2):340-342 (1993).
Conry et al., Phase I trial of a recombinant vaccinia virus encoding carcinoembryonic antigen in metastatic adenocarcinoma: comparison of intradermal versus subcutaneous administration. Clin Cancer Res 5:2330-2337 (1999).
de Wet et al., "Firefly Luciferase Gene: Structure and Expression in Mammalian Cells," Mol. Cell. Biol. 7: 725-737 (1987).
Demkowicz et al., "Human Cytotoxic T-Cell Memory: Long-Lived Responses to Vaccinia Virus," J. Virol. 70(4):2627-2631 (1996).
Earl et al., "T-lymphocyte priming and protection against Friend leukemia by vaccinia-retrovirus env gene recombinant," Science 234:728-831 (1986).
Giavedoni et al., "Vaccinia virus recombinants expressing chimeric proteins of human immunodeficiency virus and gamma-interferon are attenuated for nude mice" Proc. Natl. Acad. Sci. 89:3409-3413 (1992).

(56) References Cited

OTHER PUBLICATIONS

Hall, F., et al., "Targeting retroviral vectors to vascular lesions by genetic engineering of the MoMLV gp70 envelope protein," Human Gene Therapy, 8:2183-2192 (1997).
Hauser et al., "Poxvirus as a vector to transduce human dendritic cells for immunotherapy: abortive infection but reduced APC function," Gene Ther. 7(18):1575-1583 (2000).
Heise et al., "Efficacy of a replication-competent adenovirus (ONYX-015) following intratumoral injection: intratumoral spread and distribution effects," Cancer Gene Ther. 6(6):499-504 (1999).
Hodge et al., "Induction of antitumor immunity by recombinant vaccinia viruses expressing B7-1 or B7-2 costimulatory molecules," Cancer Res. 54(21):5552-5555 (1994).
Ikeda et al., "Oncolytic virus therapy of multiple tumors in the brain requires suppression of innate and elicited antiviral responses," Nat Med. Aug.;5(8):881-887 (1999).
Kass et al, "Induction of protective host immunity to carcinoembryonic antigen (CEA), a self-antigen in CEA transgenic mice, by immunizing with a recombinant vaccinia-CEA virus," Cancer Research 59:676-683 (1999).
Kaufman et al., "A phase I trial of intra lesional RV-B7.1 vaccine in the treatment of malignant melanoma" Hum. Gene Ther. 11(7):1065-1082 (2000).
Kaufman et al., "A recombinant vaccinia virus expressing human carcinoembryonic antigen CEA," International Journal of Cancer 48(6):900-907 (1991).
Kim et al., "Replication-selective virotherapy for cancer: biological principles, risk management and future directions," Nat. Med. 7:781-787 (2001).
Lane et al., "Complications of smallpox vaccination, 1968: results of ten statewide surveys," J Infect Dis 122:303-309 (1970).
Lane et al., "Complications of smallpox vaccinations, 1968: national surveillance in the United States," New Engl J Med 281:1201-1208 (1969).
Larocca et al., "Gene Transfer to Mammalian Cells Using Genetically Targeted Filamentous Bacteriophage," FASEB Journal 13:727-734 (1999).
Martinez et al., "Specific Antibody to *Cryptococcus neoformans* Glucurunoxylomannan Antagonizes Antifungal Drug Action against Cryptococcal Biofilms in Vitro," J. Infect. Diseases 194:261-266 (2006).
Mastrangelo et al., "Intratumoral recombinant GM-CSF-encoding virus as gene therapy in patients with cutaneous melanoma," Cancer Gene Ther. 6(5):409-422 (1998).
Moss, B., "Genetically engineered poxviruses for recombinant gene expression, vaccination, and safety," Proc Natl Acad Sci USA. 93:11341-11348 (1996).
Okada et al., "Sensitization of human tumor cells to homologous complement by vaccinia virus treatment" Cancer Irnmunol Immunother 25(1):7-9 (1987).
Okuse et al., "Enhancement of antiviral activity against hepatitis C virus in vitro by interferon combination therapy," Antiviral Research 65:23-34 (2005).
Orkin et al., "Report and Recommendations of the Panel to Assess the NIH Investment in Research on Gene Therapy," (1995).
Paoletti et al., "Applications of pox virus vectors to vaccination: An update, "Proc. Natl. Acad. Sci. 93:11349-11353 (1996).
Peplinski et al., "Prevention of murine breast cancer by vaccination with tumor cells modified by cytokine-producing recombinant vaccinia viruses," Annals Surg. Oncol. 3(1):15-23 (1996).
Perkus et al., "Deletion of 55 open reading frames from the termini of vaccinia virus", Virology 180:406-410 (1991).
Qin, H. and S. Chatterjee, "Construction of recombinant vaccinia virus expressing GM-CSF and its use as a tumor vaccine," Gene Ther. 3(1):59-66 (1996).
Ramirez el al., "Biology of attenuated modified vaccinia virus Ankara recombinant vector in mice: Virus fate and activation of B- and T-Cell immune responses in comparsion with the Western Reserve Strain and advantages as a vaccine," J. Virol. 74(2):923-933 (2000).
Roenigk et al., "Immunotherapy of malignant melanoma with vaccinia virus," Arch Dermatol 109:668-673 (1977).
Shida et al., "Effects and virulences of recombinant vaccinia viruses derived from attenuated strains that express the human T-cell leukemia virus type I envelope gene," J. Virol. 62(12):4474-4480 (1988).
Smith et al. "Immune response to poxvirus infections in various animals" Crit. Rev. Microbiol. 28(3):149-185 (2002).
Smith et al., "Host range selection of vaccinia recombinants containing insertions of foreign genes into non-coding sequences" Vaccine. 11(1):43-53 (1993).
Sroller et al., "Effect of 3-beta-hydroxysteroid dehydrogenase gene deletion on virulence and immunogenicity of different vaccinia viruses and their recombinants," Arch. Virol. 143:1311-1320 (1998).
Steele, T., "Recent developments in the Virus therapy of Cancer," Proceedings of the Society for Experimental Biology and Medicine 223:118-127 (2000).
Stienlauf et al., "Kinetics of formation of neutralizing antibodies against vaccinia virus following re-vaccination,"Vaccine 17:201-204 (1999).
Sui et al., "Cell Cycle-Dependent Antagonistic Interactions between Paclitaxel and gamma-Radiation in Combination Therapy," Clin. Canc. Res. 10:4848-4857 (2004).
Taylor et al., "Comparison of the virulence of wild-type thymidine kinase (tk)-deficient and tk+ phenotypes of vaccinia virus recombinants after intranasal inoculation of mice," J. Gen. Virol. 72 (Pt 1):125-130 (1991).
Weissleder et al., "In vivo imaging of tumors with protease-activated near-infrared fluorescent probes," Nature Biotech. 17:375-378 (1999).
Xiong et al., "Cell cycle dependent antagonistic interactions between Paclitaxel and Carboplatin in combination therapy," Cancer Biology Therapy 6(7): 1067-1073 (2007).
Yettra M., "Remission of chronic lymphocytic leukemia after smallpox vaccination," Arch Intern Med. 139(5):603 (1979).
Fox et al., "Anaerobic bacteria as a delivery system for cancer gene therapy: in vitro activation of 5-fluorocytosine by genetically engineered clostridia," Gene Therapy, 3(2):173-178, (1996).
Fox et al., Erratum to "Anaerobic bacteria as a delivery system for cancer gene therapy: in vitro activation of 5-fluorocytosine by genetically engineered clostridia," Gene Therapy, 3(8):741 (1996).
Kohler et al., "Continuous cultures of fused cells secreting antibody of predefined specificity," Nature, 256:495-497, (1975).
Lindsey et al., "Modified cold virus kills colon cancer," Lancet Oncology, 3(5):264, (2002).
Lutz et al., "Independent and tight regulation of transcriptional units in *Escherichia coli* via the LacR/O, the TetR/O and AraC/I$_1$-I$_2$ regulatory elements," Nucleic Acids Research, 25:1203-1210, (1997).
Mikryukov et al., "Structural-functional organization of segment of vaccinia virus genome," Soviet Biotechnology (Biotekhnologiya), 4: 19-25, (1988) [corresponds to pp. 442-449 in the Russian language edition].
Moats et al., "A 'smart' magnetic resonance imaging agent that reports on specific enzymatic activity," Angewandte Chemie, 36(7):726-728, (1997).
Wahl et al., "Improved Radioimaging and tumor localization with monoclonal F(ab')$_2$," Journal of Nuclear Medicine, 24:316-325, (1983).
Office Action, issued Oct. 8, 2009, in connection with Japanese Patent Application No. 2003-519509.
Office Action, issued Feb. 4, 2013, in connection with corresponding Chinese Patent Application No. 200810130048.9, 6 pages. [in Chinese with English translation provided].
Chattopadhyay et al., "Effect of single amino acid mutations in the conserved GDNQ motif of L protein of Rinderpest virus on RNA synthesis in vitro and in vivo," Virus Res. 99:139-145 (2004).
John et al., "In vitro and in vivo analyses of constitutive and in vivo-induced promoters in attenuated vaccine and vector strains of *Vibrio cholerae*," Infect. Immun. 68(3):1171-1175 (2000).
Meighen, E., "Bacterial bioluminescence: organization, regulation, and application of the lux genes," FASEB J. 7:1016-1022 (1993).
Peplinsky et al., "In vivo murine tumor gene delivery and expression by systemic recombinant vaccinia virus encoding interleukin-1 beta," Cancer J. Sci. Am. 2(1):21-27 (1996).

(56) References Cited

OTHER PUBLICATIONS

Sandman et al., "Rapid fluorescence-based reporter-gene assays to evaluate the cytotoxicity and antitumor drug potential of platinum complexes," Chem. Biol. 6:541-551 (1999).
Smallwood et al., "Different substitutions at conserved amino acids in domains II and III in the Sendai L RNA polymerase protein inactivate viral RNA synthesis," Virol. 304:135-145 (2002).
Toyoizumi et al., "Combined therapy with chemotherapeutic agents and herpes simplex virus type I ICP34.5 mutant (HSV-1716) in human non-small cell lung cancer," Human Gene Ther. 10:3013-3029 (1990).
Zhu et al., "A cellular protein binds vaccinia virus late promoters and activates transcription in vitro," J. Virol. 72(5):3893-3899 (1998).
Advani et al., "Radiotargeting systemically administered oncolytic vaccinia virus to preferentially replicate in radiated gliomas," Abstract, ASTRO 53rd Annual Meeting, Miami Beach, FL, Oct. 2-6, 2011 [2 pages].
Gentschev et al., "Regression of human prostate tumors and metastases in nude mice following treatment with the recombinant oncolytic vaccinia virus GLV-1h68," J. Biomed. Biotechnol. 2010:1-11 (2010).
Hoffman et al., "Vaccinia virus GLV-1h237 carrying a Walker A motif mutation of mouse Cdc6 protein enhances human breast tumor therapy in mouse xenografts," Int. J. Oncol. 38(3):871-878 (2011) [Published online Jan. 18, 2011].
Seubert et al., "Enhanced tumor therapy using vaccinia virus strain GLV-1h68 in combination with a β-galactosidase-activatable prodrug seco-analog of duocarmycin SA," Cancer Gene Ther. 18:42-52 (2011).
Zhang et al., "The highly attenuated oncolytic recombinant vaccinia virus GLV-1h68: comparitive genomic features and the contribution of F14.5L inactivation," Mol. Genet. Genomics 282(4):417-435 (2009).
Search Report and Written Opinion, issued Dec. 22, 2009, in connection with corresponding Singapore Patent Application No. 200602906-0.
Office Action, issued Apr. 8, 2010, in connection with related U.S. Appl. No. 12/218,953.
Office Action, issued May 28, 2010, in connection with corresponding Canadian Patent Application No. 2,456,055.
Office Action, issued Nov. 2, 2010, in connection with corresponding U.S. Appl. No. 10/866,606.
Examination Report, issued Dec. 7, 2010, in connection with corresponding Singapore Patent Application No. 200602906-0.
Office Action, issued Jan. 13, 2011, in connection with related U.S. Appl. No. 12/218,953.
Bischoff et al., "An adenovirus mutant that replicates selectively in p53-deficient human tumor cells," Science 274 (5286):373-376 (1996).
Buller et al., In: "Vaccinia Viruses as Vectors for Vaccine Antigens," New York: Elsevier, Quinnan, G.V. ed., pp. 37-46 (1985).
Casado et al, "Strategies to accomplish targeted expression of transgenes in ovarian cancer for molecular therapeutic applications," Clin. Cancer Res. 7(8):2496-2504 (2001).
Coupar et al., "Insertion sites for recombinant vaccinia virus construction: effects on expression of a foreign protein," J. Gen. Virol. 81:431-439 (2000).
DiStefano et al., "Viral-induced remission in chronic lymphocytic leukemia?" Arch. Intern. Med. 139(8):946 (1979).
Enserink M., "Treating vaccine reactions: two lifelines, but no guarantees," Science 298(5602):2313 (2002).
Etoh et al., "Oncolytic viral therapy for human pancreatic cancer cells by reovirus," Clin. Cancer Res. 9:1218-1223 (2003).
Galmiche et al., "Expression of a functional single chain antibody on the surface of extracellular enveloped vaccinia virus as a step towards selective tumour cell targeting," J. Gen. Virol. 78:3019-3027 (1997).
Guo et al., "Vaccinia as a vector for gene delivery," Expert Opin. Biol. Ther. 4(6):901-917 (2004).

Hamid et al., "Phase II trial of intravenous C1-1042 in patients with metastatic colorectal cancer," J. Clin. Oncol. 21(8):1498-1504 (2003).
Hoshi et al., "Antitumoral effects of defective herpes simplex virus-mediated transfer of tissue inhibitor of metalloproteinases-2 gene in malignant glioma U87 in vitro: consequences for anti-cancer gene therapy," Cancer Gene Ther. 7(5):799-805 (2000).
Jacobs et al., "Positron-emission tomography of vector-mediated gene expression in gene therapy for gliomas," Lancet 358:727-729 (2001).
Kaufman et al., "Phase II randomized study of vaccine treatment of advanced prostate cancer (E7897): a trial of the Eastern Cooperative Oncology Group," J. Clin. Oncol. 22:2122-2132 (2004).
Kirn, D., "Oncolytic virotherapy for cancer with the adenovirus d11520 (Onyx-015): results of phase I and II trials," Expert Opin. Biol. Ther. 1(3):525-538 (2001).
Lorence et al., "Overview of phase I studies of intravenous administration of PV701, an oncolytic virus," Curr. Opin. Mol. Ther. 5(6):618-624 (2003).
Meighen et al., "Molecular biology of bacterial bioluminescence," Microbiol. Rev. 55(1):123-142 (1991).
Nemunaitis et al., "Pilot trial of intravenous infusion of a replication-selective adenovirus (ONYX-015) in combination with chemotherapy or IL-2 treatment in refractory cancer patients," Cancer Gene Ther. 10:341-352 (2003).
Payne, "Significance of extracellular enveloped virus in the in vitro and in vivo dissemination of vaccinia," J. Gen. Virol. 50(1):89-100 (1980).
Sanz et al., "Identification of a transcription factor, encoded by two vaccinia virus early genes, that regulates the intermediate stage of viral gene expression," Proc. Natl. Acad. Sci., 96(6):2692-2697 (1999).
Sidwell et al., "In vivo antiviral properties of biologically active compounds," Appl. Microbiol. 16(2):370-392 (1968).
Smith et al., "Oncolytic viruses as novel anticancer agents: turning one scourge against another", Exp. Opin. Invest. Drugs, 9(2):311-327 (2000).
Taubes et al., "Firefly gene lights up lab animals inside out," Science 276:1993 (1997).
Tjuvajev et al., "Comparison of radiolabeled nucleoside probes (FIAU, FHBG, and FHPG) for PET imaging of HSV1-tk gene expression," J. Nucl. Med. 43:1072-1083 (2002).
Vanderplasschen et al., "A novel virus binding assay using confocal microscopy: demonstration that the intracellular and extracellular vaccinia virions bind to different cellular receptors," J. Virol. 71(5):4032-4041 (1997).
Weir et al., "Determination of the transcriptional regulatory region of a vaccinia virus late gene," J. Virol. 61(1):75-80 (1987).
U.S. Appl. No. 12/148,542, filed Apr. 17, 2008.
U.S. Appl. No. 11/975,088, filed Oct. 16, 2007.
PCT/US2007/22172, Oct. 16, 2007.
U.S. Appl. No. 11/975,090, filed Oct. 16, 2007.
U.S. Appl. No. 11/982,102, filed Oct. 31, 2007.
U.S. Appl. No. 11/982,040, filed Oct. 31, 2007.
U.S. Appl. No. 11/981,976, filed Oct. 31, 2007.
U.S. Appl. No. 11/982,035, filed Oct. 31, 2007.
U.S. Appl. No. 12/080,766, filed Apr. 4, 2008.
U.S. Appl. No. 12/156,135, filed May 30, 2008.
PCT/US2008/006917, May 30, 2008.
U.S. Appl. No. 12/157,960, filed Jun. 13, 2008.
PCT/US2008/07377, Jun. 13, 2008.
U.S. Appl. No. 12/218,953, filed Jul. 18, 2008.
PCT/US2008/008882, Jul. 18, 2008.
U.S. Appl. No. 12/288,887, filed Oct. 24, 2008.
PCT/US2008/12061, Oct. 24, 2008.
First complaint, filed in the Superior Court for the State of California, County of Los Angeles, dated Dec. 21, 2005 (Case No. BC344912) *Genelux Corporation*, a Delaware corporation (Plaintiff) vs. *Dr. Bernard Huber*, an individual; Patentanwäthe Huber & Schüssler, a partnership under the Code Gesellschaft des Burgerlichen Rechts; Dr. Gerd Stehle, an individual; and Does 1 through 10, inclusive (Defendants).

(56) References Cited

OTHER PUBLICATIONS

*Stipulation and Order of Dismissal.* Case No. CV06-1462 AG(FMOx).
*Petition for Retroactive Grant of Foreign Filing License*, filed on May 9, 2008, in connection with U.S. Appl. No. 10/872,156.
*Joint Stipulation Regarding Defendants' Motion to Compel: (1) Deposition Testimony on Identified Subjects Pursuant to Rule 30(B)(6), and (2) The Production of Documents [Local Rule 37-2.1].* Case No. CV06-1462 AG(FMOx).
Notice of Removal of Action Under 28 U.S.C. 1441 (Diversity) Case No. CV06-1462 AG (FMOx), *Genelux Corporation*, a Delaware corporation (Plaintiff) vs. *Dr. Bernard Huber*, an individual; Patentanwälte Huber & Schüssler, a partnership under the Code Gesellschaft des Burgerlichen Rechts; Dr. Gerd Stehle, an individual; and Does 1 through 10, inclusive (Defendants).
Answer and Counterclaims for Fraud, Negligent Misrepresentation, Breach of Fiduciary Duty; Breach of Contract; and Indemnity. Case No. CV06-1462 AG (FMOx), *Genelux Corporation*, a Delaware corporation (Plaintiff) vs. *Dr. Bernard Huber*, an individual; Patentanwälte Huber & Schüssler, a partnership under the Code Gesellschaft des Burgerlichen Rechts; Dr. Gerd Stehle, an individual; and Does 1 through 10, inclusive (Defendants); Dr. Bernard Huber, an individual; Patentanwälte Huber & Schüssler, a partnership under the Code Gesellschaft des Burgerlichen Rechts; *Dr. Gerd Stehle*, an individual (Counterclaimants) vs. *Genelux Corporation*, a Delaware corporation, Ronald Simus, an individual, David Wood, an individual, and Aladar A. Szalay, an individual (Counterdefendants).
*Report of Parties' Planning Meeting for Scheduling Conference.* Case No. CV06-1462 AG (FMOx).
Notice of Motion and Motion to Compel Further Responses by Defendant/Counterclaimant Dr. Bernard Huber to Interrogatories; Joint Stipulation of the Parties; Declaration of Howard M. Loeb. Case No. CV06-1462 AG (FMOx).
*Order Regarding Discovery Motions.* Case No. CV06-1462 AG (FMOx).
Declaration of Paula K. Schoeneck.
Notice of Motion and Motion to Dismiss Counterclaimants Huber and Stehle's Fourth Cause of Action for Failure to State a Claim upon which Relief can be Granted; Memorandum of Points and Authorities; Declaration Pursuant to Local Rule 7-3. Case No. CV06-1462 GHK (FMOx).
*Counterclaimants' Opposition to Counterdefendant Genelux's Motion to Dismiss.* Case No. CV06-1462 GHK (FMOx).
*Reply to Opposition to Motion to Dismiss Counterclaimants Huber and Stehle's Fourth Cause of Action for Failure to State a Claim upon which Relief can be Granted.* Case No. CV06-1462 GHK (FMOx).
*Court Order* granting Genelux's motion to dismiss. Case No. CV06-1462 GHK (FMOx).
First Amended Counterclaims for Fraud; Negligent Misrepresentation, Breach of Fiduciary Duty; Breach of Contract; Breach of the Implied Covenant of Good Faith and Fair Dealing; and Indemnity. Case No. CV06-1462 GHK (FMOx).
Notice of Motion and Motion to Dismiss Counterclaimants Huber and Stehle's Seventh Cause of Action for Failure to State a Claim Upon Which Relief Can be Granted; Memorandum of Points and Authorities; Declaration Pursuant to Local Rule 7-3. Case No. CV06-1462 GHK (FMOx).
*Counterclaimants' Opposition to Motion to Dismiss Seventh Cause of Action.* Case No. CV06-1462 GHK (FMOx).
Reply to Opposition to Motion to Dismiss Counterclaimants Huber and Stehle's Seventh Cause of Action for Failure to State a Claim Upon Which Relief can be Granted Case No. CV06-1462 AG(FMOx).
*(In Chambers) Order Denying Motion to Dismiss Counterclaimants' Seventh Cause of Action.* Case No. CV06-1462 AG(FMOx).
*Reply to First Amended Counterclaims.* Case No. CV06-1462 AG(FMOx).
Letter, dated Jun. 3, 2004, from Istvan Fodor and Tatyana Timiryasova to the Editorial Office of *Analytical and Bioanalytical Chemisty*.
Letter, dated Jun. 3, 2004, from Istvan Fodor and Tatyana Timiryasova, to the Editor of *Nature Biotechnology*.
Letter, dated Feb. 23, 2004, from Aladar A. Szalay, Yong A. Yu, Shahrokh Shabahang, Richard E. Beltz, and Qian Zhang to Istvan Fodor.
E-Mail, dated Jul. 27, 2004, from Andrew Marshall to Aladar A. Szalay.
E-Mail, dated Jul. 28, 2004, from Aladar A. Szalay to Andrew Marshall.
Letter, dated May 16, 2004, from Richard E. Seitz, to Dr. Istvan Fodor.
"Detection of tumors in live animal models: localization of tumor development by light emission and tumor regression by light extinction," *Invention Disclosure Form LL64* (Filed with the Intellectual Property Office at Loma Linda University in 2001).
"Detection of tumors in live animal models: localization of tumor development by light emission and tumor regression by light extinction," *Invention Disclosure Form LL72* (Filed with the Intellectual Property Office at Loma Linda University in 2001).
Letter from Barry L. Taylor, Vice Chancellor for Research Affairs, Loma Linda University, to Tatana Timiryasova, dated Oct. 30, 2001.
Office Action, issued Mar. 18, 2008, in connection with U.S. Appl. No. 10/866,606.
Office Action, issued Oct. 4, 2007, in connection with Canadian patent Application No. 2,456,055.
Translation of Office Action, issued Nov. 15, 2007, in connection with Israeli Patent Application No. 160,052.
Translation of Office Action, issued Mar. 24, 2008, in connection with Japanese Patent Application No. 2003-519509.
Examination Report, issued Jun. 22, 2007, in connection with European patent Application No. 03735553.4.
WO 2007/075879, Published Jul. 5, 2007.
Amato et al., "Luminous with Promise" Chem. Eng. News. 84(49):69-73 (2006).
Brown M. Killer into cure—oncolytic viruses. Microbiology Today. 2005;56:128-31.
Chen et al. "Real-time monitoring of vaccinia virus infection in cultured cells and in living mice using light-emitting proteins" *Proceedings of the 14th International Symposium on Bioluminescence & Chemiluminescence: Chemistry, Biology and Applications*, World Scientific: Singapore: 181-184 (2007).
Davis et al., "Oncolytic virotherapy for cancer treatment: challenges and solutions" *J. Gene Med*. 7(11):1380-1389 (2005).
Everts, B. and H. van der Poel, "Replication-selective oncolytic viruses in the treatment of cancer," Cancer Gene Ther. 12:141-161 (2005).
Gherardi et al., "Recombinant poxviruses as mucosal vaccine vectors" *J Gen Virol* 86:2925-2936 (2005).
Haga et al., "Evasion of innate immunity by vaccinia virus" *Parasitology* 130:S11-S25(2005).
Hermiston T, Kirn DH. Genetically based therapeutics for cancer: similarities and contrasts with traditional drug discovery and development. Mol. Ther. 2005;11(4):496-507.
Jia et al., "Viral vectors for cancer gene therapy: Viral dissemination and tumor targeting" *Curr. Gene Ther*. 5:133-142 (2005).
Kelly et al. Novel oncolytic agent GLV-1h68 is effective against malignant pleural mesothelioma. *Hum Gene Ther*. 19(8):774-82 (2008).
Kelly et al., "Real-time intraoperative detection of melanoma lymph node metastases using recombinant vaccinia virus GLV-1h68 in an immunocompetent animal model" *Int. J. Cancer* (accessed on Oct. 21, 2008) (30 pages) (2008).
Li et al., "Oncolytic virotherapy as personalized cancer vaccine" *Int. J. Cancer* 123:493-499 (2008).
Lin SF, Price DL, Chen CH, et al. Oncolytic Vaccinia Virotherapy of Anaplastic Thyroid Cancer in Vivo. *J Clin Endocrinol Metab* (accessed on Oct. 21, 2008) (16 pages) (2008).
Lin S-F, Yu Z, Riedl C, et al. Treatment of anaplastic thyroid carcinoma in vitro with a mutant vaccinia virus. Surgery 2007;142(6):976-83.
Liu Ta-Chiang, Galanis E, Kirn D. Clinical trial results with oncolytic virotherapy: a century of promise, a decade of progress. Nat Clin Pract Oncol 2006;4:101-16.

(56) References Cited

OTHER PUBLICATIONS

Naik AM, Chalikonda S, McCart A, et al. Intravenous and isolated limb perfusion delivery of wild type and a tumor-selective replicating mutant vaccinia virus in nonhuman primates. Hum Gene Ther. 17:31-45 (2006).
Parato et al., "Recent progress in the battle between oncolytic viruses and tumours" Nature Rev. 5:965-976 (2005).
Raab et al., "Four-color labeling of cell culture and tumors of live mice upon infection with: GFP-Ruc and RFP-CBG99 expressing Vaccinia virus strains" Proceedings of the 14th International Symposium on Bioluminescence & Chemiluminescence: Chemistry, Biology and Applications, World Scientific: Singapore, 197-200 (2007).
Shen et al., "Fighting cancer with vaccinia virus: Teaching new tricks to an old dog" Mol. Therapy 11(2):180-195 (2005).
Thorne et al., "The use of oncolytic vaccinia viruses in the treatment of cancer: a new role for an old ally?" Curr. Gene Ther. 5:429-443 (2005).
Thorne SH, Hwang TH, Kirn DH. Vaccinia virus and oncolytic virotherapy of cancer. Curr Opin Mol Ther. 2005;7(4):359-65.
Woo, Y., Adusumilli, P.S., and Fong, Y. (2006). Advances in oncolytic viral therapy. Curr. Opin. Investig. Drugs 7, 549-559.
Zhang et al., "Eradication of solid human tumors in nude mice with an intravenously injected light emitting oncolytic vaccinia virus", Cancer Res. 67(20):10038-10046 (2007).
Benning, N. and D. Hasset, "Vaccinia virus infection during murine pregnancy: a new pathogenesis model for vaccinia fetalis," J. Virol. 78(6):3133-3139 (2004).
Dingli et al., "Genetically targeted radiotherapy for multiple myeloma," Blood 102(2):489-496 (2003).
Earl et al., "T-Lymphocyte priming and protection against friend leukemoa by vaccinia—Retrovirus env Gene Recombinant," Science 234:728-731 (1986).
Geisler et al., "Drug resistance and tumor heterogeneity," CME J. Gynecological Oncology 7:25-28 (2002).
Karupiah et al., "Vaccinia virus-mediated damage of murine ovaries and protection by viruses-expressed interleukin-2," Immunol. Cell Biol. 68:325-333 (1990).
Letter/Written Disclosure of the Information Disclosure Statement for the above referenced application mailed on Jan. 20, 2012, 3 pages.
Letter/Written Disclosure of the Information Disclosure Statement for the above referenced application mailed on Apr. 21, 2006, 2 pages.
Letter/Written Disclosure of the Information Disclosure Statement for the above referenced application mailed on May 2, 2006, 2 pages.
Letter/Written Disclosure of the Information Disclosure Statement for the above referenced application mailed on Jul. 13, 2006, 3 pages.
Letter/Written Disclosure of the Information Disclosure Statement for the above referenced application mailed on Aug. 27, 2007, 3 pages.
Letter/Written Disclosure of the Information Disclosure Statement for the above referenced application mailed on Dec. 19, 2008, 14 pages.
Letter/Written Disclosure of the Information Disclosure Statement for the above referenced application mailed on Oct. 9, 2009, 3 pages.
Advani et al., "Oncolytic vaccinia virus encoding an anti-VEGF antibody improves the therapeutic efficacy of fractionated radiotherapy in lung tumor xenografts," Abstract, ASTRO 53rd Annual Meeting, Miami Beach, FL, Oct. 2-6, 2011, 2 pages.
Advani et al., "Oncolytic vaccinia virus encoding an anti-VEGF antibody improves the therapeutic efficacy of fractionated radiotherapy in tumor xenografts," poster, ASTRO 53rd Annual Meeting, Miami Beach, FL, Oct. 2-6, 2011, 1 page.
Advani et al., "Radiotargeiing systemically administered oncolytic vaccinia virus to preferentially replicate in radiated gliomas," Abstract, ASTRO 53rd Annual Meeting, Miami Beach, FL, Oct. 2-6, 2011, 1 page.
Ascierto et al., "Permissivity of the NCI-60 cancer cell lines to oncolytic vaccinia virus GLV-1H68," BMC Cancer 11(1): [epub ahead of print] (2011), 27 pages.
Browne et al., "Cancer screening by systemic administration of a gene delivery vector encoding tumor-selective secretable biomarker expression," PLoS One 6:(5):e19530 (2011), 9 pages.
Chen et al., "Replication efficiency of oncolytic vaccinia virus in cell cultures prognosticates the virulence and antitumor efficacy in mice," J. Translational Med. 9(1):164 epub date Sep. 27, 2011, 11 pages.
Gentschev et al., "Significant growth inhibition of canine mammary carcinoma xenografts following treatment with oncolytic vaccinia virus GLV-1h68," J. Oncol. 2010:1-10 (2010).
Gentschev et al., "Efficient colonization and therapy of human hepatocellular carcinoma (HCC) using the oncolytic vaccinia virus strain GLV-1h68," PLoS One. 6(7): 1-9 (2011).
Harrington, K., "GL-ONC1 Phase I Trial at Royal Marsden Hospital," Roche-Genelux Meeting, Penzberg, Germany, Sep. 19, 2011, poster, 25 pages.
Hess et al., "Bacterial glucuronidase as general marker for oncolytic virotherapy or other biological therapies," J. Translational Medicine 9:172 epub date Oct. 11, 2011, 11 pages.
Pedersen et al., "A phase I clinical trial of genetically modified and imageable oncolytic vaccinia virus GL-ONC1 with clinical green fluorescent protein (GFP) imaging," J. Clin. Oncol 29:2011, Abstract No. 2577, ASCO Annual Meeting, Jun. 3-7, 2011, 3 pages.
Pedersen et al., "A phase I clinical trial of genetically modified and imageable oncolytic vaccinia virus GL-ONC1 with clinical green fluorescent protein (GFP) imaging," J. Clin. Oncol 29:2011, poster, ASCO Annual Meeting, Jun. 3-7, 2011, 1 page.
Office Action, issued Oct. 18, 2011, in connection with corresponding U.S. Appl. No. 11/981,976, 21 pages.
Notice of Allowance, issued Jun. 10, 2011, in connection with corresponding Canadian Patent Application Serial No. 2,456,055, 6 pages.
Examination Report, issued Dec. 21, 2011, in connection with corresponding Israeli Patent Application No. 160052, 4 pages.
Office Action, issued Jul. 13, 2011, in connection with corresponding U.S. Appl. No. 10/866,606, 12 pages.
Letter/Written Disclosure of the Supplemental Information Disclosure Statement for the above-referenced application, mailed on the same date herewith, 2 pages.
Examination Report, issued May 2, 2013, and received May 30, 2013, in connection with Israeli Patent Application No. 160052 [in Hebrew, provided with English translation], 7 pages.
Letter/Written Disclosure of the Supplemental Information Disclosure Statement for the above-referenced application, mailed the same day herewith, 2 pages.
Buller et al., "Decreased virulence of recombinant vaccinia virus expression vectors is associated with a thymidine kinase-negative phenotype," Nature 317:813-815 (1985).
Fisher, "Striking out at disseminated metastases: the systemic delivery of oncolytic viruses," Curr. Opin. Mol. Ther. 8(4):301-313 (2006).
Hung et al., "Vaccinia virus preferentially infects and controls human and murine ovarian tumors in mice," Gene Ther. 14:20-29 (2007).
Office Action, mailed Sep. 25, 2012, in connection with corresponding U.S. Appl. No. 10/866,606, 15 pages.
Notice of Allowance, mailed May 31, 2013, in connection with corresponding U.S. Appl. No. 10/866,606, 8 pages.
Office Action, mailed Oct. 26, 2012, in connection with corresponding U.S. Appl. No. 11/981,976, 34 pages.
Office Action, mailed Jun. 6, 2013, in connection with corresponding U.S. Appl. No. 11/981,976, 6 pages.
Notice of Allowance, mailed Jul. 31, 2013, in connection with corresponding U.S. Appl. No. 11/981,976, 7 pages.
Instructions to Foreign Associate for Response to Official Action dated Nov. 21, 2011, in connection with corresponding Israeli Patent Application No. 160,052, mailed Jan. 31, 2012, 9 pages.

* cited by examiner

VACCINIA VIRUS FOR DIAGNOSIS AND THERAPY OF TUMORS

CROSS-REFERENCE TO RELATED APPLICATIONS

This application is filed under the provisions of 35 U.S.C. §371 and claims the priority of International Patent Application No. PCT/IB02/04767 filed Jul. 31, 2002, which in turn claims priority of European Patent Application No. 01118417.3 filed Jul. 31, 2001 and European Patent Application No. 0112591.6 filed on Oct. 30, 2001.

FIELD OF THE INVENTION

The present invention relates to diagnostic and pharmaceutical compositions comprising a microorganism or cell containing a DNA sequence encoding a detectable protein or a protein capable of inducing a detectable signal, e.g. a luminescent or fluorescent protein, and, in a particular embodiment, furthermore (a) DNA sequence(s) encoding (a) protein(s) suitable for tumor therapy and/or elimination of metastatic tumors, e.g. a cytotoxic or cytostatic protein.

BACKGROUND OF THE INVENTION

Presence of bacteria in tumors was reported approximately fifty years ago. Several publications substantiated the earlier clinical findings that unexpectedly large numbers of bacteria were discovered in excised tumors from human patients. Investigators argue that chronic infections may predispose cells to malignant growth. Chronic infections of various strains of *Chlamydia* have been associated with lung and cervical cancer as well as malignant lymphoma. Another well described association between the presence of a specific bacterial species and cancer development is *Helicobacter pylori* in patients with gastric ulcers. Elevated levels of *H. pylori*-associated antibodies have been found in patients with duodenal ulcer and gastric adenocarcinoma. These observations demonstrate a concomitant presence of bacteria at tumor sites; however, it was not yet clear whether the microorganisms were the cause of tumor formation or whether the tumorous tissues were more susceptible to bacterial colonization. Intravenously injected strict anaerobic bacteria, *Clostridium pasteurianum*, into mice replicated selectively in the tumor suggesting a hypoxic microenvironment in the necrotic center Intravenous injection of attenuated *Salmonella typhimurium* mutants resulted in elevated bacterial titers in the tumor tissues in comparison to the other organs of mice upon histologic and bacteriologic analyses.

Similarly, the presence of virus particles was reported in excised human breast tumors as early as 1965. More recently, based on polymerase chain reaction (PCR) data, the human papillomavirus has been claimed to be associated with anogenital tumors and esophageal cancers, breast cancers, and most commonly, cervical cancers. In addition, the presence of hepatitis C virus in human hepatocellular carcinoma, Epstein-Barr virus in squamous cell carcinoma in Kirnura's disease, mouse mammary tumor virus-like particles (MMTV) in human breast cancer, SV40 virus in macaque astrocytoma, and herpesvirus in turtle fibropapilloma has been reported. Surprisingly, the concentration of virus particles in the tumors shows variations among patients. The presence of human papillomavirus in squamous cell carcinomas of the esophagus ranges from 0 to 72%. In contrast to tumor tissues, no virus particles have been found in tumor-free areas of the esophageal epithelium of the same patient suggesting that the virus particles are located only in the tumor tissues.

However, so far it could not be shown definitely whether the above discussed microorganisms are responsible for the development of disorders like tumors (except for papillomaviruses) or whether, e.g., tumors can attract and/or protect viruses or bacteria. Accordingly, there was no basis for the use of such microorganisms for the diagnosis or therapy of tumors. Conventional tumor diagnostic methods, such as MRI (Magnetic Resonance Imaging) lack sensitivity and specificity and therapeutic methods, e.g. surgery, are invasive and not very sensitive.

Therefore, it is the object of the present invention to provide a means for the efficient and reliable diagnosis as well as the therapy of tumors which overcomes the disadvantages of the diagnostic and therapeutic approaches presently used.

SUMMARY OF THE INVENTION

According to the present invention this is achieved by the subject matters defined in the claims. When Vaccinia virus (LIVP strain) carrying the light emitting fusion gene construct rVV-ruc-gfp was injected intravenously into nude mice, the virus particles were found to be cleared from all internal organs within 4 days, as determined by extinction of light emission. In contrast, when the fate of the injected Vaccinia virus was similarly followed in nude mice bearing tumors grown from subcutaneously implanted C6 rat glioma cells, virus particles were found to be retained over time in the tumor tissues, resulting in lasting light emission. The presence and amplification of the virus-encoded fusion proteins in the same tumor were monitored in live animals by observing GFP fluorescence under a stereomicroscope and by collecting luciferase-catalyzed light emission under a low-light videoimaging camera. Tumor-specific light emission was detected 4 days after viral injection in nude mice carrying subcutaneous C6 glioma implants ranging in size from 25 to 2500 mm$^3$. The signal became more intense after the 4th postinjection day and lasted for 30 to 45 days, indicating continued viral replication. Tumor accumulation of rVV-ruc-gfp virus particles was also seen in nude mice carrying subcutaneous tumors developed from implanted PC-3 human prostate cells, and in mice with orthotopically implanted MCF-7 human breast tumors. Further, intracranial C6 rat glioma cell implants in immunocompetent rats and MB-49 mouse bladder tumor cell implants in C57 mice were also targeted by the Vaccinia virus. Cross sections of a C6 glioma revealed that light emission was clustered in "patches" at the periphery of the tumor where the fast-dividing cells reside. In contrast, cross sections of breast tumors revealed that fluorescent "islands" were distributed throughout the tumors. In addition to primary breast tumors, small metastatic tumors were also detected externally in the contralateral breast region, as well as in nodules on the exposed lung surface, suggesting metastasis to the contralateral breast and lung. In summary, light-emitting cells or microorganims, e.g. Vaccinia virus can be used to detect and treat primary and metastatic tumors.

Similar results were obtained with light-emitting bacteria (*Salmonella, Vibrio, Listeria, E. coli*) which were injected intravenously into mice and which could be visualized in whole animals under a low light imager immediately. No light emission was detected thirty-six hours after bacterial injection in both athymic (nu/nu) mice and immunocompetent C57 mice as a result of clearing by the immune system. In the cutaneous wound of an intravenously injected animal, the bacterial light emission increases and remains detectable up to six days post-injection. In nude mice bearing tumors developed from implanted C6 glioma cells, light emission was abolished from the animal entirely thirty-six hours after delivery of bacteria, similar to mice without tumors. However, forty-eight hours post-injection, unexpectedly, a strong, rapidly increasing light emission originating only from the tumor regions was observed. This observation indicates a continuous bacterial replication in the tumor tissue. The extent of light emission is dependent on the bacterial strain used. The homing-in process together with the sustained light emission was also demonstrated in nude mice carrying prostate, bladder, and breast tumors. In addition to primary tumors, metastatic tumors could also be visualized as exemplified in the breast tumor model. Tumor-specific light emission was also observed in immunocompetent C57 mice with bladder tumors as well as in Lewis rats with brain glioma implants. Once in the tumor, the light-emitting bacteria were not observed to be released into the circulation and to re-colonize subsequently implanted tumors in the same animal. Further, mammalian cells expressing the Ruc-gfp fusion protein, upon injection into the bloodstream, were also found to home into and propagate in glioma tumors.

These findings open the way for (a) designing multifunctional viral vectors useful for the detection of tumors based on signals like light emission and/or for suppression of tumor development and/or angiogenesis signaled by, e.g., light extinction and (b) the development of bacterium- and mammalian cell-based tumor targeting systems in combination with therapeutic gene constructs for the treatment of cancer. These systems have the following advantages: (a) They target the tumor specifically without affecting normal tissue; (b) the expression and secretion of the therapeutic gene constructs are, preferably, under the control of an inducible promoter, enabling secretion to be switched on or off; and (c) the location of the delivery system inside the tumor can be verified by direct visualization before activating gene expression and protein delivery.

Accordingly, the present invention relates to a diagnostic and/or pharmaceutical composition comprising a microorganism or cell containing a DNA sequence encoding a detectable protein or a protein capable of inducing a detectable signal.

In a preferred embodiment, the microorganism or cell of said diagnostic and/or pharmaceutical composition furthermore contains (a) DNA sequence(s) encoding (a) protein(s) suitable for tumor therapy and/or elimination of metastatic tumors, such as a cytotoxic protein, a cytostatic protein, a protein inhibiting angiogenesis or a protein stimulating apoptosis. Such proteins are well-known to the person skilled in the art and further examples of suitable proteins are given below.

Any microorganism or cell is useful for the compositions of the present invention, provided that they replicate in the organism, are not pathogenic for the organism, e.g. attenuated, and are recognized by the immune system of the organism, etc. Examples of microorganisms useful for the present invention are bacteria and viruses. The term "bacteria" as used herein refers to bacteria which are per se not tumor-targeted (i.e. they can not differentiate between a cancerous cell or tissue and the non-cancerous counterpart cell or tissue) since the results of the experiments leading to the present invention show that bacteria etc. accumulate in the tumor due to the fact that in this environment they are not exposed to attack by the immune system of the host. A list of candidate bacteria which might be useful for the purposes of the present invention and which might not be tumor-targeted are given in Table 1, below. The person skilled in the art can easily identify such bacteria which are not tumor-targeted by commonly available methods, e.g. the methods described in section 61 of WO 96/40238. Preferably, said bacteria are intercellular bacteria such as $E.\ coli$, $E.\ faecalis$, $Vibrio\ cholerae$, $Vibrio\ fischeri$, $Vibrio\ harvoyi$, $Lactobacillus$ spp., $Pseudomonas$ spp. In the method of the present invention, viruses and cells, particularly mammalian cells, are preferred which are not tumor-targeted. Particularly preferred are cytoplasmic viruses.

In a particularly preferred embodiment, the diagnostic and/or pharmaceutical composition comprises a microorganism or cell containing a DNA sequence encoding a luminescent and/or fluorescent protein.

As used herein, the term "DNA sequence encoding a luminescent and/or fluorescent protein" also comprises a DNA sequence encoding a luminescent and fluorescent protein as fusion protein.

In an alternative preferred embodiment of the diagnostic and/or pharmaceutical composition, the protein encoded by the DNA sequence is a cell receptor capable of binding a ligand which can be a diagnostic or therapeutic ligand. The ligand can be a protein (including large or small peptides, antibodies, etc.), a synthetic compound (such as a synthetic steroid analog), etc. Therefore, the in vivo location of labeled ligands in live animals and human patients can be visualized, e.g, in real time by SPECT or PET. Almost any known protein ligand-receptor pair for tumor labeling is useful in the method of the present invention. Preferably, to increase specificity, mutant protein ligands (or analogs if it is a chemical compound) or mutant ligand receptors can be genetically or chemically engineered so that they will not bind to any endogenous molecules. In addition to increasing specificity, these mutants/analogs will also limit adverse effect to the normal host physiology.

In a more preferred embodiment of the diagnostic and/or pharmaceutical composition of the present invention, the ligand is a radionuclide-labelled ligand. Said ligand is, e.g., useful for tumor visualization by single-photon emission computed tomography (SPECT) or positron-emission tomography (PET) resulting from the binding of radionuclide-labelled ligand to its receptors expressed specifically on the surface of tumor cells following intravenous delivery of, e.g., engineered bacteria, viruses, or mammalian cells carrying the receptor protein gene constructs. Radionuclides may be used for conventional tumor scintigraphy, PET and possibly internal radiotherapy of tumors. Examples of radionuclides useful in the present invention are (a) $\beta^+$-emitters such as $^{11}C$, $^{13}N$, $^{15}O$ or $^{64}CU$ or (b) $\gamma$-emitters such as $^{123}I$. Other radionuclides that can, e.g., be used as tracers for PET include $^{55}Co$, $^{57}Ga$, $^{68}Ga$, $^{60}Cu(I)$, $^{67}Cu(II)$, $^{57}Ni$, $^{55}Co$, $^{52}Fe$, $^{18}F$, etc.

SPECT and PET are sensitive techniques that may be used for tumor imaging according to the present invention. Both SPECT and PET are capable of detecting trace amounts of $\beta^+$ and $\gamma$ emission from radionuclides PET is even more sensitive than SPECT. In experiments using small laboratory animals, tumor imaging is performed using a microPET instrument, which is commercially available through, eg., Concorde Microsystems (Knoxville, Tenn.).

Examples of useful radionuclide-labeled agents are $^{64}Cu$-labeled engineered antibody fragment (Wu et al., PNAS USA 97 (2000), 8495-8500), $^{64}Cu$-labeled somatostatin (Lewis et al., J. Med. Chem. 42 (1999), 1341-1347), $^{64}Cu$-pyruvaldehyde-bis(N-4-methylthiosemicarbazone) ($^{64}Cu$-PTSM) (Adonai et al., PNAS USA 99 (2002), 3030-30351 $^{52}Fe$-citrate (Leenders et al., J. Neural Transm. Suppl. 43 (1994), 123-132), $^{52}Fe/^{52m}Mn$-citrate (Calonder et al., J. Neurochem.

73 (1999), 2047-2055) and $^{52}$Fe-labeled iron (III) hydroxide-sucrose complex (Beshara et al., Br. J. Haematol. 104 (1999), 288-295, 296-302).

In order to apply the radionuclide-labeled ligand in tumor detection, the genes encoding the receptor proteins that the ligands may bind are delivered by intravenously injected bacteria, viruses, or mammalian cells according to the present invention. Since it could be shown in the examples, below, that certain intravenously injected bacteria, viruses and mammalian cells replicate specifically in the tumors, expression of the receptor proteins in the tumors will mark the tumors for targeting by the radionuclide-labeled ligands.

For example, in the case of Vaccinia virus, to allow efficient tumor detection, the virus can be used to carry gene constructs encoding receptor proteins that can bind specifically to the ligands. Intravenous injection of recombinant Vaccinia virus allows the delivery of the receptor gene and surface expression of the receptor protein in the tumor tissues. Then, the radionuclide-labeled ligands are injected intravenously into the host. The specific binding between radionuclide-labelled ligands and their receptors expressed on the tumor cell surface allows the detection of tumors based on $\beta^+$- or $\gamma$-emissions originating only from the tumors. Labelling the tumors with radionuclides will allow easy distinction between tumors and normal tissues. Therefore, handhold $\beta^+$- or $\gamma$-detectors that are attached to a surgical blade holder can be designed. Based on the signal of $\beta^+$- or $\gamma$-emission, the labelled tumors can be cleanly excised while the removal of normal tissues is kept at a minimum.

Particularly preferred is gallium-67 for the purposes of the present invention. Gallium-67 ($^{67}$Ga) can be used for diagnostic imaging using PET, SPECT, or scintigraphy. It is known for its ability to accumulate in inflammatory lesions and tumors, especially in lymphomas, but also in many other types of tumors, such as in pancreatic tumors, lung tumors etc. The mechanism of $^{67}$Ga uptake has been proposed to be through both transferrin-dependent route and transferrin-independent route. In the transferrin-dependent route, it has been shown that over-expression of transferrin receptor significantly increases $^{67}$Ga uptake by tumor cells. Furthermore, anti-transferrin receptor antibody significantly blocks $^{67}$Ga by tumor cells. For small tumor imaging, very high concentrations of $^{67}$Ga are required to overcome background signal. Thus, in this case, the use of recombinant Vaccinia virus carrying a transferrin receptor gene construct for over-expressing transferrin receptors specifically on the surface of tumor cells in live animals or human patients following intravenous injection of the viruses is preferred. $^{67}$Ga will be also delivered intravenously. High level accumulation of $^{67}$Ga in tumor cells with the help from the over-expressed transferrin receptors helps to significantly improve tumor detection abilities in live animals and human patients.

In an alternative preferred embodiment, the diagnostic and/or pharmaceutical composition of the present invention comprises a microorganism or cell containing a DNA sequence encoding a protein capable of inducing a signal detectable by magnetic resonance imaging (MRI), e.g. metal binding proteins. Furthermore, the protein can bind contrast agents, chromophores, ligands or compounds required for visualization of tissues. Preferably, said protein is a cell receptor capable of binding a paramagnetic- or superparamagnetic metal-labelled ligand. Tumor visualization by MRI, resulting from the binding of paramagnetic- or superparamagnetic-metal-labelled ligands to their receptors expressed specifically on the surface of tumor cells following, e.g., intravenous delivery of engineered bacteria, viruses, or mammalian cells according to the present invention carrying the receptor protein gene constructs has several advantages. The high level of accumulation of these metals in the tumors will facilitate tumor detection. Virtually any paramagnetic or superparamagnetic metals can be used for this purpose. Preferably, due to the systemic toxicity of naked heavy metals, the paramagnetic or superparamagnetic metals are carefully selected to keep adverse effects at minimal. In most currently available contrast agents, the metal particles are either linked to chelates or are coated with polymers, which are much safer to use than naked particles. Therefore, the use of ligands tagged with chelated or polymer-coated metals is preferred.

Methods for generating contrast agents linked with proteins are well known to the person skilled in the art, e.g., the protein ligand (or other chemical compound ligand) is first chemically attached to the chelates (e.g. diethylene triamine pentaacetic acid (DTPA)). Then, the chelate-protein complex is labeled with metals. A similar labeling method has been used in generating gallium-labeled somatostatin analogs and used in producing indium-111-labeled low density lipoprotein using DTPA-bis(stearylamide). Details of protein modifications with chelates used in contrast agents have been previously described. For example, modifying proteins with the bifunctional chelate 2-(4-isothiocyanotobenzyl-6-methyl) diethylenetriamine-pentaacetic acid (MX-DTPA)) (Mirzadeh et al., Bioconjug. Chem. 1 (1990), 59-65) and modifying proteins with the cyclic anhydride of diethylenetriamine-pentaacetic acid (cDTPAA) (Duncan and Welch, J. Nucl. Med. 34 (1993), 1728-1738) have been described.

Alternatively, MRI can be carried out by the following approaches:

(a) Modified Gadolinium Activation due to Enzyme/Protein Delivery

This approach is based on the principles of Gene-Directed Enzyme Prodrug Therapy (GDEPT), in which case the enzymes/proteins activate a systemically delivered nontoxic prodrug into active toxic drug. Specific activation of the MRI contrast agent in weak relaxivity state into strong relaxivity state by the enzyme/protein in the tumors allows tumor detection. The enzyme/protein delivery to tumors is achieved through intravenously injected engineered bacteria, viruses, and mammalian cells, which carry the gene encoding $\beta$-galactosidase (or any other related enzymes). The B. galactosidase can be in either extracellular secreted form or expressed an the bacteria or mammalian cell surface. An example of an MRI agent that can be cleaved by $\beta$-galactosidase and used in MRI imaging for tumor detection is (4,7,10-tri(acetic acid)-1-(2-$\beta$-galactopyranosylethoxy)-1,4,7,10-tetraazacyclododecane)gadolinium (Egad) (Moats et al., 1997,). In this compound, a galactopyranose residue is positioned at the 9th coordination site of the Gd$^{3+}$ ion. Due to this blockage, water protons are excluded from interacting with Gd$^{3+}$ ion, and therefore diminished effect on T1 relaxation time. In the presence of $\beta$-galactosidase, the enzyme cleaves the galactopyranose from the chelate, freeing the coordination site, and allows irreversible transition of the contrast agent from a weak to a strong relaxivity state. Since the bacterium-, virus-, or mammalian cell-based enzyme expression occurs only in tumors, the enzyme-mediated relaxivity state transition will also occur only in the tumors. Therefore, this enzyme-mediated activation of MRI contrast agents can be used for tumor detection.

In addition to the above MRI contrast agent, similar new contrast agents may be developed in which other types of residues may be attached to the chelates. These residues can be removed by their corresponding enzymes (similar to the removal of galactopyranose by galactosidase) (e.g. $\alpha$-mannosidases, $\alpha$- and $\beta$-glucosidases, $\beta$-glucuronidases) to free the 9th coordination site of the Gd$^{3+}$ ion and modify the T1 relaxation time for tumor detections. The genes encoding these enzymes may all be delivered by the engineered bacteria, viruses, or mammalian cells according to the present invention. Moreover, new contrast agents using metals other than gadolinium may be developed for enzyme-activated MRI tumor imaging.

This approach can be combined with therapy as shown in the following sections.

(b) Engineering of Delivery Vector Systems for Activation of the Contrast Agents (e g. Modified Gadolinium) First and Subseguently, the Activation of an Injected Prodrug by the Same Constitutively Expressed Enzyme (e.g. β-Galactosidase)-One-Gene-Product-Based Detection and Therapy System (OGPBDTS)

For example, the gadolinium-based contrast agent can be activated by an enzyme (e.g. β-galactosidase), as described above, which can be used for tumor detection. Subsequently, the intravenously delivered prodrugs, such as CBI, TMI, PCI (described in U.S. Pat. No. 5,646,298), may be cleaved by the same β-galactosidase in the tumors, to yield active cytotoxic drugs against tumor cells for cancer treatment.

(c) Engineering of Delivery Vector Systems with the Two-Gene-Product-Based Detection and Therapeutic Systems (TGPBDTS)

Gene 1 is linked to a constitutive promoter and produces the enzymes/proteins for sensing the contrast agents (e.g. metal-binding proteins, modified gadolinium, or other agents) and gene 2 is linked to an exogenously activatable promoter, which is silent without the activator drug, and only turned on after the detection vector system is found positive by MRI. The activation of the vector-based promoter gene construct is achieved by injection or by oral administration of the activator drug. The repeated injection of the contrast agent allows the real-time monitoring of tumor size and location of metastases during the treatment procedure.

Preferably, for transfecting the cells the DNA sequences encoding the (diagnostic or therapeutic) proteins described above, e.g., a luminescent and/or fluorescent protein are present in a vector or an expression vector. A person skilled in the art is familiar with examples thereof. The DNA sequences can also be contained in a recombinant virus containing appropriate expression cassettes. Suitable viruses that may be used in the diagnostic or pharmaceutical composition of the present invention include baculovirus, vaccinia, sindbis virus, Sendai virus, adenovirus, an AAV virus or a parvovirus, such as MVM or H-1. The vector may also be a retrovirus, such as MoMULV, MoMuLV, HaMuSV, MuMTV, RSV or GaLV. For expression in mammals, a suitable promoter is e.g. human cytomegalovirus "immediate early promoter" (pCMV). Furthermore, tissue and/or organ specific promoters are useful. Preferably, the DNA sequences encoding, e.g., a luminescent and/or fluorescent protein are operatively linked with a promoter allowing high expression. Such promoters, e.g. inducible promoters are well-known to the person skilled in the art. Preferably, the above constructs are inserted into the bacterial genome by stable integration. If such constructs are made in mammalian cells using mammalian vectors, stably transformed cell lines with a single-copy insertion will be generated for long-term expression in tumor cells.

For generating the above described DNA sequences and for constructing expression vectors or viruses which contain said DNA sequences, it is possible to use general methods known in the art. These methods include e.g. in vitro recombination techniques, synthetic methods and in vivo recombination methods as described in Sambrook et al., Molecular Cloning, A Laboratory Manual, 2$^{nd}$ edition (1989) Cold Spring Harbor Laboratory Press, Cold Spring Harbor, N.Y., for example. Methods of transfecting cells, of phenotypically selecting transfectants and of expressing the DNA sequences by using the above described vectors are known in the art.

The person skilled in the art knows DNA sequences encoding proteins, e.g., luminescent or fluorescent proteins that can be used in the diagnostic and/or pharmaceutical composition of the present invention. During the past decade, the identification and isolation of structural genes encoding light-emitting proteins from bacterial luciferase from *Vibrio harveyi* (Belas et al., Science 218 (1982), 791-793) and from *Vibrio fischerii* (Foran and Brown, Nucleic acids Res. 16 (1988), 177), firefly luciferase (de Wet et al., Mol. Cell. Biol. 7 (1987), 725-737), aequorin from *Aequorea victoria* (Prasher et al., Biochem. 26 (1987), 1326-1332), *Renilla* luciferase from *Renilla reniformis* (Lorenz et al., PNAS USA 88 (1991), 4438-4442) and green fluorescent protein from *Aequorea victoria* (Prasher et al., Gene 111 (1992), 229-233) have been described that allow the tracing of bacteria, viruses or mammalian cells based on light emission. Transformation and expression of these genes in bacteria allows detection of bacterial colonies with the aid of the low light imaging camera or individual bacteria under the fluorescent microscope (Engebrecht et al., Science 227 (1985), 1345-1347; Legocki et al., PNAS 83 (1986), 9080-9084; Chalfie et al., Science 263 (1994), 802-805).

Luciferase genes have been expressed in a variety of organisms. Promoter activation based on light emission, using lux AB fused to the nitrogenase promoter, was demonstrated in *Rhizobia* residing within the cytoplasm of cells of infected root nodules by low light imaging (Legocki et al., PNAS 83 (1986), 9080-9084; O'Kane et al., J. Plant Mol. Biol. 10 (1988), 387-399). Fusion of the lux A and lux B genes resulted in a fully functional luciferase protein (Escher et al., PNAS 86 (1989), 6528-6532). This fusion gene (Fab2) was introduced into *Bacillus subtilis* and *Bacillus meqatherium* under the xylose promoter and then fed into insect larvae and was injected into the hemolymph of worms. Imaging of light emission was conducted using a low light video camera. The movement and localization of pathogenic bacteria in transgenic *arabidopsis* plants, which carry the pathogen-activated PAL promoter-bacterial luciferase fusion gene construct, was demonstrated by localizing *Pseudomonas* or *Erwinia* spp. infection under the low light imager as well as in tomato plant and stacks of potatoes (Giacomin and Szalay, Plant Sci. 116 (1996), 59-72).

All of the luciferases expressed in bacteria require exogenously added substrates such as decanal or coelenterazine for light emission. In contrast, while visualization of GFP fluorescence does not require a substrate, an excitation light source is needed. More recently, the gene cluster encoding the bacterial luciferase and the proteins for providing decanal within the cell, which includes luxCDABE was isolated from *Xenorhabdus luminescens* (Meighen and Szittner, J. Bacteriol. 174 (1992), 5371-5381) and *Photobacterium leiognathi* (Lee et al., Eur. J. Biochem. 201 (1991), 161-167) and transferred into bacteria resulting in continuous light emission independent of exogenously added substrate (Fernandez-Pinas and Wolk, Gene 150 (1994), 169-174). Bacteria containing the complete lux operon sequence, when injected intraperitoneally, intramuscularly, or intravenously, allowed the visualization and localization of bacteria in live mice indicating that the luciferase light emission can penetrate the tissues and can be detected externally (Contag et al., Mol. Microbiol. 18 (1995), 593-603).

Preferably, the microorganism of the present invention is a bacterium which is not tumor-targeted, e.g. an attenuated bacterium. A list of candidate bacterial strains that might be useful for the present invention (i.e. BMPT (bacterium-mediated protein therapy) and tumor imaging) and which might not be tumor-targeted are listed in Table 1. The person skilled in the art can easily identify such bacteria which are not tumor-targeted by commonly available methods, e.g. the methods described in section 6.1 of WO 96/40238.

For safety and direct applicability to humans, bacterial cell lines such as milk and cheese associated microorganisms are preferred which are naturally consumed by most individuals and have intrinsic anti-tumor activity when injected directly to solid tumors. Such bacteria also include bacteria that were naturally isolated from human tumors which developed co-existence (symbiosis) with a variety of types of tumors or with a specific type of tumor. Extracellular secretion of the therapeutic proteins by bacteria is mediated through either signal peptides or endogenous protein secretion pathways. To provide additional safety to the BMPT, bacterial inducible promoters, such as IPTG-induced lac promoter may be used to exogenously regulate therapeutic protein production by bacteria. IPTG-regulated expression of mammalian proteins in bacteria has been well documented. IPTG has also been shown to be functional in promoter activation in animals. In addition to lac promoter, other examples of promoters that allow regulation of gene expression in bacteria include the ara promoter (activated by arabinose) and PLtetO-1 promoter (activated by anhydrotetracycline (aTc)) (Lutz and Bujard, Nucleic Acids Res. 25 (1997), 1203-1210).

TABLE 1

Examples of candidate bacterial strains which might be useful in the present invention:

| Bacterial strain | Brief description | Reference |
|---|---|---|
| Aerobes, gram positive | | |
| Lactobacillus bulgaricus | Yogurt bacteria; nonpathogenic (part of normal flora beneficial organism needed by human body); blastolysin fraction isolated from L. bulgaricus shows antitumor effect (Bogdanov et al. 1975; Bogdanov et al. 1977; Ketlinskii et al. 1987); may reduce the risk of developing colon tumors in humans (Wollowski et al. 2001); ATCC#11842. | Simonds et al. 1971, J Bacteriol 107: 382-384; Bogdanov et al. 1975, FEBS Lett 57: 259-261; Bogdanov et al. 1977, Biull Eksp Biol Med 84: 709-712; Ketlinskii et al. 1987, Vopr Onkol 33: 51-56; Wollowski et al. 2001, Am J Clin Nutr 73: 451S-455S |
| Lactobacillus casei | Nonpathogenic (part of normal flora beneficial organism needed by human body); i.v. injected LC9018 strain of L. casei shows markedly inhibition of the growth of subcutaneously inoculated sarcoma-180 in mice (Kato et al. 1981); shows antitumor activity from i.p. injected L. casei (LC9018 strain) (Kato et al. 1988); ATCC# 393. | Kato et al. 1981, Gann 72: 517-523; Kato et al. 1988, Cancer Immunol Immunother 26: 215-221 |
| Lactobacillus acidophilus | Nonpathogenic (part of normal flora beneficial organism needed by human body); inhibitory effect on liver tumorigenesis (Mizutani and Mitsuoka 1980); reduces 1,2-dimethylhydrazine (DMH)-induced intestinal tumors in male Sprague-Dawley rats (McIntosh et al 1999); shows strong antiproliferative effect of milk fermented by L. acidophilus on the growth of a human breast cancer cell line (Biffi et al. 1997); | Mizutani and Mitsuoka 1980, Cancer Lett 11: 89-95; Biffi et al. 1997, Nutr Cancer 28: 93-99; McIntosh et al. 1999, Nutr Cancer 35: 153-159 |
| Lactobacillus brevis | Nonpathogenic (part of normal flora beneficial organism needed by human body); | |
| Lactobacillus paracasei | Nonpathogenic (part of normal flora beneficial organism needed by human body); shows antiproliferative effect of milk fermented by L. paracasei on the growth of a human breast cancer cell line (Biffi et al. 1997); | Biffi et al. 1997, Nutr Cancer 28: 93-99 |
| Lactobacillus plantarum | Nonpathogenic (part of normal flora beneficial organism needed by human body); Murosaki et al. (2000) described that "that daily administration of L. plantarum L-137 is required to exert an antitumor effect at the late stages of tumor development when IL-12 production is considerably impaired"; | Murosaki et al. 2000, Cancer Immunol Immunother 49: 157-164 |
| Lactobacillus rhamnosus | Nonpathogenic (part of normal flora beneficial organism needed by human body); | |
| Lactobacillus salivarius | Nonpathogenic (part of normal flora beneficial organism needed by human body); modification of enteric flora in | O'Mahony et al. 2001, Aliment |

TABLE 1-continued

Examples of candidate bacterial strains which might be useful in the present invention:

| Bacterial strain | Brief description | Reference |
|---|---|---|
| | IL-10 knockout mice by probiotic lactobacilli (through milk feeding) was associated with reduced prevalence of colon cancer and mucosal inflammatory activity (O'Mahony et al. 2001); | Pharmacol Ther 15: 1219-1225 |
| *Lactobacillus sporogenes* | Nonpathogenic (part of normal flora beneficial organism needed by human body); | |
| *Lactobacillus lactis* | Nonpathogenic (part of normal flora beneficial organism needed by human body); | |
| *Lactobacillus fermentum* | ATCC#9338 | |
| *Streptococcus thermophilus* | Yogurt bacteria; nonpathogenic (part of normal flora beneficial organism needed by human body); reported tumor-specific transplantation resistance in mice after treatment of initial tumors with *S. thermophilus* (Kaklij and Kelkar 1996); T-lymphocytes are involved in antitumor activity exhibited by *S. thermophilus* (Kaklij et al. 1991); intraperitoneal administration of *S. thermophilus* resulted in complete cure in a very significant proportion of ascitic form of sarcoma-180 or Ehrlich ascites carcinoma tumor-bearing mice (Kelkar et al. 1988); ATCC# BAA-250D. | Kelkar et al. 1988, Cancer Lett 42: 73-77; Kaklij et al. 1991, Cancer Lett 56: 37-43; Kaklij and Kelkar 1996, Microbiol Immunol 40: 55-58 |
| *Bacillus subtilis* | Nonpathogenic; *B. subtilis* bacteremia has been significantly linked with cancer patients (Banerjee et al. 1988); | Banerjee et al. 1988, Arch Intern Med 148: 1769-1774 |
| *Bacillus megaterium* | Nonpathogenic; peptidoglycan from *B. megaterium* inhibits tumor growth (Nauciel and Goguel 1977); | Nauciel and Goguel 1977, J Natl Cancer Inst 59: 1723-1726 |
| *Bacillus polymyxa* | Nonpathogenic; | |
| *Mycobacterium smegmatis* | Nonpathogenic; fast-growing; Saito and Watanabe (1981) showed that "the bacteriocin from *M. smegmatis* produced morphological alterations and inhibition of synthesis of ribonucleic acid, deoxyribonucleic acid and protein in the transformed but not in the nontransformed cells"; | Lamensans et al. 1975, Proc Natl Acad Sci USA 72: 3656-3660; Saito and Watanabe 1981, Microbiol Immunol 25: 13-22 |
| *Mycobacterium vaccae* | Nonpathogenic; | |
| *Mycobacterium microti* | Nonpathogenic; ATCC# 35782 | |
| *Mycobacterium habana* | Nonpathogenic; slow-growing, photochromogen originially isolated from monkeys; | |
| *Listeria monocytogenes* | Intracellular pathogen | |
| *Enterococcus faecalis* | Have been isolated from tumors and infection endocarditis; ATCC# 29212, 51299 | Milbrandt 1998, Clin Cardiol 21: 123-126 |

Aerobes, gram negative

| Bacterial strain | Brief description | Reference |
|---|---|---|
| *Escherichia coli* | Intravenously injected *E. coli* shows tumor-specific localization. | Shabahang et al. unpublished data |
| *Salmonella typhimurium* | Bermudes and associates have used intravenously injected *Salmonella* as a protein delivery vector (Pawelek et al. 1997; Bermudes et al. 2000; Clairmont et al. 2000; Zheng et al. 2000;) Bermudes and associates showed a *Salmonella* (TK)-dependent [(14)C]FIAU accumulation of at least 30-fold higher in tumor tissue compared to muscle tissue (Tjuvajev et al. 2001); Phase I study of the intravenous administration of attenuated *Salmonella typhimurium* to patients with metastatic melanoma showed NO ANTITUMOR effect (Toso et al. 2002) | Pawelek et al. 1997, Cancer Res 57: 4537-4544; Bermudes et al. 2000, Adv Exp Med Biol 465: 57-63; Clairmont et al. 2000, J Infect Dis 181: 1996-2002; Zheng et al. 2000, Oncol Res 12: 127-135; |

TABLE 1-continued

Examples of candidate bacterial strains which might be useful in the present invention:

| Bacterial strain | Brief description | Reference |
|---|---|---|
| | | Tjuvajev et al. 2001, J Control Release 74: 313-315; Toso et al. 2002, J Clin Oncol 20: 142-152. |
| *Vibrio cholera* | Intravenously injected *V. cholera* shows tumor-specific localization; nonpathogenic strains of *V. cholera* are available; | Shabahang et al. unpublished data |
| *Vibrio harveyi* | Nonpathogenic; luminescent bacteria; ATCC# 700106. | |
| *Pseudomonas fluorescens* | Nonpathogenic; motile by means of multiple polar flagella; *P. fluorescens* bacteremia has been reported in cancer patients (Hsueh et al. 1998); *P. fluorescens* can bind to nerve cells and behave as a pathogen (Picot et al. 2001); normally grow at 26-30° C., but ATCC# 17583 can grow at 37° C. | Hsueh et al. 1998, J Clin Microbiol 36: 2914-2917; Picot et al. 2001, Microbes Infect 3: 985-995 |
| *Pseudomonas putida* | *P. putida* bacteremia has been reported in cancer patients (Martino et al. 1996); L-Methioninase from *P. putida* depletes methionine and inhibits tumor growth (Kokkinakis et al. 1997); normally grow at 26° C., but ATCC# 43142, 47054 can grow at 37° C. | Pekhov et al. 1983, Biull Eksp Biol Med 95: 87-88; Anaissie et al. 1987, Am J Med 82: 1191-1194; Martino et al. 1996, Eur J Clin Microbiol Infect Dis 15: 610-615; Kokkinakis et al. 1997, Nutr Cancer 29: 195-204; Miki et al. 2000, Cancer Res 60: 2696-2702 |
| Anaerobes, gram positive | | |
| *Bifidobacterium bifidum* | Nonpathogenic (part of normal flora beneficial organism needed by human body); showed by Kimura et al. (1980) that "selectively localized and proliferated in several types of mouse tumors following i.v. administration" and "None of the same bacilli could be detected in the tissues of healthy organs such as the liver, spleen, kidney, lung, blood, bone marrow, and muscle 48 or 96 hr after i.v. administration into tumor-bearing mice"; shows antiproliferative effect of milk fermented by *B. bifidum* on the growth of a human breast cancer cell line (Biffi et al. 1997); ATCC# 11863, 15696 | Kimura et al. 1980, Cancer Res 40: 2061-2068; Biffi et al. 1997, Nutr Cancer 28: 93-99 |
| *Bifidobacterium longum* | Nonpathogenic (part of normal flora beneficial organism needed by human body); inhibitory effect on liver tumorigenesis (Mizutani and Mitsuoka 1980); *B. longum* was shown to "selectively localized to and proliferated in 7,12-dimethylbenz[a]anthracene-induced rat mammary tumors after systemic application." (Yazawa et al. 2001); was shown to selectively localize and grow in hypoxic tumors (Yazawa et al. 2000); ATCC# 15707 | Mizutani and Mitsuoka 1980, Cancer Lett 11: 89-95; Yazawa et al. 2000, Cancer Gene Ther 7: 269-274; Yazawa et al. 2001, Breast Cancer Res Treat 66: 165-170 |
| *Bifidobacterium infantis* | Nonpathogenic (part of normal flora beneficial organism needed by human body); shows strong antiproliferative effect of milk fermented by *B. infantis* on the growth of a human breast cancer cell line (Biffi et al. 1997) and other tumor cells or tumors (Kohwi et al. 1978; Sekine et al. 1985; Sekine et al. 1995); ATCC# 15697 | Kohwi et al. 1978, Gann 69: 613-618; Sekine et al. 1985, Cancer Res 45: 1300-1307, Sekine et al. 1995, Biol Pharm Bull |

TABLE 1-continued

Examples of candidate bacterial strains which might be useful in the present invention:

| Bacterial strain | Brief description | Reference |
|---|---|---|
| | | 18: 148-153, Biffi et al. 1997, Nutr Cancer 28: 93-99 |
| *Bifidobacterium laterosporus* | Nonpathogenic (part of normal flora beneficial organism needed by human body); | |
| *Bifidobacterium animalis* | Shows antiproliferative effect of milk fermented by *B. animalis* on the growth of a human breast cancer cell line (Biffi et al. 1997); ATCC# 25527 | Biffi et al. 1997, Nutr Cancer 28: 93-99 |
| *Actinomyces israelii* | Actinomycetes are fungus-like bacteria that form filamentous branches. They are known to reside in the mouth and in the intestinal tract. Pathogenic proliferation of the organisms, which is usually a result of trauma to the region of infection, can lead to actinomycosis. | |
| *Eubactrium lentum* | *Eubactrium* species are normal flora of the intestinal tract. However, they may cause opportunistic infections. *E. lentum*, the most often isolated species, has been linked to endocarditis and some wound infections. | |
| *Peptostreptococcus anaerobius* | One of the most common bacteria found in non-sparing anaerobic (NSA) infections in certain surgical group of patients; ATCC# 27337 | Chatterjee and Chakraborti 1995, J Indian Med Assoc 93: 333-5, 339 |
| *Peptococcus prevotii* | Found in wound infections; | Chatterjee and Chakraborti 1995, J Indian Med Assoc 93: 333-5, 339 |
| *Clostridium novyi* | Strict anaerobe; wildly in soil; motility is inhibited in the presence of oxygen; Vogelstein lab (Dang et al. 2001) showed that "intravenously injected *C. novyi*-NT spores germinated within the avascular regions of tumors in mice and destroyed surrounding viable tumor cells", "Large numbers (up to $10^8$ in a volume of 500 µl) of *C. novyi* and *C. sordellii* spores could be injected intravenously into normal mice without causing any noticeable side effects."; ATCC# 19402 | Dang et al. 2001, Proc Natl Acad Sci. USA 98: 15155-15160; Nuyts et al. 2002, Anticancer Drugs 13: 115-125 |
| *Clostridium sordellii* | ATCC# 9714 | |
| *Clostridium absonum* | ATCC# 27555 | |
| *Clostridium acetobutylicum* | Theys et al. (2001) demonstrated "Specific targeting of cytosine deaminase to solid tumors by engineered *Clostridium acetobutylicum*"; Other related papers (Theys et al. 1999); ATCC# 824 | Theys et al. 1999, Appl Environ Microbial 65: 4295-4300; Theys et al. 2001, Cancer Gene Ther 8: 294-297 |
| *Clostridium bifermentans* | ATCC# 17836 | |
| *Clostridium difficile* | The link between *C. difficile* and cancer patients has been documented (Anand and Glatt 1993; Simon et al. 2000); ATCC# 700057 | Anand and Glatt 1993, Clin Infect Dis 17: 109-113; Schuller et al. 1995, Arch Dis Child 72: 219-222; Wehl et al. 1999, Med Pediatr Oncol 32: 336-343; Simon et al. 2000, Infect Control Hosp Epidemiol 21: 592-596 |
| *Clostridium histolyticum* | ATCC# 19401 | |
| *Clostridium perfringens* | Pathogenic; *C. perfringens* bacteremia has been often reported in cancer patients; *C. perfringens* enterotoxin kills tumor cells and reduce tumor growth (Michl et al. 2001); ATCC# 3624, 13124 | Bodey et al. 1991, Cancer 67: 1928-1942; Michl et al. |

TABLE 1-continued

Examples of candidate bacterial strains which might be useful in the present invention:

| Bacterial strain | Brief description | Reference |
|---|---|---|
| | | 2001, Gastroenterology 121: 678-684 |
| *Clostridium beijerinckii* | Brown and associates at Stanford described that "To demonstrate the specificity of this approach for tumor targeting, we intravenously injected the inactive spore form of *C. beijerinckii*, which upon transition to a reproductive state will express the *E. coli* nitroreductase gene. Nitroreductase activity was detectable in 10 of 10 tumors during the first 5 days after intravenous injection of inactive clostridial spores, indicating a rapid transition from spore to reproductive state" (Lemmon et al. 1997); other related papers on *C. beijerinckii* tumor targeting (Minton et al. 1995, FEMS Microbiol Rev 17: 357-364; Fox et al. 1996); ATCC# 25752 | Minton et al. 1995, FEMS Microbiol Rev 17: 357-364; Fox et al. 1996, Gene Ther 3: 173-178; Lemmon et al. 1997, Gene Ther 4: 791-796 |
| *Clostridium sporogenes* | Harmless saprophyte; Brown and associates at Stanford described that "systemic delivery of 5-FC into mice previously injected with CD-transformed spores of *C. sporogenes* produced greater antitumor effect than maximally tolerated doses of 5-FU"; ATCC# 19404 | Liu et al. 2002, Gene Ther 9: 291-296 |
| *Staphylococcus aureus* | Non-motile, non-sporing and facultatively anaerobic; a halotolerant (salt tolerant) organism associated with the nasal mucosa of mammals which has both benign and pathogenic strains; *S. aureus* bacteremia is frequently seen in cancer patients; ATCC# 25923 | |
| *Staphylococcus epidermidis* Anaerobes, gram negative | Nonpathogenic normal microflora component of the skin; | |
| *Acidaminococcus fermentans* | Found in wound infections; | Chatterjee and Chakraborti 1995, J Indian Med Assoc 93: 333-5, 339 |
| Plant bacteria, gram positive | | |
| *Clavibacter michiganensis* subsp. *michiganensis* Plant bacteria, gram negative | Pathogen of tomato | |
| *Agrobacterium tumefaciens* | *A. tumefaciens* in plant tumors (Ullrich and Aloni 2000); Kunik et al. (2001, Proc Natl Acad Sci USA 98: 1871-1876) described "*Agrobacterium* attaches to and genetically transforms several types of human cells"; it has been reported that antibodies against *A. tumefaciens* were found in patients with various cancers (Aksac 1974, Turk Hij Tecr Biyol Derg 34: 48-51); grow at 26-30° C.; ATCC# 15955 | Aksac 1974, Turk Hij Tecr Biyol Derg 34: 48-51; Zambryski et al. 1982, J Mol Appl Genet 1: 361-370; Rezmer et al. 1999, Planta 209: 399-405; Ullrich and Alorri, 2000, J Exp Bot 51: 1951-1960; Azmi et al. 2001, Planta 2001 May, 213(1): 29-36; Kunik et al. 2001, Proc Natl Acad Sci USA 98: 1871-1876 |
| *Erwinia herbicola* | Non-capsulated, non-spore forming, short rods with a single monotrichous polar flagellum, and are harmless to | Meadows et al. 1976, Cancer |

TABLE 1-continued

Examples of candidate bacterial strains which might be useful in the present invention:

| Bacterial strain | Brief description | Reference |
|---|---|---|
| | humans; purified tyrosine phenol-lyase from *E. herbicola* significantly inhibited growth of established B-16 melanoma tumors; | Res 36: 167-171. |
| *Azorhizobium caulinodans* | Symbiotic, colonize plants, fix nitrogen; | |
| *Xanthomonas campestris* pv. *vesicatoria* | Pathogen of pepper and tomato | |
| *Xanthomonas campestris* pv. *campestris* | Pathogen of beat and cabbage; *E. coli* lac promoter was shown to be functional in this plant pathogen; | Soby and Daniels 1996, Appl Microbiol Biotechnol 46: 559-561 |

Note:
The content of this table is by no-means to be exhaustive. Any other similar bacterial strains, which are not listed in this table, are also considered to be included.

Particularly preferred is attenuated *Vibrio cholerae*.

A further example of a bacterium useful for the preparation of a diagnostic composition for tumor-imaging or monitoring a therapeutic tumor treatment is a magnetic bacterium (Metal-Binding-Bacteria-Mediated Tumor Detection (MBBMTD)). Such bacteria allow tumor detection through the accumulation of iron-based contrast agents. Magnetic bacteria can be isolated from fresh and marine sediments. They are capable of producing magnetic particles ($Fe_3O_4$) (Blakemore, Annu. Rev. Microbiol. 36 (1992), 217-238). To do so, they have efficient iron uptake systems, which allow them to utilize both insoluble and soluble forms of iron. *Magnetospirillum magneticum* AMB-1 is an example of such magnetic bacteria that has been isolated and cultured for magnetic particle production (Yang et al., Enzyme Microb. Technol. 29 (2001), 13-19). Since it can be expected that these magnetic bacteria (naturally occurring or genetically modified), when injected intravenously, possess the similar tumor accumulation ability as that of *Vibrio cholera*, for example, these bacteria can be used for accumulating iron-based contrast agents in the tumors, which in turn allows tumor detection by MRI. Similarly, other naturally isolated metal-accumulating strains of bacteria can be used for tumor targeting, absorption of metals from contrast agents, and eventually tumor imaging.

Alternatively, viruses such as Vaccinia virus, AAV, a retrovirus etc. are also useful for the diagnostic and therapeutic compositions of the present invention; see Table 2 listing examples of viruses useful in the present invention.

TABLE 2

Examples of viruses useful in the present invention:

| Viral strains | Brief description | References |
|---|---|---|
| Vaccinia virus | We have shown that viral thymidine kinase mutation is not necessary for tumor accumulation by intravenously injected Vaccinia virus. | Yu et al. 2002, unpublished data |
| Epstein-Barr virus | | |
| Human papillomavirus | | zur Hausen 2002, Nat Rev Cancer 2: 342-350 |
| Retrovirus | | |
| Adenovirus | | Lindsey 2002, Lancet Oncol 3: 264 |
| Adenoassociated virus | | |
| SV40 virus | | |
| Cytomegalovirus | | |
| Newcastle Disease Virus | safe, replicates in and kill tumor cells; local injection is more effective than systemic injection | Schirrmacher et al. 2001, Int J Oncol 18: 945-952 |
| Bovine enterovirus | Bovine enterovirus has been shown to exhibit wide tissue tropism for cell types in vitro. It also shows oncolytic activity towards human cells. | Smyth et al. 2002, Int J Mol Med 10: 49-53 |
| Lymphocytic choriomeningitis virus (LCMV) | high stability, low toxicity, and broad host range | Beyer et al. 2002, J Virol 76: 1488-1495 |
| Lentiviruses | | |
| Derivatives of the Edmonston-B strain of measles virus (MV-Ed) | safe, live attenuated, has been shown to induce regression of human lymphoma xenografts in immunodeficient mice | Grote et al. 2001, Blood 97: 3746-3754 |

TABLE 2-continued

Examples of viruses useful in the present invention:

| Viral strains | Brief description | References |
| --- | --- | --- |
| Herpes simplex virus type I | | Lachmann and Efstathiou 1999, Curr Opin Mol Ther 1: 622-632; Wu et al. 2001, Cancer Res 61: 3009-3015 |
| Attenuated yellow fever (YF) virus | powerful vaccine, safe | Barrett 1997, Biologicals cals 25: 17-25; McAllister et al. 2000, J Virol 74: 9197-205 |

Note:
The content of this table is by no-means to be exhaustive. Any other similar viral strains, which are not listed in this table, are also considered to be included.

Preferably, the virus is Vaccinia virus.

Preferably, the cell of the diagnostic or therapeutic composition of the present invention is a mammalian cell such as stem cells which can be autologous or heterologous to the organism. Examples of suitable cell types are shown in Table 3.

TABLE 3

Examples of mammalian cells useful in the present invention:

| Mammalian cells | Brief description | Reference |
| --- | --- | --- |
| Stem cells | It has been shown that neural stem cells implanted intravenously outside the central nervous system target to an intracranial tumor. Additionally, when implanted intracranially at distant sites from the tumor, such as into the contralateral hemisphere or into the cerebral ventricles, the donor neural stem cells migrate through normal brain tissues to target the human glioblastoma cells. | Aboody et al. 2000, Proc Natl Acad Sci USA 97: 12846-12851; Herrlinger et al. 2000, Mol Ther 1: 347-357 |
| Different types of tumor cells | For example, ovarian cancer cells have been shown to infiltrate the pleural space of patients to target malignant pleural mesotheliomas (Harrison et al. 2000, Ann Thorac Surg 70: 407-411). We have shown that intravenously injected fibrosarcoma cells accumulate in breast tumors and subcutaneous glioma tumors (Yu et al. unpublished data). | |

Note:
The content of this table is by no-means to be exhaustive. Any other similar types of mammalian cells, which are not listed in this table, are also considered to be included.

In a further preferred embodiment of the diagnostic and/or therapeutic composition of the present invention the luminescent or fluorescent protein is a luciferase, green fluorescent protein (GFP) or red fluorescent protein (RFP).

In a particularly preferred embodiment, the microorganism or cell of the diagnostic and/or pharmaceutical composition of the present invention additionally contains a gene encoding a substrate for the luciferase. In an even more preferred embodiment, the microorganism or cell of the diagnostic and/or pharmaceutical composition of the present invention contains a ruc-gfp expression cassette which contains the *Renilla* luciferase (ruc) and Aequorea gfp cDNA sequences under the control of a strong synthetic early/late (PE/L) promoter of Vaccinia or the luxCDABE cassette.

A preferred use of the microorganisms and cells described above is the preparation of a diagnostic composition for tumor-imaging. The diagnostic composition of the present invention can be used e.g. during surgery, to identify tumors and metastasis. Furthermore, the diagnostic composition of the present invention is useful for monitoring a therapeutic tumor treatment. Suitable devices for analysing, e.g., the localization or distribution of luminescent and/or fluorescent proteins in an organism, organ or tissue are well known to the person skilled in the art and, furthermore described in the literature cited above as well as the examples, below. Additionally, the microorganisms and cells can be modified in such a way that they bind metals and consequently are useful in MRI technology to make tumor localization more specific.

The present invention also relates to the use of an antimicrobial, e.g. antibacterial or antiviral compound, e.g., peptide or protein fused to a detectable protein for the preparation of a diagnostic composition for tumor-imaging or monitoring a therapeutic tumor treatment. This diagnostic composition is useful for tumor detection through the binding of the antimicrobial compound, e.g., a light-emitting or radiolabeled antimicrobial peptide/protein with bacteria localized in tumors (Peptide-Linked-Tumor-Targeting-Vector-Detection (PLT-TVD)).

The present invention also relates to the use of an antimicrobial, e.g. antibacterial or antiviral compound, e.g., peptide or protein fused to a therapeutic protein for the preparation of a pharmaceutical composition for tumor therapy.

Examples of naturally occurring antimicrobial proteins include ubiquicidin (UBI, 6.7 kDa) and lactoferrin (hLF, 77 kDa). UBI was originally isolated from murine macrophages and later from human airway epithelial cells. hLF is found in mucosa and neutrophils, and is known to bind to surface structures of both gram-negative and gram-positive bacteria. Small synthetic peptides containing the bacteria binding domains of UBI or hLF have been designed for imaging of bacterial infections, which can be discriminated from sterile inflammations (Nibbering et al., Nucl. Med. Commun. 19 (1998), 1117-1121; Welling et al., Nucl. Med. Biol. 29 (2002), 413-422; Welling et al., Eur. J. Nucl. Med. 27 (2000), 292-301). These peptides are radiolabeled with $^{99m}$Tc, which allows real-time visualization in live animals using planar scintigraphy. For example, a planar gamma camera (e.g. Toshiba GCA 7100/UI, Tokyo, Japan) equipped with a low-energy general-purpose parallel-hole collimator can be used to visualize the distribution of $^{99m}$Tc-labelled antimicrobial peptides in live animals or humans. To apply these synthetic peptides for tumor detection, first the tumorous individuals are infected with a particular strain of extracellular bacteria. After bacterial colonization of the tumors, the radiolabelled compounds, e.g., peptides are delivered intravenously. Specific binding of the labeled peptides to the bacteria in the tumors can be visualized in real time by scintigraphy, which therefore allows the localization of tumors in humans and animals. In addition to labeling with $^{99m}$Tc, the compounds, e.g., synthetic peptides can also be labeled with paramagnetic- or superparamagnetic-metal particles for visualization using MRI or the compounds can be labeled with radionuclides, such as $^{55}$CO, $^{68}$Ga, $^{60}$CU(II), $^{123}$I etc. for non-invasive visualization by SPECT or PET. Furthermore, the compounds, e.g., synthetic peptides can also be tagged with fluorescent probes, fluorescent proteins (such as green fluorescent protein (GFP) or DsRed)., or luminescent proteins (such as *Renilla* luciferase, firefly luciferase) for real-time visualization in an individual.

In addition to UBI and hLF, there are many other examples of antimicrobial peptides/proteins produced by bacteria, plants, invertebrates, and vertebrates including humans (Schroder, *Cell. Mol. Life. Sci.* 56 (1999), 32-46; Cole and Ganz, Biotechniques 29 (2000), 822-826, 828, 830-831) which are useful for the purposes of the present invention, e.g. pediocin PA-1 from lactic acid bacteria, gramicidin S from *Bacillus brevis*, protegrin-1 from porcine leukocytes, SMAP-29 from sheep myeloid cells, buforin I & buforin II from Asian toad, beta-defensins, LL-37, a fragment of human cathelicidin hCAP-18, arasin I from catfish, granulysin, PAMP from *Propionibaeterium jensenii* etc. Based on these naturally occurring antimicrobial proteins, small peptides can be designed and synthesized to retain the bacteria-binding capability while eliminating the bacteria-killing effect by the original proteins. These synthetic peptides could then be used in bacterium-mediated tumor detection.

Similar to detection of bacteria by antibacterial compounds (e.g. peptides/proteins), antiviral compounds (e.g. peptides/proteins) may be used for detecting viral particles in the tumors. Lactoferricin is one of the examples of antiviral peptide/protein that may be used to design peptides for detecting viral particles. In addition to the antimicrobial peptides/proteins discussed, radiolabelled- or light-emitting-protein/probe-labeled antibody fragments can also be used to target bacteria or viruses localized in tumors for tumor detection.

Moreover, the antimicrobial compound can be fused to a metal-binding protein (Fusion-Peptide-Linked Tumor Targeting Vector Detection (PLTTVD)) for detecting the accumulation of bacteria, viruses etc. according to the present invention in tumors. After allowing the binding of the fusion construct to the engineered bacteria etc. in tumor, metal agents (which can be used for detection by MRI, PET or SPECT) are injected intravenously. Binding and absorption of the metal agents by the bacteria etc. will allow indirect tumor detection.

The present invention also relates to a pharmaceutical composition comprising a microorganism or cell containing DNA sequence(s) encoding a cell receptor capable of binding a ligand and furthermore a ligand which is coupled to a toxin (=chimeric toxin). Suitable toxins which can be coupled to the ligand are well known to the person skilled in the art. Several chimeric toxins have been described previously. First, the Tfn-CRM 107 chimeric toxin was prepared by conjugating transferrin to the mutated diphtheria toxin CRM 107 (Johnson et al., J. Neurosurg. 70 (1989), 240-248), which targets the transferrin receptor. Second, the 425.3-PE immunotoxin was prepared by conjugating anti-EGF receptor antibody to the whole *Pseudomonas* exotoxin A (Myklebust et al., Cancer Res. 53 (1993), 3784-3788). Third, the Tfn-PE was prepared by conjugating transferrin to the *Pseudomonas* exotoxin (Hall et al., J. Neurosurg. 76 (1992), 838-844; Hall et al., Neurosurgery 34 (1994), 649-656). It could be shown in animal models and human patients that these chimeric toxins have anti-tumor activities against medulloblastoma, small cell lung cancer, glioma xenografts and intracranial tumors. Thus, e.g. recombinant Vaccinia virus can be designed to specifically express transferrin receptors on the surface of tumor cells allowing the use of these receptor-targeting chimeric toxins for antitumor treatment.

The present invention also relates to a pharmaceutical composition comprising (a) a microorganism or cell containing a DNA sequence encoding a cell receptor capable of binding a ligand and (b) said ligand, which is coupled to a therapeutic protein. Suitable therapeutic proteins as well as methods for generating therapeutic ligand fusion proteins by linking therapeutic proteins to the ligand proteins are well known to the person skilled in the art. Examples of suitable therapeutic proteins are shown in Tables 4 and 5.

TABLE 4

Examples of enzyme/prodrug pairs in which the delivery of the enzyme gene is facilitated by intravenously injected microorganisms and cells:

| Therapeutic proteins (enzymes), drugs, prodrugs | Description | References |
| --- | --- | --- |
| Herpes simplex virus thymidine kinase (HSV-TK) +Ganciclovir (GCV) | Most well-known enzyme/produrg combination. | Moolten Cancer Res. 1986; 46: 5276-5281 |
| Herpes simplex virus thymidine kinase (HSV-TK) +A-5021 (1'S,2'R)-9{[1',2'-bis(hydroxymethyl)cycloprop-1'-yl]methyl}guanine | A-5021 has highly selective antihepatic activity and was selectively phosphorylated by viral TK in herpes virus-infected cells. The anti-herpetic activity of A-5021 was most potent in comparison with ACV and penciclovir. | Hasegawa et al. 2000, Cancer Gene Ther 7: 557-562 |
| Horseradish peroxidase (HRP) +Indole-3-acetic acid (IAA) | When activated by purified HRP, IAA was shown to inhibit colony formation in mammalian cells, whereas, neither enzyme nor prodrug alone was cytotoxic at the same concentration or times. The HRP/IAA-induced cell kill was effective in normoxic and anoxic conditions. | Greco et al. 2000, Cancer Gene Thera. 7: 1414-1420 |

TABLE 4-continued

Examples of enzyme/prodrug pairs in which the delivery of the
enzyme gene is facilitated by intravenously injected microorganisms and cells:

| Therapeutic proteins (enzymes), drugs, prodrugs | Description | References |
| --- | --- | --- |
| Bacterial enzyme carboxypeptidase G2 (CPG2) +4-([2-chloroethyl][2-mesyloxyethyl]amino)benzoyl-L-glutamic acid (CMDA) or +4-[N,N-bis(2-iodoethyl) amino] phenoxycarbonyl L-glutamic acid (ZD2767P) | CPG2 can be expressed both intracellularly or tethered to the outer surface of mammalian cells, where it is able to activate mustard prodrugs for use in suicide gene therapy. | Spooner et al. 2000, Cancer Gene Ther. 7: 1348-1356 Webley et al. 2001, Br J Cancer 84: 1671-1676 |
| Human cytochrome P450 CYP1A2 +acetaminophen | Acetaminophen is cytotoxic through the cytochrome P450-mediated generation of a chemically reactive metabolite, N-acetylbenzoquinoneimine (NABQI). | Thatcher et al. 2000, Cancer Gene Ther 7: 521-525 |
| Rabbit cytochrome P450 4B1 (CYP4B1) +4-ipomeanol (4-IM) | CYP4B1 is able to induce tumor cell death at low micromolar concentrations in glioblastoma cells after treatment with the prodrug 4-IM. | Mohr et al. 2000, Cancer Gene Ther. 7: 1008-1014; Steffens et al. 2000, Cancer Gene Ther 7: 806-812 |
| Rat cytochrome P450 4B1 (CYP2B1) +oxaphosporines, such as ifosfamide (IFO) | The CYP2B1 gene product activates oxaphosphorines to the hydroxy form, giving rise to the toxic products phosphamide mustard and acrolein, which alkylate DNA and proteins, respectively. | Kammertoens et al. 2000, Cancer Gene Ther 7: 629-636 |
| E. coli nitroreductase (NTR) +CB1954 | CB1954 is a weak monofunctional alkylating agent that is converted by NTR into 2- and 4-hydroxylamino derivatives. Cellular thioesters such as acetyl coenzyme A subsequently convert the latter into a powerful bifunctional alkylating agent that can kill both proliferating and nonproliferating cells. PTX0147 is the plasmid expressing NTR from the human cytomegalovirus (CMV) early promoter/enhancer and also carries the b-globin second intron and poly (A) sequences and a G418 selectable marker. | Djeha et al. 2000, Cancer Gene Ther. 7: 721-731; Djeha et al. 2001, Mol Ther 3: 233-240 Westphal et al. 2000, Cancer Gene Ther 7: 97-106 Weedon et al. 2000, Int J Cancer 86: 848-854 |
| E. coli cytosine deaminase (CD), E. coli uracil phosphoribosyltransferase (UPRT) +5-fluorocytosine (5-FC) | Despite CD expression, a number of tumor cells were 5-FC-resistant, which may be attributable to the lack of an active cytosine transport system in mammalian cells and to the degradation of the formed 5OFU by dihydropyrimidine dehydrogenase (DPD). In the gene transfer strategy, to improve the effect of the CD/5-FC system, it might be possible to transduce the enzyme gene that converts 5-FU to its active forms. One of the candidates is E. coli UPRT. It is a pyrimidine salvage enzyme and is characteristic to bacteria. It directly converts 5-FU to 5-fluorouridine monophosphate (FUMP) at the first step of 5-FU activation and has the potential to enhance the activating pathway against DPD. | Koyama et al. 2000, Cancer Gene Ther. 7: 1015-1022; Theys et al. 2001, Cancer Gene Ther 8: 294-297; Kammertoens et al. 2000, Cancer Gene Ther 7: 629-636; Block et al. 2000, Cancer Gene Ther 7: 438-445; Bentires-Alj et al. 2000 Cancer Gene Ther 7: 20-26; Kawamura et al. 2000, Cancer Gene Ther 7: 637-643; Li et al. 1997, Cancer Gene Ther 4: 113-117 |

TABLE 4-continued

Examples of enzyme/prodrug pairs in which the delivery of the
enzyme gene is facilitated by intravenously injected microorganisms and cells:

| Therapeutic proteins (enzymes), drugs, prodrugs | Description | References |
| --- | --- | --- |
| Cytochrome P450 enzymes +cyclophosphamide (CPA) | Liver tissue has a high content of P450 enzymes active toward CPA and is the major organ responsible for CPA activation. Activated CPA generated in the liver circulates through the blood and gains entry to tumor tissue to exert its therapeutic effects. Intratumoral CPA activation can result in a high, localized concentration of active drug metabolite at its site of action, which may maximize therapeutic effects while at the same time minimizing the host toxicities associated with hepatic drug activation. | Huang et al. 2000, Cancer Gene Ther. 7: 1034-1042; Kan et al. 2001, Cancer Gene Ther 8: 473-482 |
| rabbit carboxylesterase +7-ethyl-10-[4-(1-piperidino)-1-piperidino] carbonyloxycamp-tothecin (CPT-11) | Exposure of neuroblastoma cell lines or of mixtures of these cell lines with CD34(+) cells at a ratio of 10:90 to replication-deficient AdRSVrCE for 24 h and subsequent exposure of cells to 1-5 microM CPT-11 for 4 h increased the toxicity of CPT-11 to three Neuroblastoma cell lines (SJNB-1, NB-1691, and SK-N-SH) from approximately 20-50-fold and eradicated their clonogenic potential. | Meck et al. 2001, Cancer Res 61: 5083-5089 |
| Mushroom tyrosinase +bis-(2-chloroethyl)amino-4-hydroxyphenylaminomethanone 28 | A sterically undemanding prodrug bis-(2-chloro-ethyl)amino-4-hydroxyphenylaminomethanone 28 was synthesised and found to be oxidised by mushroom tyrosinase at a superior rate to tyrosine methyl ester, the carboxylic acid of which is the natural substrate for tyrosinase. | Jordan et al 2001, Bioorg Med Chem 9: 1549-1558 |
| *E. coli* β-galactosidase +1-chloromethyl-5-hydroxy-1,2-dihydro-3H benz[e]indole (CC-1065) or +1-(1'-chloroethyl)-5-hydroxy-1,2-dihydro-3H-benz[e]indole | Prodrug cleaved by galactosidase shows high cytotoxicity towards human bronchial carcinoma cells of line A549. | Tietze et al. 2001, Chembiochem 2: 758-765 |
| A mutant of carboxypeptidase G2 (CPG2, glutamate carboxypeptidase +4-[bis(2-iodoethyl)amino]-phenyloxycarbonyl-L-glutamic acid or +3-fluoro-4-[bis(2-chlorethyl)amino]benzoyl-L-glutamic acid or +3,5-difluoro-4-[bis(2-iodoethyl)amino]benzoyl-L-glutamic acid | Activation of all three of the prodrugs not only kills the cells expressing the mutant CPG2 on the surface but also the neighboring cells through by-stander effect. | Friedlos et al. 2002, Cancer Res 62: 1724-1729 |

Note:
The content of this table is by no-means to be exhaustive. Any other similar enzyme-prodrug pairs, which are not listed in this table, are also considered to be included.

TABLE 5

Further examples of therapeutic proteins that can be used for BMPT (bacterium-mediated protein therapy), VMPT (virus-mediated protein therapy) or CMPT (cell-mediated protein therapy), e.g. mCMPT (mammalian-cell-mediated protein therapy), against tumors:

| Therapeutic proteins, drugs | Description | References |
|---|---|---|
| rsCD40L | Ligand of CD40, sensitizing tumor cells to apoptosis induced by a variety of agents, including TNF-alpha, anti-Fas, and cytotoxic drugs. | Eliopoulos et al. 2000, Mole. Cell. Biol. 20: 5503-5515 |
| Fas-ligand | | Sharma et al. 2000, Pharmacol Ther. 88: 333-347 |
| TRAIL | Ligand for death receptors such as DcR2, DcR1, DR5, DR4. | Golstein 1997, Curr. Biol. 7: R750-753. |
| TNF | TNF is the ligand for TNFR1, which mediates cell-death signaling. | Baker and Reddy 1996, Oncogene 12: 1-9; Theys et al. 1999, Appl Environ Microbiol 65: 4295-4300; Lammertyn et al. 1997, Appl Environ Microbiol 63: 1808-1813 |
| Recombinant antibodies | | |
| Anti-GA733-2 | Secreted or membrane-anchored form of monoclonal antibody (mAb) (CO17-1A) specific for Ag (GA733-2) that is present on the surface of most gastrointestinal carcinomas. | Paul et al. 2000, Cancer Gene Ther 7: 615-623 |
| Anticancer drugs adriamycin (ADM), cytosine arabinoside (Ara-C), cisplatin, doxorubicin, mitomycin C, fluorouracil, campto-thecin, cis-diammine-dichloroplatinum (II), CDDP, etc. +anti-Fas antibody | Some tumor cells express Fas antigen on their surface, and apoptosis is induced in those cells by IgM-anti-Fas MoAb. Clinically relevant concentrations of anticancer drugs enhance Fas receptor expression on the plasma membrane of tumor cells. By the combination of ADM or Ara-C with IgM-anti-Fas MoAb, the induction of apoptosis in HL60 leukemic cells was enhanced significantly. Therefore, we may use bacteria or viruses to deliver the gene encoding anti-Fas antibody. Expression of the anti-Fas antibody on the surface of tumor cells may sensitizes these cells to chemotherapy agents, which therefore may improve the efficiency of chemotherapy. | Nakamura et al. 1997, Anticancer Res. 17: 173-179; Micheau et al. 1997, J. Natl. Cancer Inst. 89: 783-789; Chang et al. 1998, Osaka City Med. J. 44: 173-180; Mizutani et al. 1997, Cancer 79: 1180-1189; Jiang et al. 1999, Hepatology 29: 101-110; Mizutani et al. 1998, J. Urol. 160: 561-570 |
| Bacterial toxins | | |
| Microcin E492 | A low-molecular mass channel-forming bacteriocin (7,887 Da) produced by *Klebsiella pneumoniae*. It has been shown that microcin E492 induces apoptosis in certain human cell lines. Treatment with zVAD-fmk, a general caspase inhibitor, completely blocked the cytotoxic effect of this bacteriocin, which may provide a safety mechanism when microcin is used in anti-tumor treatment. Microcin-E492-insensitive mutants of *E. coli* K12 have been isolated, which may be used as a carrier to deliver microcin (Pugsley et al. 1986, J Gen Microbiol 132: 3253-3259). | de Lorenzo 1984, Arch Microbiol 139: 72-75; Hetz et al. 2002, Proc Natl Acad Sci USA 99: 2696-2701 |
| diphtheria toxin (DT) | Toxin-labeled monoclonal antibodies have been used to target tumor cell surface receptors for cell killing (Kreitman | |

TABLE 5-continued

Further examples of therapeutic proteins that can be used for BMPT (bacterium-mediated protein therapy), VMPT (virus-mediated protein therapy) or CMPT (cell-mediated protein therapy), e.g. mCMPT (mammalian-cell-mediated protein therapy), against tumors:

| Therapeutic proteins, drugs | Description | References |
|---|---|---|
| | 2001, Curr Pharm Biotechnol 2: 313-325; Thomas et al. 2002, J Pediatr Surg 37: 539-544). Toxin-label protein ligands have also been used to target cell surface receptors (Olson et al. 1997, Int J Cancer 73: 865-870; Arora et al. 1999, Cancer Res 59: 183-188; Wild et al. 2000, Br J Cancer 83: 1077-1083). | |
| *Pseudomonas* exotoxin | | |
| *Escherichia coil* Shiga toxins | Shiga toxins, Shiga-like toxin I (SLT-I) and Shiga-like toxin II (SLT-II) are cell-associated cytotoxins, which have been shown to be able to kill tumor cells. The toxins kill target cells by inducing apoptosis. | O'Brien et al. 1992, Curr Top Microbiol Immunol 180: 65-94; Nakao and Takeda 2000, J Nat Toxins 9: 299-313 |
| *Escherichia coli* Vero-toxin 1 (VT1) | VT1 is an *E. coli* elaborated subunit toxin active only against (tumor) cell lines that express the VT1 receptor, globotriaosyl ceramide-Gb3. In an example of VT1 action, it has been shown that VT1 eliminates human astrocytoma xenograft in nude mice. | Farkas-Himsley et al. 1995, Proc Natl Acad Sci USA 92: 6996-7000; Arab et al. 1999, Oncol Res 11: 33-39 |
| Plant toxins | | |
| Hyperforin | Hyperforin is a plant derived antibiotic. It was shown that hyperforin can inhibit tumor growth by activating mitochondria-mediated apoptosis pathway. | Hostanska et al. 2002, Pharmazie 57: 323-331; Schempp et al. 2002, Oncogene 21: 1242-1250 |

Note:
The content of this table is by no-means to be exhaustive. Any other similar therapeutic proteins, which are not listed in this table, are also considered to be included.

Since the tutor tissues can be labeled with ligand receptors using intravenously injected engineered bacteria, viruses or cells, the binding of therapeutic-ligand fusion proteins to the ligand receptors will enable the targeting of the therapeutic proteins to the tumor tissues. Intracellular bacteria and viruses are particularly useful in labeling the tumor cell surface with designated receptor proteins. However, due to "bystander effect" of therapeutic proteins on neighboring cells, extracellular bacteria and mammalian cells can also be used to deliver the therapeutic proteins.

In the case of Gene-Directed Enzyme Prodrug Therapy (GDEPT) (see below), for example, extracellular bacteria may be used to secrete the enzyme-ligand fusion protein. The tumor cell surface may be labeled with receptor proteins by viruses. After the intravenous delivery of prodrug, not only the cells expressing the receptors will be bathed with and killed by the active drug, the surrounding tumor cells (which may not be labeled with receptors) will also be killed.

Viruses (such as Vaccinia virus) may also be used to label the tumor cell surface with receptor proteins. For example, the tumor tissues can be specifically infected by intravenously injected engineered Vaccinia virus carrying, e.g., a transferrin receptor gene (also encoding a single peptide for cell surface expression). Expression of the transferrin receptor on the tumor cell surface will mark these cells for targeting by therapeutic-ligand fusion proteins. In this case, the ligand is the transferrin protein, and the therapeutic protein could be a *Pseudomonas* exotoxin (or any other cytotoxic therapeutic proteins). Tumor cell internalization of the transferrin/transferrin receptor pair allows the internalization of the therapeutic protein, which in turn delivers the cytotoxicity specifically to the tumor cells. Transferrin/transferrin receptor pair is only one of many examples of ligand-receptor pairs that can be used. In addition, mutant ligands and mutant receptors with highly specific affinity toward each other may be used to avoid the binding to endogenous proteins.

Additional examples of suitable proteins are human endostatin and the chimeric PE37/TGF-alpha fusion protein. Endostatin is a carboxyterminal peptide of collagen XVIII which has been characterized (Ding et al., PNAS USA 95 (1998), 10443). It has been shown that endostatin inhibits endothelial cell proliferation and migration, induces G1 arrest and apoptosis of endothelial cells in vitro, and has antitumor effect in a variety of tumor models. Intravenous or intramuscular injection of viral DNA and cationic liposome-complexed plasmid DNA encoding endostatin result in limited expression levels of endostatin in tumors. However intratumoral injection of purified endostatin shows remarkable inhibition of tumor growth. *Pseudomonas* exotoxin is a bacterial toxin secreted by *Pseudomonas aeruginosa*. PE elicits its cytotoxic effect by inactivating elongation factor 2 (EF-2), which results in blocking of protein synthesis in mammalian cells. Single chain PE is functionally divided into three domains: domain Ia is required for binding to cell surface receptor, domain II is required for translocating the toxin into the target cell cytosol, and domain III is responsible for cytotoxicity by inactivating EF-2. PE40 is derived from wild type Pseudomonas exotoxin that lacks the binding domain Ia. Other proteins such as antibody fragments or protein ligands can be inserted in place of the binding domain. This will render the PE40-ligand fusion protein specific to its receptor. One of the highly specific engineered chimeric toxins is the TGF alpha/PE40 fusion protein, where the C-terminus of TGF alpha polypeptide has been fused in frame with the N-terminus of the PE40 protein. TGF alpha is one of the ligands of epidermal growth factor receptor (EGFR), which has been shown to be preferentially expressed on the surface of a variety of tumor cells. TGF alpha-PE40 fusion protein has been shown to be highly toxic to tumor cells with elevated EGYRs on the cell surface and while it is less toxic to nearby cells displaying fewer numbers of surface EGFR. The toxicity of TGF alpha-PE40 chimeric protein is dependent on a proteolytic processing step to convert the chimeric protein into its active form, which is carried out by the target. To overcome the requirement for proteolysis, a new chimeric toxin protein that does not require processing has been constructed by Theuer and coworkers (J. Biol. Chem. 267 (1992), 16872). The novel fusion protein is termed PE37/TGF alpha, which exhibited higher toxicity to tumor cells than the TGF alpha-PE40 fusion protein.

In a particular preferred embodiment of the diagnostic and/or pharmaceutical composition of the present invention the ligand is not the naturally occurring ligand but any compound which is capable of specifically binding to the receptor, e.g. an antibody. The term "antibody", preferably, relates to antibodies which consist essentially of pooled monoclonal antibodies with different epitopic specificities, as well as distinct monoclonal antibody preparations. Monoclonal antibodies are made from an antigen containing fragments of the particular receptor by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab')2 fragments) which are capable of specifically binding to a receptor. Fab and F(ab')2 fragments lack the Fc fragment of intact antibody, clear more rapidly from the circulation, and may have less non-specific tissue binding than an intact antibody (Wahl et al., J. Nucl. Med. 24:316-325 (1983). Thus, these fragments are preferred, as well as the products of an FAB or other immunoglobulin expression library. Moreover, antibodies of the present invention include chimeric, single chain, and humanized antibodies.

Antibody-ligands are, e.g., useful in anti-tumor therapy using fusion proteins (i.e. immunotherapeutic proteins) between antibodies and therapeutic proteins: Firstly, the genes encoding cell surface receptors are delivered to tumors cells in live organisms via intravenously injected engineered bacteria and viruses. Such receptors can be, e.g., transferrin receptor, EGF receptor, somatostatin receptor, etc. over-expression of receptors on the cell surface following bacterial or viral infections will be used to mark the tumor cells. Secondly, a fusion protein (an immunotherapeutic protein) between an antibody, preferably an antibody fragment, (specific to the overexpressed surface receptors) and a therapeutic protein (e.g. any type of toxins, see Table 5) is prepared. The intravenously injected fusion protein may bind to the marked tumor cells and exhibit cytotoxicity toward these cells in the tumor tissues.

The present invention also relates to a diagnostic and/or pharmaceutical composition containing a microorganism or cell as described above and furthermore (a) an antimicrobial compound fused to a protein suitable for tumor therapy and/or elimination of metastatic tumors and/or (b) an antimicrobial compound fused to a detectable protein or a protein capable of inducing a detectable signal. Anti-tumor therapy using such fusion proteins between antimicrobial compounds (e.g. peptides/proteins) and therapeutic proteins can be carried by firstly preparing fusion gene constructs encoding hybrid proteins between antimicrobial peptides/proteins and therapeutic proteins (see Table 5, above). After protein expression, the hybrid proteins are purified and ready for intravenous injection. Secondly, e.g. light-emitting bacteria, which can be recognized and bound by the antimicrobial peptides/proteins, are injected intravenously into the subject for tumor-specific accumulation. The specific binding of antimicrobial peptides/proteins to bacteria in the tumors helps to concentrate therapeutic proteins specifically in the tumors, which therefore may elicit tumor specific cytotoxicity.

Furthermore, the protein suitable for tumor therapy and/or elimination of metastatic tumors can be an enzyme converting an inactive substance (prodrug) administered to the organism into an active substance, i.e. toxin, which kills the tumor or metastasis (Gene-Directed Enzyme Prodrug Therapy (GDEPT)). The principle of GDEPT is that an enzyme/protein activates a systemically delivered nontoxic prodrug into active toxic drug, which is cytotoxic to tumors. To be specific, GDEPT is a two-step treatment. In the first step, the gene encoding a foreign enzyme is administered and directed to the tumor, where it may be expressed using specific transcriptional elements. In the second step, prodrugs are administered and activated by the foreign enzyme expressed at the tumor. If the enzyme/proteins are present only in the tumors, the active drugs will also be produced only in the tumors, and therefore exhibit cytotoxicity only toward the tumor cells, while at the same time, systemic toxicity is kept to a minimum. The gene encoding enzyme/protein is delivered specifically to the tumors using intravenously injected engineered bacteria, viruses, or (mammalian) cells according to the present invention. These genes can be under the control of either constitutive promoters or exogenously regulated inducible promoters additionally ensuring that the conversion of the prodrug into the toxin only occurs in the target tissue, i.e. tumor. Such promoters are e.g. IPTG-, antibiotic-, heat-, pH-, light-, metal-, aerobic-, host cell-, drug-, cell cycle- or tissue specific-inducible promoters.

For example, the enzyme can be glucuronidase converting the less toxic form of the chemotherapeutic agent gluctronyl-doxorubicin into a more toxic form. Preferably, the gene encoding such an enzyme is directed by a promoter which is a constitutive or inducible promoter Further examples of enzyme/prodrug pairs which are useful in the pharmaceutical composition of the present invention are listed in Table 4, above.

Moreover, the delivery system of the present application even allows the application of compounds which could so far not be used for tumor therapy due to their high toxicity when systemically applied. Such compounds include proteins inhibiting elongation factors, proteins binding to ribosomal subunits, proteins modifying nucleotides, nucleases, proteases or cytokines (e.g. IL-2, IL-12 etc.), since experimental data suggest that the local release of cytokines might have a positive effect on the immunosuppressive status of the tumor.

Furthermore, the microorganism or cell can contain a BAC (Bacterial Artificial Chromosome) or MAC (Mammalian Artificial Chromosome) encoding several or all proteins of a specific pathway, e.g. antiangiogenesis, apoptosis, wound-healing or anti-tumor growth. Additionally the cell can be a computer-designed cyber cell or cyber virus encoding these proteins in multiple combinations.

For administration, the microorganisms or cells of the present invention are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the microorganisms or cells may be effected by different ways, e.g. by intravenous, intraperitoneal, subcutaneous, intramuscular, topical or intradermal administration. The preferred route of administration is intravenous injection. The route of administration, of course, depends on the nature of the tumor and the kind of microorganisms or cells contained in the pharmaceutical composition. The dosage regimen will be determined by the attending physician based on various clinical factors. As is well known in the medical arts, dosages for any one patient depends on many factors, including the patient's size, body surface area, age, sex, the particular compound to be administered, time and route of administration, the kind, size (and localization of the tumor, general health and other drugs being adminstered concurrently.

Preferred tumors that can be treated with the microorganisms or cells of the present invention are bladder tumors, breast tumors, prostate tumors, brain tumors, colon tumors, lung tumors, ovarial carcinomas, and pancreatic carcinomas; liver tumors, skin tumors.

C6 glioma cells ($5\times10^5$) were implanted subcutaneously into the right lateral thigh of nude mice. Ten days after tumor cell implantation, the animals were infected intravenously with $1\times10^8$ pfu of rVV-ruc-gfp. GFP expression was monitored 7 days post-viral injection. Vascularization at the surface of the subcutaneous C6 glioma tumor is shown against the bright green fluorescent background in the tumor following Vaccinia-mediated gene expressions. Bright field (A), fluorescence (B), and bright field, fluorescence overlay (C) images of subcutaneous glioma tumor are illustrated. (Bars=5 mm.)

Figure 3:
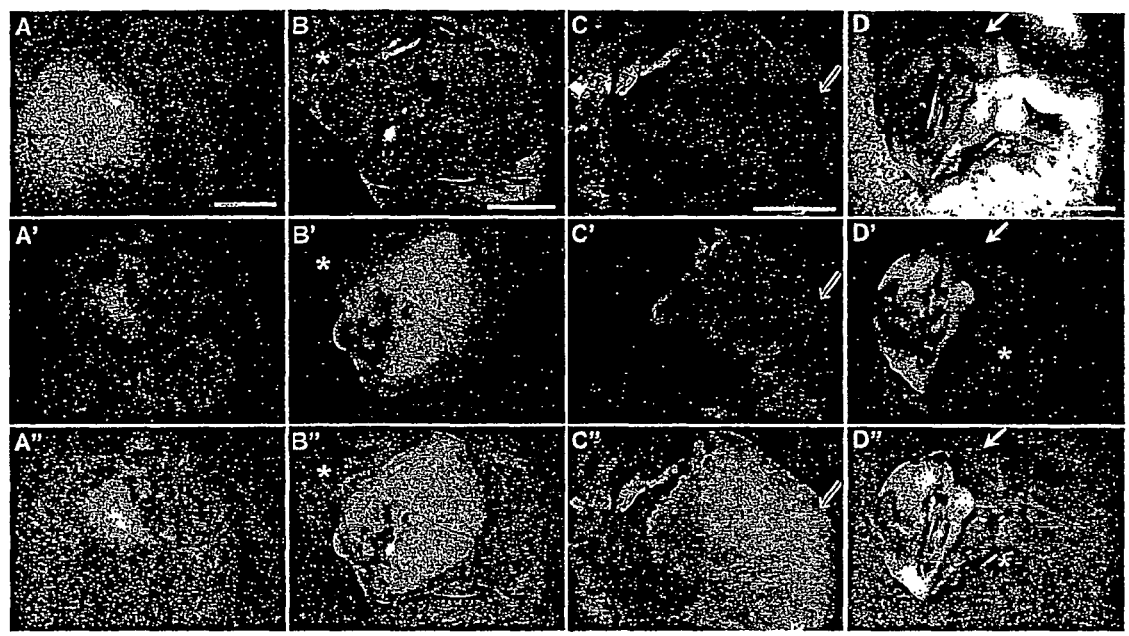

FIG. 3: Expression of GFP in subcutaneous glioma tumor of the same animal

Five days after the subcutaneous implantation of $5\times10^5$ C6 glioma cells into the right lateral thigh, $10^8$ of rVV-ruc-gfp virus particles were injected intravenously. Five days after viral injection, the animal was anesthetized and sacrificed for analysis of GFP expression under fluorescence microscope. The tumor was visualized externally (A-A"), with the overlying skin reflected (B-B"), in cross section (C-C"), and in the amputated leg (D-D"). Bright field (A), fluorescence (B), and bright field, fluorescence overlay (C) images of subcutaneous glioma tumor are illustrated. The strongest GFP expressions are seen as patches located along the outer surface of the tumor on the right (double arrows in C-C"). Sharp difference of GFP expression in tumor tissue and in the normal muscle tissue (arrows in D-D") is clearly visible. Asterisks mark the reflected skin (B-B" and D-D"). (Bars=5 mm.)

Figure 4:
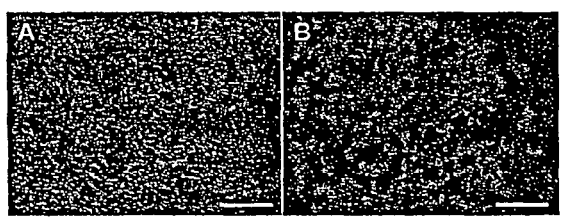

FIG. 4: Bright field (A) and fluorescence (B) images of tumor cells expressing GFP Frozen sections (30 µm thick) of the glioma tumor tissues were prepared from a nude mouse that has been intravenously injected with $1\times10^8$ of rVV-ruc-gfp virus particles. (Bars=50 Wm.)

Figure 5:
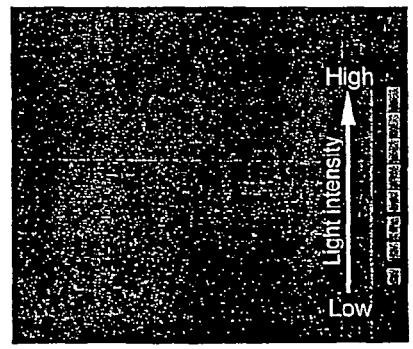

FIG. 5: Low light image of the anesthetized nude mouse to indicate the location of *Renilla* luciferase-triggered light emission in the presence of intravenously injected substrate coelenterazine (5 µg ethanol solution)

Figure 6:
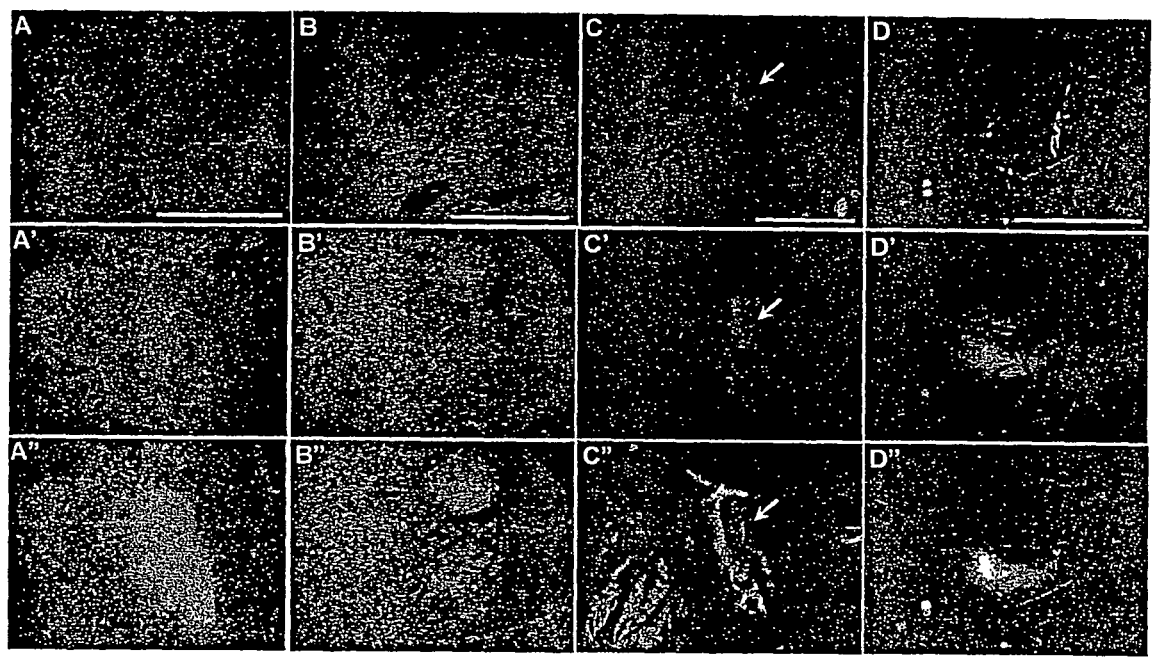

FIG. 6: Monitoring tumor-specific viral infection based on GFP gene expression in a variety of tumor models including subcutaneous PC-3 human prostate tumor (A-A") and MCF-7 human breast tumor (B-B") in nude mice, intracranial C6 rat glioma tumor (C-C", arrows indicate the location of the tumor) in Lewis rats, and MB-49 mouse bladder tumor (D-D") in C57 mice. Animals were monitored 7 days after intravenous injections of $1\times10^9$ of rVV-ruc-gfp virus particles. Bright field (top), fluorescence (middle), and bright field, fluorescence overlay (bottom) images of the tumor are illustrated. (Bars=5 mm.)

Figure 7:
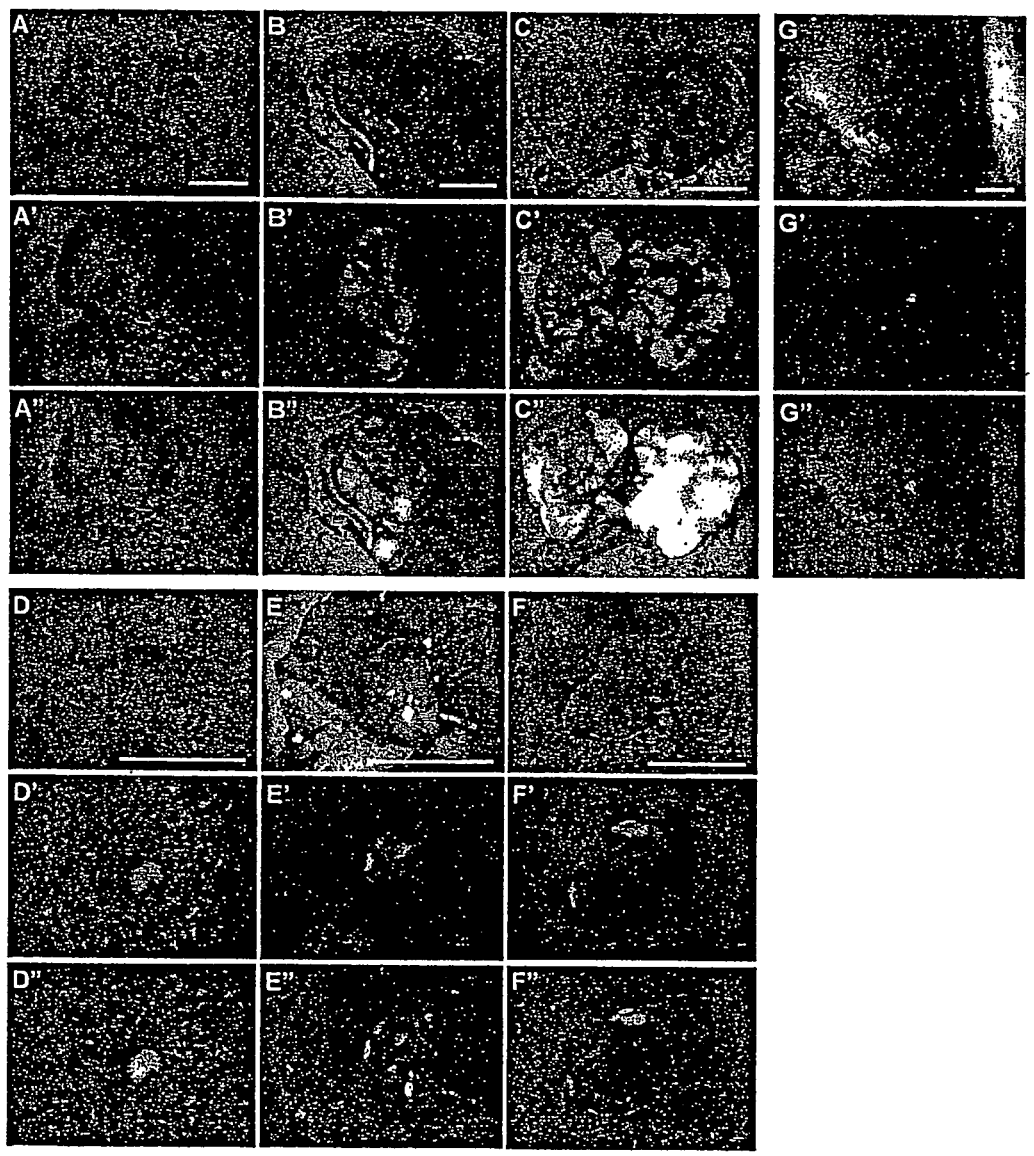

FIG. 7 Monitoring Vaccinia-mediated GFP expression in a breast tumor model

Nude mouse carrying breast tumor was injected intravenously with $1\times10^8$ of rVV-ruc-gfp virus particles. Both the primary tumor (A-A", B-B", and C-C") and the metastasized tumor (D-D", E-E", and F-F") were visualized externally (A-A" and D-D"), with overlying skin removed (B-B" and E-E"), and when they were split open (C-C" and F-F') in a set of bright field, fluorescence (') and bright field, fluorescence overlay (") images. GFP expression in lung metastases in the same animal was also visualized (G-G"). (Bars=5 mm (A-A" to F-F"), and Bars 1 mm (G-G")

Figure 8:
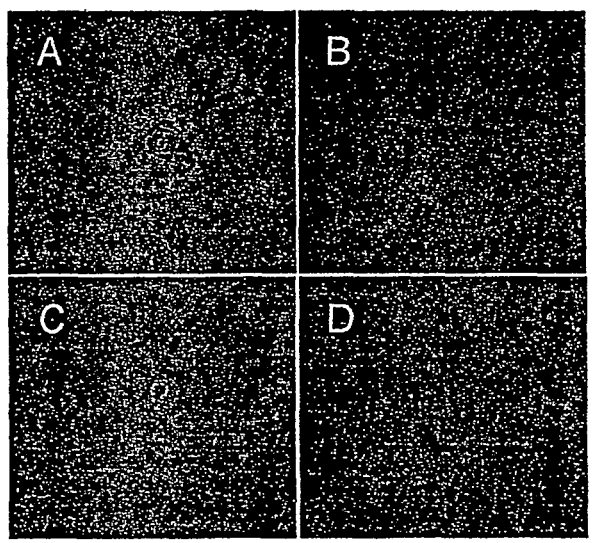

FIG. 8: Visualization of the clearance of light emitting bacteria from nude mice based on the detection of light emission under the low light imager Nude mice were intravenously injected with $10^7$ cells of attenuated *S. typhimurium* (A, B) and *V. cholera* (C, D). Both strains were transformed with pLITE201 carrying the lux operon. Photon collection was done 20 min (A, C) and 2 days (B, D) after bacterial injections.

Figure 9:
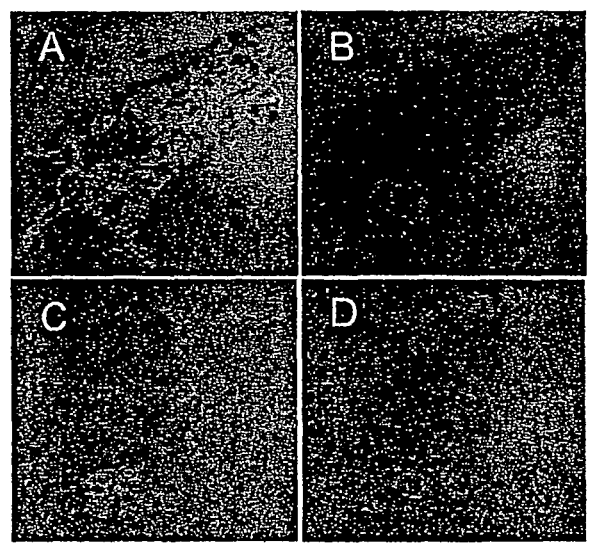
Figure 9:
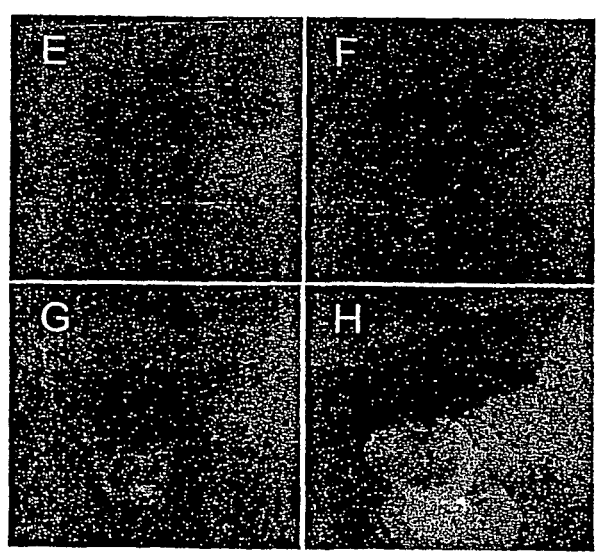

FIG. 9: Homing of glioma tumors by attenuated bacteria

Nude mice with a C6 glioma tumor in the right hind leg were intravenously injected with $10^7$ attenuated *S. typhimurium* (A-D) and with *V. cholera* (E-H) both transformed with pLITE201 plasmid DNA encoding the lux operon. Photon collection was carried out for one minute under the low light imager. Mice injected with *S. typhimurium* exhibited luminescence immediately through the whole animal (A). In contrast, luminescence in the mice injected with *V. cholera* was visible in the liver area (E). Two days after bacterial injection, both groups of mice demonstrated luminescence only in the tumor region (B, F). The light emission in the tumors infected with *S. typhimurium* slowly diminished four (C) and six (D)

days after bacterial injection. Tumors infected with *V. cholera* showed enormously increased light emission four (G) and six (H) days after injection suggesting continued replication of the bacteria in the tumor tissues.

Figure 10:
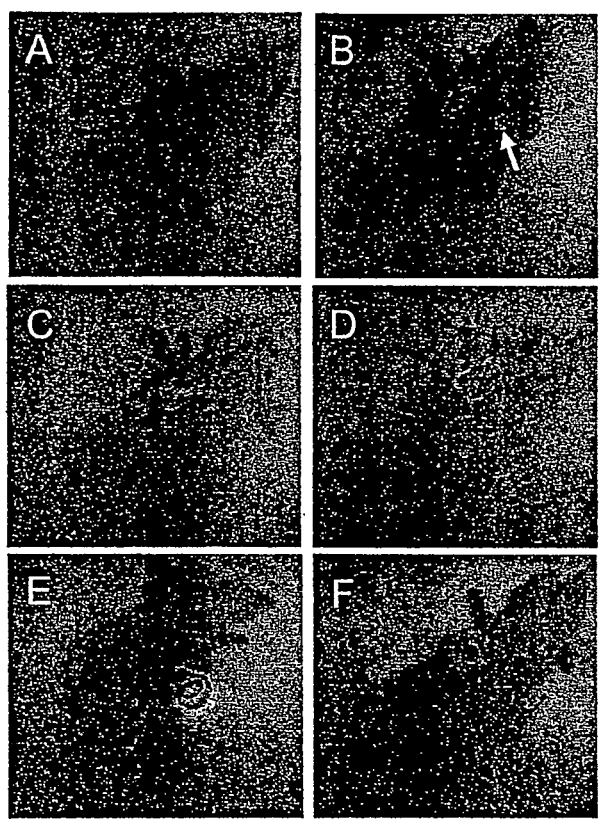

FIG. 10: Homing in of bacteria to breast tumors

Nude mice with breast tumors in the right breast pad were intravenously injected with $10^7$ attenuated *V. cholera* (A-D) or with $10^7$ *B. coli* (E-F) transformed with pLITE201 plasmid DNA encoding the lux operon. Photon collection was carried out for one minute under the low light imager. Twenty minutes after (bacterial delivery, luminescent *V. cholera* were observed in the liver (A). Forty-eight hours after injection, light emission was noted in the primary breast tumor in the right breast area and a metastatic tumor (arrow) in the left breast area, and in the incision wound (B). At five days, the light emission was visible only in the tumor regions, and not at the wound (C). Eight days after bacterial injection, the luminescent activity was abolished from the smaller tumor region but remained strong in the primary breast tumor (D). Homing in of *E. coli* to breast tumors in nude mice was also observed two days after intravenous bacterial injection (E: side view, F: ventral view).

Figure 11:
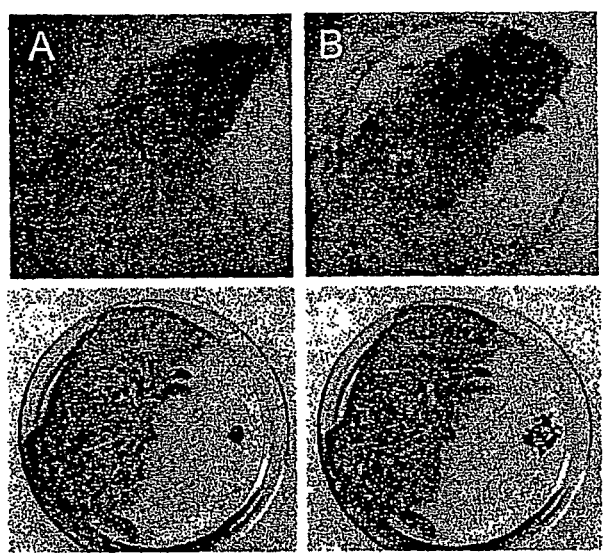

FIG. 11: Homing in of bacteria to bladder tumors in C57 mice

C57 mice were intravenously injected with $10^7$ attenuated *V. cholera* transformed with pLITE201 encoding the lux operon. Nine days after bacterial delivery, luminescence was noted in the bladder region of the whole animal (A). The animal was sacrificed and an abdominal incision was made to expose the bladder. The light emission was limited to the bladder region (B). With the removal of the bladder (C) from the mouse, the entire source of light emission was removed (D) as demonstrated by the overlay of the low light photon emission image over the photographic image of the excised bladder.

Figure 12:
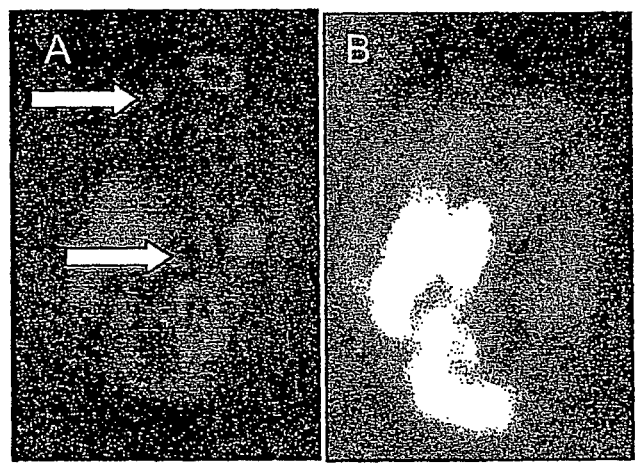

FIG. 12: Homing in of bacteria to brain glioma tumors in Lewis rats

Lewis rats were intravenously injected with $10^8$ cells of attenuated *V. cholera* transformed with pLITE201 encoding the lux operon. Twenty-four hours after bacterial injection, faint luminescence was noted in the head region of the whole animal during visualization under the low light imager. The animals were sacrificed and their brain removed. Photon collection was carried out for one minute from rats with (A) and without (B) brain tumors. Strong luminescence was confirmed in regions of the brain of the rats with the brain tumor (marked with arrows in A). Luminescence was completely absent in the control brain tissues (B).

Figure 13:
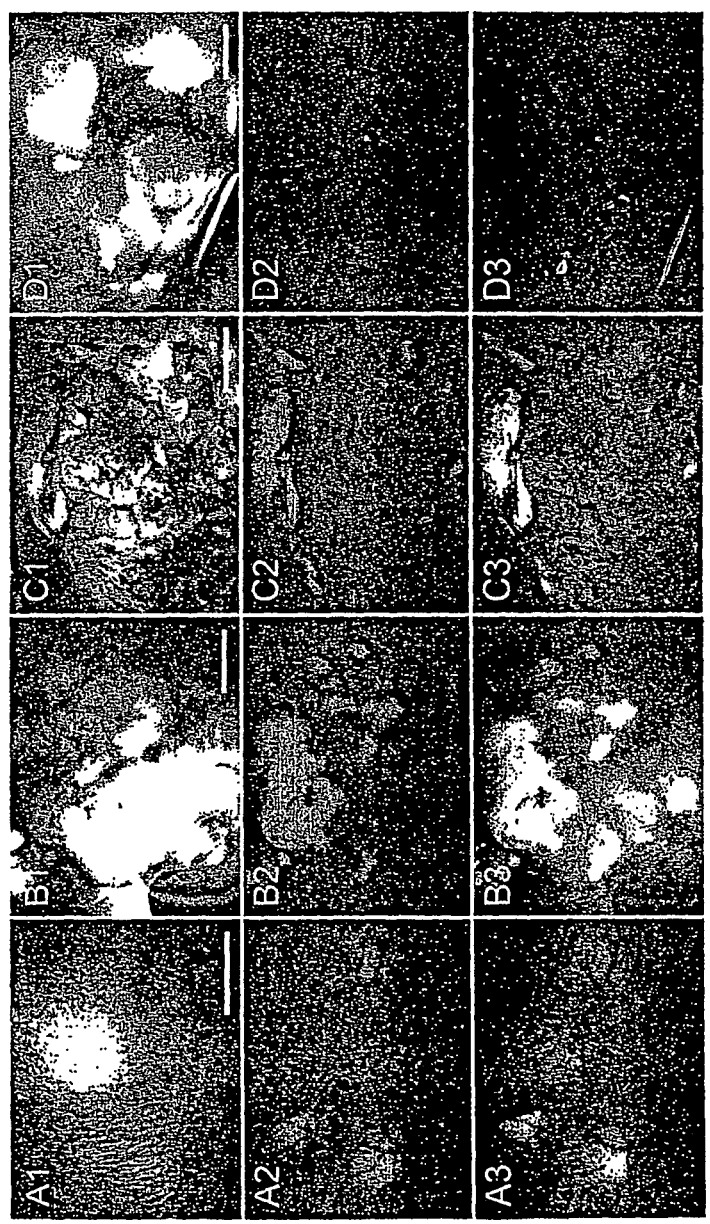

FIG. 13: Transformed human fibrosarcoma cells home in on subcutaneous glioma tumors in nude mice Nude mice with subcutaneous glioma tumors were injected intravenously with $5\times10^5$ human fibrosarcoma cells, which were permanently transformed with retrovirus derived from pLEIN. Seven days post-injection, the animals were anesthetized and monitored under a fluorescent stereomicroscope. Fluorescent cells were noted only in the tumor region of the whole mice through the skin (A1-3). Upon exposure of the tumor tissues by reflection of the overlying skin (B1-3), and in cross sections of the tumors (C1-3), fluorescent patches were visible in distinct regions. Close examination of the organs of the mice showed the presence of small clusters of fluorescent cells in the lungs of the animals, demonstrating the affinity of the fibrosarcoma cells for the lungs in addition to the tumorous tissues (D1-3). (Bars=5 mm (A1-C3), =1 mm (D1-D3)).

Figure 14:
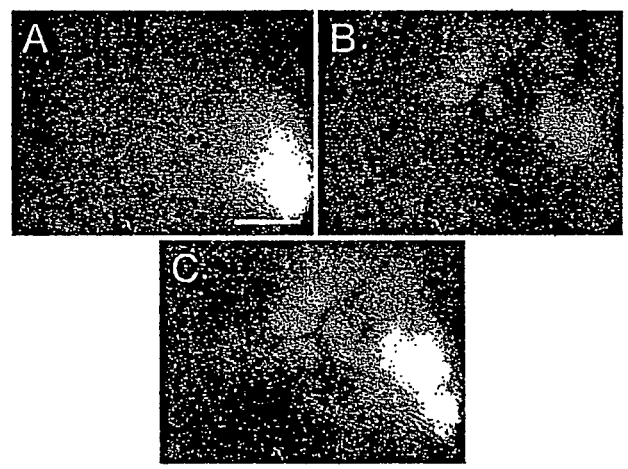

FIG. 14: Homing of attenuated *Listeria* monocytogene into subcutaneous prostate tumors Nude mice with subcutaneous human PC3 prostate tumor in the right hind leg were intravenously injected with $10^7$ attenuated *L. monocytogenes* transformed with psod-gfp plasmid DNA carrying the gfp cDNA, GFP fluorescence was observed under a fluorescence stereo microscope. Twenty-seven hours after bacterial injection, GFP signal was detected only in the tumor region. The tumor is shown in a set of visible light (a), fluorescent (b), and visible and fluorescent light overlay (C) images. (Bars=5 mm.)

DETAILED DESCRIPTION OF THE INVENTION

The present invention is explained by the examples.

Example 1

Materials and Methods (A) Bacterium Strains.

The bacterial strains used were attenuated *Salmonella typhimurium* (SL7207 hisG46, DEL407[aroA544::Tn10]), attenuated *Vibrio cholerae* (Bengal 2 Serotyp 0139, M001 DattRS1), and attenuated *Listeria monocytogenes* (D2 mpl, actA, plcB) The bacterial strains were kindly provided by Prof. W. Göbel (University of Würzburg, Germany).

(B) Plasmid Constructs.

The plasmid pLITE201 containing the luxCDABE cassette was obtained from Dr. Marines, Biotech 24, 1998, 56-58). The plasmid pXylA-dual with the operon sequence of gfp-cDNA, lux AB, lux CD, and lux E under the control of the Xylose promoter was kindly provided by Dr. Phil Hill (University of Nottingham, UK).

(C) Transformation of Bacteria

The bacteria were transformed by electroporation.

(D) Tumor Cell lines. The rat C6 nitrosourea-induced glioma cell line (ATCC, Rockville, Md.) was cultured in RPMI-1640 medium (Cellgro®, Mediatech, Inc., Herndon, Va.) supplemented with 10% (v/v) FBS and 1× penicillin/streptomycin. The human PC3 prostate carcinoma cell line (ATCC, Rockville, Md.) and the MB-49 mouse bladder tumor cells and rat 9 L glioma cells were maintained in DMEM medium (Cellgro®, Mediatech, Inc., Herndon, Va.) supplemented with L-glutamine and 10% (v/v) FBS. HT1080 fibrosarcoma cells (ATCC, Manassas, Va.) were cultured in F12 minimal essential media (Cellgro®, Mediatech, Inc., Herndon, Va.) supplemented with 10% FBS and 1× penicillin/streptomycin. The MCF-7 human mammary carcinoma cell line (ATCC, Rockville, Md.), permanently transformed with a plasmid carrying pro-IGF-II cDNA (obtained from Dr. Daisy De Leon, Loma Linda University, Loma Linda, Calif.) was cultured in DMEM/F12 medium supplemented with 5% FBS and 560 µg/ml of G418 (Life Technologies, Grand Island, N.Y.).

(E) Production and Propagation of Retrovirus to Generate a Light-Emitting Stably Transformed Cell Line.

PT67 packing cells (Clontech, Palo Alto, Calif.) were cultured in DMEM medium supplemented with 10% (v/v) FBS. At 70% confluence, PT67 cells were transformed with pLEIN (Clontech, Palo Alto, Calif.) using calcium phosphate precipitation method (Profection Mammalian Transfection Systems, Promega, Madison, Wis.) for 12 hours. Fresh medium was replenished at this time. Retroviral supernatant collected from PT67 cells 48 hours post transformation was filtered through a 0.45 µm filter and was added to target HT1080 cells along with polybrene to a final concentration of 4 µg/ml. The medium was replaced after 24 hours and the cells were treated with G418 selection at 400 µg/ml and stepwise increased to 1200 µg/ml.

(F) Propagation of Recombinant Vaccinia Virus.

Vaccinia virus Lister strain (LIVP) was used as a wild type virus. Recombinant Vaccinia virus rVV-ruc-gfp was constructed by inserting, via homologous recombination, the ruc-qfp-cassette (Wang et al., Proc. Biolumin. Chemilumin. 9, 1996, 419-422) into the Vaccinia virus genome. The virus was amplified in CV-1 cells by addition of virus particles at a multiplicity of infection (MOI) of 0.1 pfu/cell to CV-1 cell monolayers followed by incubation at 37° C. for 1 h with brief agitation every 10 min. At this time, the supernatant fluid with virus particles was removed, and the cell monolayers were washed once with serum free medium. Complete growth medium was then added and the cells were incubated at 37° C. rVV-ruc-gfp virions propagated in CV-1 cells were purified through a sucrose gradient. A plaque assay was used 72 h after infection to determine the titer of recombinant virus by staining the cells with 50% crystal violet solution in ethanol.

(G) Generation of Mice Carrying Tumor Implants.

Five- to six-week-old male BALB/c athymic nu/nu mice (25-30 g in body weight) and Lewis rats (250-300 g in body weight) were purchased from Harlan (Frederick, Md.). C57BL/6J Min/+ mice were obtained from Jackson Laboratories (Bar Harbor, Me.), Min (multiple intestinal neoplasia) is an autosomal dominant trait involving a nonsense mutation in codon 850 of the murine Apc gene, which renders these animals susceptible to spontaneous intestinal adenoma formation.

To obtain tumors in nude mice, C6 glioma cells were grown, harvested and the cell number was determined by the Trypan Blue exclusion method. Disinfectant was applied to the skin surface, then approximately $5 \times 10^5$ cells were suspended in 100 µl of phosphate buffered saline (PBS) and injected subcutaneously into the right lateral thigh of each mouse. Tumor growth was monitored by recording the size of the tumor with a digital caliper. Tumor volume ($mm^3$) was estimated by the formula $(L \times H \times W)/2$, where L is the length, W is the width, and H is the height of the tumor in mm.

Intracerebral glioma tumors were generated by injecting C6 glioma cells into the head of rats. Prior to injection, rats were anesthetized with sodium pentobarbital (Nembutal® Sodium solution, Abbot Laboratories, North Chicago, Ill.; 60 mg/kg body weight). A midline scalp incision (0.5-1 cm) was made, the skin was retracted, and a 1 mm burr hole was made in the skull at a location 2 mm to the left and 2.5 mm posterior to the brigma. Tumor cells were pipetted into an insulin syringe, which was fitted with a 29-gauge needle and mounted in a stereotactic holder. The needle was inserted vertically through the burr hole to a depth of 3 mm. After injection into the brain of $5 \times 10^5$ C6 cells in a 10 µl volume, the needle was kept in place for 15 sec and then withdrawn. The skin incision was closed with surgical clips. Mice bearing subcutaneous prostate tumors were generated over a period of one month following subcutaneous implantation of $3 \times 10^6$ PC3 human prostate cells.

MB-49 mouse bladder tumor cells were implanted in the C57 mouse bladder to produce animals with bladder tumors. To generate animals with breast cancer (Tian and DeLeon, submitted for publication), female nude mice were first implanted with 0.72 mg/90 day-release 17β-estradiol pellets (Innovative Research, Rockville, Md.) in the skin to facilitate breast tumor development and metastasis. One day after estrogen pellet implantation, $1 \times 10^6$ MCF-7 human breast carcinoma cells transformed with pro-IGF-II (Dull et al., Nature 310 (1984), 777-781) were implanted in the mammary fat pad For orthotopic transplants, tumors developed from implanted cells were resected and minced into 1-$mm^3$ cubes for tissue transplantation into the mammary fat pad.

(H) Assay of *Renilla* luciferase in live animals. Mice were anesthetized with Nembutal® (60 mg/kg body weight) before every *Renilla* luciferase assay. *Renilla* luciferase activities were determined after intravenous injection of a mixture of 5 µl of coelenterazine (0.5 µg/µl diluted ethanol solution) and 95 µl of luciferase assay buffer (0.5 M NaCl; 1 mM EDTA; and 0.1 M potassium phosphate, pH 7.4). Whole live animals were then imaged in a dark box using the Hamamatsu ARGUS 100 low light video camera, and the images were recorded using Image Pro Plus 3.1 software (Media Cybernetics, Silver Spring, Md.). The pseudocolored photon emission image was superimposed onto the gray scale image of the animal in order to precisely locate the site of light emission.

(I) Detection of Luminescence and Fluorescence.

Immediately before imaging, mice and rats were anesthetized with Nembutal® (60 mg/kg body weight). The animals were placed inside the dark box for photon counting and recording superimposed images (ARGUS 100, Hamamatsu, Hamamatsu, Japan). Photon collection was for one minute from ventral and dorsal views of the animals. A light image was then recorded and the low light image was then superimposed over the light image to record the location of luminescent activity.

Imaging of GFP expression in tumors of live animals was performed using a Leica MZ8 stereo fluorescence microscope equipped with a mercury lamp power supply and a GFP filter (excitation at 470 nm). Images were captured using a SONY DKC-5000 3CCD digital photo camera.

(J) Histology of Tumor Tissues.

Under anesthesia, the animals were euthanized with an overdose of Nembutalg. The tissues of interest were removed, embedded in Tissue-Tek OCT compound (Miles Scientific, Naperville, Ill.) and immediately frozen in liquid nitrogen without fixation. Frozen sections were cut at –20° C. using a Reichert-Jung Cryocut 1800 cryostat. GFP fluorescence of the tissues was monitored under a Leica fluorescence microscope and the images were recorded using Photoshop software.

Example 2

Results Obtained by Intravenous Injection of Recombinant Vaccinia Virus rVV-ruc-gfp into Mice (A) Monitoring of Virus-Mediated Marker Gene Expression in Immunodeficient Mice Vaccinia virus ($1 \times 10^8$ pfu) carrying the *Renilla* luciferase—GFP fusion expression cassette (rVV-ruc-gfp) was introduced intravenously into nude mice with no tumors. The animals were observed once every 3 days over a two-week time period under the low-light imager to monitor luciferase catalyzed light emission immediately after intravenous injection of coelenterazine, and under a fluorescence microscope to visualize GFP expression. Neither apparent luminescence nor green fluorescence was detected in the animals when imaged externally, except at certain locations that had small skin lesions. Such luminescence and fluorescence signals disappeared after a few days once the lesions had healed. Animals were sacrificed one week and two weeks after viral infection, and their organs were removed and examined for the presence of luminescence and GFP fluorescence signals. One week after viral injection, no luminescence or green fluorescence could be detected in brain, liver, lung, spleen, kidney or testis. These results indicated that the rVV-ruc-gfp virus did not show organ specificity after injection and that the virus seemed to be cleared from the animal by the immune system soon after systemic delivery via the bloodstream.

(B) Visualization of Vaccinia Virus-Mediated Marker Gene Expression in Glioma Tumors of Live Nude Mice The distribution of injected Vaccinia virus in nude mice bearing subcutaneously implanted C6 glioma tumors was examined. Nude mice with tumors approximately 500 mm$^3$ in size were injected intravenously with $1 \times 10^8$ pfu of the rVV-ruc-gfp virus. Seven days after virus injection, the animals were monitored for GFP expression under a fluorescence microscope to determine the presence of viral infection and multiplication in the tumors, which had grown to approximately 2500 mm$^3$ in size. Surprisingly, green fluorescence was detected only in the tumor regions in live animals. Seven days after viral injection, the GFP fluorescence was very intensely localized in a patch-like pattern restricted to the tumor region (FIG. 1A-A"). These patches, often seen at the end of blood vessel branches, may have indicated local viral infection of tumor cells that surround the leaky terminals of capillary vessels. During real-time observation of the same tumors, the GFP signal from the center of these patches started to disappear, and new green fluorescent centers appeared in the form of rings at the periphery of the fading patches. The new sites of intense GFP fluorescence may have resulted from progression of the viral infection to nearby cells within the tumor during tumor growth and expansion. After careful examination of the mice, with the exception of the tumor region, no detectable green fluorescence was seen elsewhere on the body surface or in the dissected organs. This experiment clearly showed that a mature solid tumor could be easily localized by the labeled Vaccinia virus, based on light-emission, and it also demonstrated the affinity of virus particles for the tumor tissue.

To determine whether tumor size and vascularization are decisive factors for viral retention in tumors, nude mice were intravenously injected with $1 \times 10^8$ rVV-ruc-gfp Vaccinia virus particles one day after subcutaneous C6 cell implantation. Surprisingly, 4 days after viral injection GFP expression was seen in 5-day-old C6 tumors that had a volume of about 25 mm$^3$ (FIG. 1B-B"). Examination of labeled Vaccinia virus tumor targeting by visualization of GFP expression in implanted tumors younger than 5 days was not feasible in live mice, since sufficient levels of marker gene expression required approximately 4 days to allow detection under a fluorescence microscope.

Figure 1:
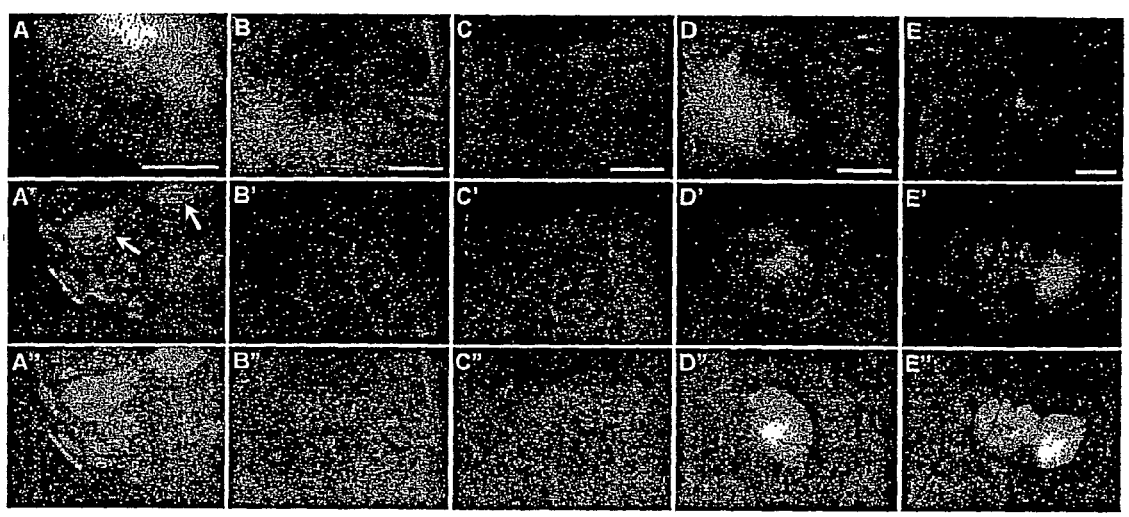
FIG. 1: External imaging of GFP expression in subcutaneous C6 glioma tumors in nude mice C6 glioma cells ($5\times10^5$) were implanted subcutaneously into the right lateral thigh. At designated days after tumor cell implantation, the animals were infected intravenously with $1\times10^8$ pfu of rVV-ruc-gfp virus particles. GFP expression was monitored under a fluorescence stereomicroscope. Bright field (top), fluorescence (middle), and bright field, fluorescence overlay (bottom) images of subcutaneous glioma tumor are shown. GFP signal can be observed in tumors as small as 22 mm$^3$ in size (B-B"), or as old as 18 days (about 2500 mm$^3$ in size) (A-A"). In older tumors, GFP expression was seen in "patch"-like patterns (indicated by arrows in A'). Marker gene expression in the tumor of the same animal can be monitored continuously 4 (C-C"), 7 (D-D"), and 14 (E-E") days after intravenous viral injection. (Bars=5 mm.)
Figure 2:
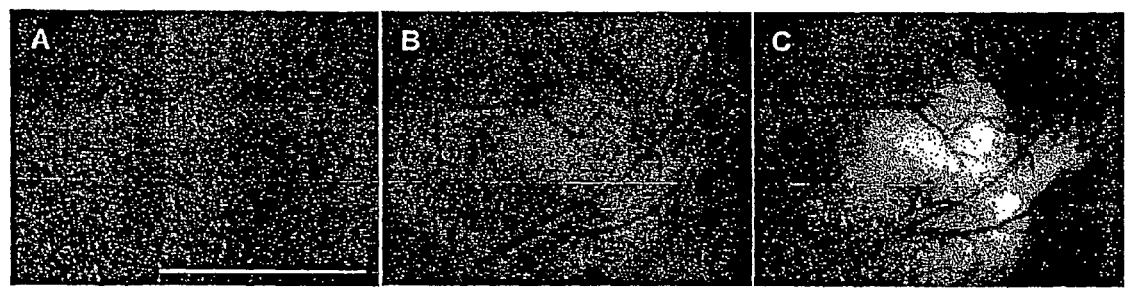
FIG. 2: Visualization of tumor angiogenesis

The finding that injection of the rVV-ruc-gfp Vaccinia virus into the bloodstream of the host resulted in GFP expression and accumulation in tumors suitable for non-invasive tumor detection allowed us to follow the entry and replication process of this virus in the same animal in real time (FIG. 1 C-C", D-D" and E-E"). A continuously increasing level of GFP fluorescence was observed in the same animal throughout 20 days following viral injection, which was the time scheduled before sacrificing the animals. Such an increase in detectable fluorescence was indicative of a very strong viral replication in the tumor tissue, the latter appearing to function as a protective immunoprivileged environment for viral replication. The viral replication in the tumors was verified by determining the viral titer and light emission of the isolated viral particles in cell cultures. Interestingly, the location of blood vessels and the neovascularization within the periphery of the enlarging tumor were readily visible and confirmed by external visualization against a bright green fluorescent background (FIG. 1A-A", D-D", E-E" and FIG. 2).

To determine the location of viral infection within the tumors, the animals were sacrificed and the skin over the tumor was carefully reflected to expose the tumor. In the exposed tumor, GFP fluorescence was found to be concentrated exclusively in the tumor tissue (FIGS. 3B-B" and D-D"). The non-tumorous thigh muscles did not show any fluorescence of viral infection, as indicated by arrows in FIG. 3D-D". The skin overlying the tumor was also non-fluorescent (indicated by asterisks in FIGS. 3B-B" and D-D"). Cross sections of the tumor, however, revealed that strong green fluorescent regions were mostly found as patches in the periphery of the tumor (double arrows in FIG. 3C-C") where the actively dividing tumor cells are presumably located.

To further examine the pattern of viral infection in C6 glioma tumors based on GFP expression, the tumor tissues were sectioned for microscopic analysis under the fluorescence microscope. Comparative analysis of various tissue sections revealed that GFP fluorescence was present in large clusters of cells within the tumor (FIG. 4), but no fluorescence was visible in normal tissues such as the heart, lung, liver, spleen, and kidney.

In addition to GFF, the recombinant rVV-ruc-gfp virus carried a second marker gene, which encoded the *Renilla* luciferase in the form of a fusion protein with GFP. Therefore we were able to directly superimpose the site of GFP fluorescence with light emission from *Renilla* luciferase in the tumors. Immediately after coelenterazine (substrate for *Renilla* luciferase) was delivered by intravenous injection, a very strong luciferase activity was recorded only in the tumor region under a low light video camera (FIG. 5). By lowering the sensitivity of the low light video camera to avoid saturation of light detection, we were able to identify the *Renilla* luciferase gene expression in localized patches in the periphery of the tumor. These patch-like patterns precisely correlated with the GFP signals.

(C) Affinity of Vaccinia Virus Delivered to the Bloodstream for Different Tumors Implanted into Animals To determine whether the attraction of the Vaccinia virus was limited to glioma tumors or whether this attraction could be observed in other tumors, recombinant Vaccinia virus was recombinantly introduced into mice that carried different types of implanted tumors. One of these tumor models was a nude mouse with implanted subcutaneous PC-3 human prostate carcinoma. Although the PC3 implants from which tumors developed grew at a much slower rate than the implanted subcutaneous glioma tumors, these tumors showed the same dynamics with regards to Vaccinia virus infection when identical titers ($1 \times 10^8$) were injected intravenously (FIG. 6A-A"). Similar to our findings with glioia tumors, GFP expression was initially detected 4 days after virus injection, and the fluorescence lasted throughout the 3-week observation period.

Female nude mice with established breast tumors were also used for labeled Vaccinia injections. These breast tumors were allowed to grow for 6 months after the animals received implants of MCF-7 human breast carcinoma cells transformed with pro-IGF-11 cDNA. At the time of Vaccinia virus injection, the tumors had reached maximum growth and the tumor volume (about 400-500 mm$^3$) did not change significantly during the experimental period. Similar to previous experiments, 6 days after intravenous delivery of $1 \times 10^8$ rVVruc-gfp virus particles, strong GFP expression was observed in the breast tumor region (FIG. 6B-B", FIGS. 7A-A" and B-B") and nowhere else in the body.

Examination of cross sections of virus-infected breast tumors revealed luminescent "islands" throughout the tumors without any indication of central or peripheral preference of infection (FIG. 7C-C"). The MCF-7 tumor cells used in these breast tumor models are known to metastasize and in addition to the primary solid tumor, a smaller metastasized tumor found on the left side of the body showed GFP fluorescence (FIG. 7D-D", E-E", and F-F"). Excised lung tissues were also examined for detection of metastases. Metastasized tumors as small as 0.5 mm in diameter on the surface of the lung were positive for GFP fluorescence (FIG. 7G-G"). The presence of a strong *Renilla* luciferase-mediated light emission confirmed the expression of the luciferase-GFP fusion protein in these breast tumors but nowhere else in the body when the substrate coelenterazine was injected intravenously into the live animals. These experiments showed that intravenously delivered Vaccinia virus particles were selectively accumulated to and replicated in primary and metastasized breast tumors in nude mice, likely as a result of the immunocompromised state of the tumor microenvironment.

To determine whether virus particles could move out of tumors and re-enter the circulation, we injected C6 glioma cells into the thigh of mice to form a second tumor in animals already carrying a breast tumor infected with labeled Vaccinia virus. If the virus particles were released from the tumor to re-enter the circulation in significant numbers, they would be able to colonize the newly implanted glioma tumor. Monitoring of these second tumors showed that no GFP signal was visible in the new glioma tumor 7 and 14 days after implantation of the glioma cells. To demonstrate that the newly implanted glioma tumors could be targeted by labeled Vaccinia virus, a second dose of rVV-ruc-gfp virus ($1\times10^8$ pfu) was intravenously injected. Five days later, tumor-specific GFP expression was detected in the newly formed glioma tumor in addition to GFP expression seen in the original breast tumor. These findings suggested that the virus particles in infected tumors were either not released back into the circulation at all, or were not released in sufficient numbers to infect and replicate in a second tumor.

Two additional tumor models, including Lewis rats with intracranial C6 rat glioma tumors and C57 mice with ME-49 mouse bladder tumors in the bladder, were used for Vaccinia injections. To determine whether tumor-affinity of virus particles is a phenomenon limited to tumors in nude mice with a diminished T-lymphocyte function or whether it is a general protective property of tumors that may be demonstrated also in immunocompetent animals, Lewis rats with intracranial C6 rat glioma tumors and C57 mice with MB-49 mouse bladder tumors in the bladder were used. A total of $5\times10^5$ C6 glioma cells in a 100 µl volume were stereotactically implanted in the brains of 2 of 4 immunocompetent Lewis rats, and the tumors were allowed to grow for 5 days. The other 2 rats were injected intracranially with phosphate-buffered saline to serve as controls. On day six, all 4 rats were intravenously injected with rVV-ruc-gfp virus particles via the femoral vein. Five days after virus injection, all 4 animals were sacrificed, and their brains were carefully excised for analysis by fluorescence microscopy. GFP expression was detected in the brains with implanted intracranial tumors (FIG. 6C-C") while no GFP expression was seen in the control brains. In parallel experiments, C57 mice, with or without bladder tumors, were divided into two groups. One group was injected intravenously with rVV-ruc-gfp Vaccinia virus ($1\times10^8$ pfu) and the other with saline solution as control. Five days after virus injection, the animals were sacrificed and examined under the fluorescence microscope GFP expression was observed in the bladder tumor region in C 57 mice but not in control mice (FIG. 6D-D").

Taken together, these experiments show that Vaccinia virus particles were selectively accumulated and retained in a variety of tumors, probably protected by the tumor microenvironment, and that they were not able to survive in the non-tumorous tissues of immunocompromised as well as immunocompetent animals. The tumor-targeting process by intravenously injected Vaccinia virus carrying the light-emitting dual marker gene demonstrated the ability of the Vaccinia virus system to detect primary and metastatic tumors in live animals.

Example 3

Results of Intravenous Injection of Bacterial and Mammalian Light-Emitting Cells into Mice (A) Visualization of Light Emitting Bacteria present in Whole Animals after Intravenous Injection To determine the fate of intravenously injected luminescent bacteria in the animals, $10^7$ bacteria carrying the pLITE201 plasmid in 50 µl were injected into the left femoral vein of mice under anesthesia. Following closure of the incision with sutures, the mice were monitored under the low light imager (ARGUS 100 Camera System, Hamamatsu, Hamamatsu, Japan) in real time and photons were collected for one minute. The imaging was repeated in two-day time intervals to determine the presence of light emission from a given animal. It was found that the distribution pattern of light emission following an intravenous injection of bacteria into mice was characteristic of the bacterial strains used. Injection of the attenuated *V. cholera* into the bloodstream resulted in light emission localized in the liver immediately. Injection of *S. typhimurium*, however, was widely disseminated throughout the body of the animal suggesting a difference in the interaction with host cell system (FIG. 8A-8D). Imaging the same animals 24 and 48 hours post-infection showed that all of the detectable light emission from the earlier time diminished rapidly and was eliminated completely from the injected animal. These findings suggest that light emitting bacteria injected into the bloodstream via the femoral vein are cleared. This process was confirmed by photon emission analysis of excised organs, which were found to lack light emission. Similar data were obtained in immunocompetent mice and rats suggesting that the removal of bacteria from the blood is efficient in both systems.

(B) Bacteria Home in to Glioma Tumors in Nude Mice

To determine if bacteria preferentially colonize tumorous tissues, nude mice with ten-day-old tumors (about 500 mm$^3$) in the right hind leg were injected intravenously via the femoral vein with $10^7$ *S. typhimurium* or $10^7$ *V. cholera* in a 50 µl volume of bacterial suspension. Following injection, the incision wounds were sutured and the animals were monitored for six days under the low light imager. At each observation time point, photons were collected for exactly one minute. In mice injected with *S. typhimurium*, luminescent bacteria were disseminated throughout the whole body of the animal similar to the findings in the non-tumorous mice (FIG. 9A). Nude mice injected with *V. cholera*, demonstrated luminescent activity only in the liver region during the early observation period (FIG. 9E). Regardless of the bacterial strain injected, two days after injection, luminescent activity was observed only in the tumor region (FIGS. 9B and 9F). Monitoring of the mice under the low light imager on days four and six post-injection showed decreased amounts of detectable luminescence in the tumors of animals injected with *S. typhimurium* (FIGS. 9C and 9D). This finding was in marked contrast with the findings in the tumors of mice injected with *V. cholera*, which demonstrated not only survival but also propagation of the bacteria in the tumor mass with a dramatic increase in light emission (FIGS. 9G and 9H).

Nude mice bearing subcutaneous human PC3 prostate tumors in the right hind leg were intravenously injected with $10^7$ attenuated *L. monocytogenes* transformed with pS0D-gfp plasmid DNA carrying the gfp cDNA. GFP fluorescence was observed under a fluorescence stereomicroscope. Twenty-seven hours after bacterial injection, GFP signal was detected only in the tumor region (FIG. 14). No GFP signal was observed in the rest of the animal.

(C) Determination of Minimum Size and Age of Glioma Tumors Necessary for Bacterial Infection The purpose of this experiment was to determine whether the size of the tumor has any influence on its ability to be colonized by bacteria. Tumors were induced in the right hind leg of nude mice by subcutaneous injection of glioma cells as described. On days 0, 2, 4, 6, 8, and 10 of tumor induction, attenuated *S. typhimurium* and *V. cholera* with the pLITE201 plasmid were injected intravenously through the femoral vein. Presence of luminescent bacteria in the tumor was determined by photon collection for exactly one minute under the low light imager two and four days post-infection. The tumor volume was also determined by measuring the dimensions with a digital caliper. The earliest time-point when luminescent activity was noted in the tumors was on day eight after tumor induction. Corresponding tumor volumes were approximately 200 mm$^3$.

(D) Bacteria Home in to Breast Tumors of Nude Mice

In order to determine whether colonization of tumors is limited to glioma cells or whether this is a general phenomenon observed with all tumors, female nude mice bearing tumors in the right breast pad were intravenously injected with $10^7$ *V. cholera* in a 50 µl volume of bacterial suspension. The animals were monitored within the first 10 minutes after inoculation under the low light imager for one minute and demonstrated the typical luminescent pattern in the liver region (FIG. 10A). Two days later, while the liver had become clear of luminescent bacteria, the breast tumor was colonized by the labeled *V. cholera*. In addition to the main tumor, a metastatic tumor in the left breast demonstrated luminescent activity (FIG. 10B). On day five, the animals had cleared the bacteria that colonized the incision wound, however, the tumors remained luminescent (FIG. 10C). FIG. 10D shows the continued colonization and propagation of the bacteria in the main tumor, while the metastatic, smaller tumor had become cleared. Luminescent activity continued for over 45 days in the right breast tumor. Similar experiments were conducted using *E. coli* to demonstrate that homing in of tumors by bacteria is not strain dependent (FIGS. 10E and 10F).

To determine whether the bacteria from the tumor enter the blood circulation in significant quantities to colonize other sites, a second tumor (C6 glioma) was induced in these animals in the right hind leg. The tumor was allowed to grow for 10 days. No luminescent activity was observed in the glioma tumor demonstrating the absence of a significant bacteria that would cause colonization of this tumor. However, when the animal was rechallenged with $10^7$ attenuated *V. cholera* intravenously, the leg tumor showed strong luminescent activity.

The findings of these experiments demonstrate that larger tumors retain bacteria more effectively over time. Furthermore, the bacteria within the tumors do not escape into the blood in sufficient quantities to infect susceptible sites such as other tumors.

(E) Bacteria Home in to Bladder Tumors in Immunocompetent Mice

C57 mice were intravenously injected with $10^7$ attenuated *V. cholera* transformed with pLITE201 encoding the lux operon. On day nine after bacterial delivery, luminescent activity was recorded by photon collection for one minute under the low light imager. Light emission was noted in the bladder region of the whole animal (FIG. 11A). The animals were sacrificed and an abdominal incision was made to expose the bladder. Luminescent activity was positively confirmed to be limited to the bladder (FIG. 11B). Upon removal of the bladder from the mice, luminescent activity was no longer visible anywhere in the animals, however, the excised bladders continued to demonstrate light emission (FIG. 11C). Based on the results of this experiment, bacteria can target tumors in immunocompetent as well as nude mice. Furthermore, the bacteria can also target smaller tumors.

(F) Bacteria Home in to Glioma Tumors in the Brain of Rats

Lewis rats with glioma tumors in the brain were intravenously injected with $10^8$ attenuated *V. cholera* with the pLITE201 plasmid through the left femoral vein to determine if bacteria can cross the blood-brain barrier and target tumors in immunocompetent animals. The whole animals were monitored for one minute under the low light imager the following day and low levels of luminescent activity was observed through the skull. The rats were sacrificed and the brain tissue was removed in one piece in order to further evaluate the exact location of the luminescent bacteria. Visualization of the excised brain under the imager demonstrated strong luminescent activity in specific regions of the brain (FIG. 12A). Similar imaging of control rats without brains tumors, which were intravenously injected with the labeled bacteria, demonstrated absence of any luminescent activity (FIG. 12B).

(G) Transformed Human Fibrosarcoma Cells Home in to Subcutaneous Glioma Tumors in Nude Mice Nude mice with subcutaneous glioma tumors were injected intravenously with $5 \times 10^5$ human fibrosarcoma cells, which were permanently transformed with retrovirus derived from pLEIN. Seven days post-injection, the animals were anesthetized Nembutal®, and monitored under a fluorescent stereomicroscope. Fluorescent cells were noted only in the tumor region of the whole mice through the skin (FIG. 13A1-3). Upon exposure of the tumor tissues by reflection of the overlying skin (FIG. 13B1-3), and in cross sections of the tumors (FIG. 13C1-3), fluorescent patches were visible in distinct regions. Close examination of the organs of the mice showed the presence of small clusters of fluorescent cells in the lungs of the animals, demonstrating the affinity of the fibrosarcoma cells for the lungs in addition to the tumorous tissue.

Example 4

Construction of Bacterial Plasmid Vectors that Carry the Light-Emitting Protein Encoding Expression Cassettes and the Therapeutic Gene Expression Constructs in cis Configuration (A) Rationale Using the light-emitting expression systems described above, tumors could be imaged based on light emission for up to 45 days in animals. These findings suggest a remarkable plasmid DNA stability in bacteria in the absence of selection. Therefore, by placing the therapeutic gene cassette in cis configuration with the light-emitting protein expression cassette on the same replicon, light emission can be used as an indicator of therapeutic construct presence and stability. In contrast to light-emitting proteins, the therapeutic proteins, endostatin and *Pseudomonas* exotoxin/TGF alpha fusion protein, are required to be secreted from the bacteria into the medium or into the cytosol of tumor cells for inhibition of tumor growth. To achieve protein secretion from the extracellularly replicating *E. coli* cells into the tumor, two constructs with different signal sequences can be designed. For secretion of endostatin, the ompF signal sequence can be placed upstream of the coding sequence of endostatin, which facilitates the secretion into the periplasmic space. To release the endostatin into the medium, an additional protein, the PAS protein, needs to be coexpressed with endostatin. PAS has been shown to cause membrane leakiness and the release of secreted proteins into the medium (Tokugawa et al., J. Biotechnol. 37 (1994), 33; Tokugawa et al., J. Biotechnol. 35 (1994), 69). The second construct for the secretion of *Pseudomonas* exotoxin/TGF alpha fusion protein from *E. coli* has the OmpA signal sequence upstream of the fusion gene and the release from the periplasmic space into the medium is facilitated by sequences present in domain II of the exotoxin (Chaudhary et al. PNAS 85 (1988), 2939; Kondo et al., J. Biol. Chem. 263 (1988), 9470; Kihara and Pastan, Bioconj. Chem. 5 (1994), 532). To promote secretion of endostatin and *Pseudomonas* exotoxin/TGF alpha fusion protein from *L. monocytogenes*, the signal sequence of listeriolysin (LLO) (Mengaud et al., Infect. Immun. 56 (1988), 766) can be placed upstream of each coding sequence.

For regulation of endostatin and *Pseudomonas* exotoxin/TGF alpha fusion protein expression levels in bacteria, vectors can be generated where the therapeutic protein encoding genes are under the control of the T7 promoter or the $P_{spac}$ synthetic promoter (Freitag and Jacobs, Infect. Immun. 67 (1999), 1844). Without exogenous induction, the levels of the therapeutic proteins are low in *E. coli* and in *L. monocytogenes*. The minimal levels of therapeutic proteins in bacteria provide greater safety following intravenous injection of the engineered bacteria. In the following, the construction of six plasmid DNAs for constitutive and regulated expression of endostatin and *Pseudomonas* exotoxin/TGF alpha fusion protein in *E. coli* and *L. monocytogenes* is described. All plasmids to be transferred into *E. coli* will carry the constitutively expressed bacterial lux operon, and all the plasmids to be transferred into *L. monocytogenes* will carry the constitutively expressed sod-gfp cassette. Plasmids BSPT#1-ESi and BSPT#2-Pti are able to replicate in *E. coli* only, and plasmids BSPT*3, #4, #5, and #6 replicate in *E. Coli* and *L. monocytogenes*, (B) Construction of Plasmid Vectors for Protein Expression and Secretion from *E. coli*

The construction of the endostatin secretion vector to be used in *E. coli* is as follows. The coding sequence of human endostatin (591 bp) will be amplified by PCR from the plasmid pES3 with the introduction of the required restriction sites on both ends, followed by ligation into a pBluescript (Clontech Corp., USA) cloning vector to generate pBlue-ES. The ompF signal sequence (Nagahari et al., EMBO J. 4 (1985), 3589) is amplified with Taq polymerase and inserted upstream in frame with the endostatin sequence to generate pBlue-ompF/ES. The expression cassette driven by the T7 promoter will be excised, and inserted into the pLITE201 vector described in Example 1(B), above, carrying the lux-CDABE cassette, to produce the plasmid pLITE-ompF/ES. The sequence encoding the PAS factor (a 76 amino acid polypeptide) will be amplified from the chromosomal DNA of *Vibrio alginolyticus* (formerly named *Achromobacter iophagus*) (NCIB 11038) with Taq polymerase using the primers 5'-GGGAAAGACATGAAACGCTTA3-' and 5'-AAACAACGAGTGAATTAGCGCT-3', and inserted into the multiple cloning sites of pCR-Blunt (Clontech Corp., USA) to create the expression cassette under the control of the lac promoter. The resulting plasmid will be named pCR-PAS. The lac promoter linked to the pas gene will be excised from pCR-PAS and inserted into pLITEompF/ES to yield the final plasmid BSPT#1-ESI.

Plasmid pVC85 (Kondo et al., 1998, J. Biol. Chem. 263: 9470-9475) contains a T7 promoter, followed by an ompA signal sequence, and a sequence encoding domain II and III of *Pseudomonas* exotoxin (PE40). The DNA sequence encoding PE40 will be excised with restriction enzymes and replaced with a fragment of PE37/TGF alpha (*Pseudomonas* exotoxin A 280-613/TGF alpha) obtained from the plasmid CT4 (Kihara & Pastan, 1994, Bioconjug. Chem. 5: 532-538) to create the plasmid pVC85-PE37/TGF alpha. The expression cassette of ompAPE37/TGF alpha linked to the T7 promoter will be excised and inserted into pLITE201 to yield the final plasmid BSPT#2-PTI.

(C) Construction of Plasmid Vectors for Protein Expression and Secretion from *L. monocytogenes*

Genes encoding endostatin or PE37/TGF alpha will be inserted downstream of the listeriolysin (LLO) signal sequence in the plasmid pCHHI to generate pCHHI-ES and pCCHI-PE37/TGF alpha. Constitutive expression of the therapeutic proteins will be obtained by linking the above secretion cassettes to the listeriolysin promoter obtained from the pCHHI vector. The sod-gfp expression cassette, excised from the plasmid psod-gfp (Geötz et al. PNAS in press.) will be inserted into pCHHI-ES to generate BSPT#3-ESc, and into pCCHI-PE37/TGF alpha to generate BSPT#4-PTc. For the expression of the therapeutic proteins under the control of an IPTG inducible promoter, the listeriolysin promoter in BSPT#3-ESc and BSPT#4-PTc will be replaced with the $P_{spac}$ promoter from the plasmid pSPAC (Yansura and Henner, PNAS USA 81 (1984), 439) to generate BSPT#5-ESi and BSPT#6-PTi. $P_{spac}$ is a hybrid promoter consisting of the *Bacillus subtilis* bacteriophage SPO-1 promoter and the lac operator. IPTG-induced GFP expression from the $P_{spac}$ promoter has been documented in *L. monocytogenes* in the cytosol of mammalian cells.

Example 5

Demonstration of the Expression of Luciferase and GFP in Bacteria and Verification of the Secretion of Endostatin and Recombinant Toxin/TGF Alpha Fusion Protein and their Function in Cell Culture Assays To be able to detect the presence of *E. coli* and *L. monocytogenes* in tumor tissues in live animals, the levels of the constitutively expressed luciferase and GFP in bacteria need to be adequate. Therefore, after transformation of recipient *E. coli* or *L. monocytogenes* with the constructs described in Example 4, the colonies with the highest luciferase light emission or GFP fluorescence will be selected. In addition to characterizing light emission from each selected colony before intravenous injection, the ability of the selected transformants to secret endostatin and *Pseudomonas* exotoxin/TGF alpha fusion protein into the medium needs to be confirmed. The presence of endostatin and *Pseudomonas* exotoxin/TGF alpha fusion protein synthesized within *E. coli* and *L. monocytogenes* will be determined by extracting these proteins from the cell pellet. The secreted proteins in the medium will be concentrated and analyzed by gel separation and the quantity will be determined by Western blotting. It is imperative to determine the percentage of the newly synthesized proteins expressed from each plasmid construct in either *E. coli* or *L. monocytogenes* that is present in the medium. It is also essential to confirm, in addition to constitutive expression of endostatin and *Pseudomonas* exotoxin/TGF alpha fusion protein, that expression can be induced in *E. coli* and in *L. monocytogenes* upon the addition of IPTG to the bacterial, culture medium. For the design of future tumor therapy protocols, the relative amounts of protein secreted by the constitutive expression system needs to be compared to the induced expression levels for a defined time period first in bacterial cultures. It is equally essential to determine that both proteins when synthesized in *E. coli* and *L. monocytogenes* are biologically active if generated from the proposed constructs. Both proteins were synthesized previously in *E. coli* and were shown to be active.

The results of the experiments described below should confirm whether endostatin is successfully secreted from *E. coli* using the OmpF signal peptide in combination with PAS pore forming protein expression. These experiments will also show if the PE40/TGF alpha and PE37/TGF alpha fusion proteins are secreted from bacteria using the OmpA signal peptide in combination with domain II of PE. Further, the listeriolysin signal peptide may also facilitate the secretion of endostatin and the chimeric toxin/TGF alpha fusion protein into the medium as well as into the cytosol of infected tumor cells. Using the endothelial cell migration inhibition assay and the protein synthesis inhibition assay, it can be expected to determine that both proteins secreted into the medium are biologically active. The presence and quantities of these proteins may be regulated by replacing the constitutive promoters with promoters that can be induced by IPTG.

In addition to the secretion system described below, alternative secretion systems such as the *E. coli* HlyBD-dependent secretion pathway (Schlor et al., Mol. Gen. Genet. 256 (1997), 306), may be useful. Alternative secretion signals from other gram positive bacteria, such as the *Bacillus* sp. endoxylanase signal peptide (Choi et al., Appl. Microbiol. Biotechnol. 53 (20001, 640; Jeong and Lee, Biotechnol. Bioeng. 67 (2000), 398) can be introduced.

(A) Confirmation of Endostatin and *Pseudomonas* exotoxin/TGF Alpha Fusion Protein Secretion from Bacteria into Growth Medium

*E. coli* strains (DH5α and BL21(λDE3) will be transformed with BSPT#1-ESi and BSPT#2-PTi plasmid DNA. *L. monocytogenes* strain EGDA2 will be transformed with plasmids BSPT#3-ESc, BSPT#4-PTc, BSPT#5-ESi, and BSPT#6-PTi individually. After plating on appropriate antibiotic-containing plates, individual colonies will be selected from each transformation mixture. These colonies will be screened under a low light imager and fluorescence microscope for luciferase and GFP expression, respectively. Three colonies with the most intense light emission from each transformation batch will be chosen for further studies. To verify the secretion of endostatin and *Pseudomas* exotoxin/TGF alpha fusion protein from each selected transformant, the cells will be grown in minimal medium to log phase. After centrifuging down the bacteria, the supernatants will be passed through a 0.45-µm-pore-size filter, and the bacterium-free medium will be used for precipitation of the secreted proteins. The precipitates will be collected by centrifugation. Pellets will be washed, dried, and re-suspended in sample buffer for protein gel separation. Proteins from aliquots corresponding to 10 µl of bacterial culture will be compared to proteins from 200 µl of culture supernatant after separation in a 10% SDS-polyacrylamide gel. Western blot analysis will be performed using polyclonal antibody against endostatin (following the antibody production protocol described by Timpl, Methods Enzymol. 82 (1982), 472) and monoclonal antibody against TGF alpha (Oncogene Research Products, Cambridge, Mass., USA). The optimal growth conditions will be established for secretion by sampling the growth medium at different times during growth. A similar method has been used previously to analyze secreted proteins in *Salmonella typhimurium* culture supernatant (Kaniga et al., J. Bacteriol. 177 (1995), 0.3965). By use of these methods, the amount of secreted proteins in the bacterial culture medium generated by each of the constructs without induction will be established. To estimate the increase in the amount of secreted proteins in the medium, IPTG-dependent promoter activation experiments will be carried out by adding IPTG to the bacterial culture in log phase for 3 to 6 hours, and the secreted proteins will be assayed as above.

(B) Verification of the Biological Activity of Endostatin Secreted by *E. coli* and *L. Monocytogenes* Using a Migration Inhibition Assay It has been shown that endostatin inhibits vascular endothelial growth factor (VEGF)-induced human umbilical vein endothelial cell (HUVEC) migration. Thus, the biological activity of endostatin secreted by bacteria can be tested using the HUVEC migration assay provided by Cascade Biologics, Portland, Oreg. The inhibition of cell migration will be assessed in 48-well chemotaxis chambers (Neuro Probe, Gaithersburg, Md.) (Polyerine et al., Methods Enzymol. 198 (1991), 440). Bacterium-free supernatant from each secretion construct will be added to HUVECs for preincubation for 30 min. After incubation, the HUVECs will be placed in the upper chamber. The migration of HUVECs into the lower chamber induced by $VEGF_{165}$ (R&D Systems, Minneapolis, Minn.) will be quantified by microscopic analysis. The concentration of functional endostatin in the medium will be directly proportional to the degree of inhibition of HUVEC migration.

(C) Testing the Cytotoxic Activity of Secreted Recombinant PE Toxin in Tumor Cell Cultures The inhibitory activity of the chimeric toxin in mammalian cells will be measured based on inhibition of de novo protein synthesis by inactivating EF-2 (Carroll and Collier, J. Biol. Chem. 262 (1987), 8707). Aliquots of bacterium-free supernatants obtained from the expression of various recombinant PE secretion constructs in *E. coli* and in *L. monocytogenes* will be added to the C6 glioma cells or to HCTI 16 colon carcinoma cells. Following treatment with medium, the mammalian cells will be pulsed with [$^3$H]-leucine, and the incorporation will be determined in the protein fraction. To determine the presence of secreted chimeric toxin proteins in *L. monocytogenes*-infected mammalian cells, the bacteria will be eliminated from the medium by gentamicin treatment. The mammalian cells containing *L. monocytogenes* in the cytosol will be lysed, and the released bacteria removed from the lysate by filtration. The mammalian cell lysate containing the secreted chimeric toxins will be assayed in protein synthesis inhibition experiments. The inhibition of [$^3$H]-leucine incorporation in tumor cell culture will be directly proportional to the amount of the biologically active chimeric toxin protein in the medium and cell lysate.

Example 6

Determination of the Entry, Localization and Distribution of Intravenously Injected Bacteria in Tumors of Live Animals (A) Rationale Since only a small number of intravenously injected bacteria escape the immune system by entering the tumor, their immediate localization is not possible due to limited light emission in live animals. Their location can only be verified by sectioning the tumor to identify the early centers of light emission. Looking at sections at a later time point, bacteria can be seen throughout the entire tumor due to rapid replication. To determine whether one or multiple bacteria enter through the same site, red fluorescent protein can be used to label the extracellularly replicating *E. coli* and green fluorescent protein for the intracellularly replicating *L. monocytogenes*. By visualizing the distribution of the red and green fluorescence in tissue sections, the entry sites as well as replication and localization of *E. coli* and *L. monocytogenes* can be determined individually and simultaneously in the central or peripheral regions of the tumor. It can be expected that the patterns of entry and distribution obtained in implanted tumors mimic those of spontaneous tumors, accordingly, the bacterium-based diagnosis and protein therapy will become a valid approach.

With the experiments described in section (B), below, the entry, replication, and distribution of light-emitting bacteria in spontaneous tumors can be compared to the distribution patterns in implanted tumors. Further, double-labeling experiments will allow the operator to precisely locate the extracellularly replicating *E. coli* and the intracellularly replicating *L. monocytogenes* in the same tumor sections. Lastly, it can be determined (subsequent to a five-day bacterial colonization) whether bacteria are distributed evenly in the tumors or preferential localization occurs in the periphery of the tumor or in the necrotic center. A possible reduction in bacterial entry into spontaneously occurring tumors due to the immunocompetence of these animals can be overcome by increasing the number of intravenously injected bacteria.

(B) Intravenous Injection of *E. coli* Expressing Red Fluorescent Protein and *L. monocytogenes* Expressing Green Fluorescent Protein into Nude Mice and into Rodents with Implanted and Spontaneous Tumors

*E. coli* (DH5α) carrying the DsRed (Matz et al., Nat. Biotech. 17 (1999), 969) expression cassette under the control of a constitutive promoter are used in this experiment, *L. monocytogenes* EGD strain derivatives with in-frame deletion in each of the virulence genes were individually labeled with the green fluorescent protein cassette driven by the constitutive SOD promoter.

The localization and intratumoral distribution of bacteria will first be studied in nude mice with implanted C6 glioma or HCT116 colon carcinoma tumors. C6 glioma or HCT116 colon carcinoma cells ($5\times10^5$ in 100 μl) will be subcutaneously injected into the right hind leg of the animals. Twelve days after tumor cell injection, the animals will be anesthetized, and the left femoral vein surgically exposed. Light-emitting bacteria ($1\times10^6$ cells re-suspended in 50 μl of saline) will be intravenously injected, and the wound incision will be closed with sutures. Tumors will be measured three times a week using a caliper. Tumor volume will be calculated as follows: small diameter×large diameter×height/2.

The localization of bacteria in the tumor, based on GEP or RFP, will also be analyzed using cryosectioned tumor tissues. A reliable morphological and histological preservation, and reproducible GFP or RFP detection may be obtained using frozen sections after a slow tissue freezing protocol (Shariatmadari et al., Biotechniques 30 (2001), 1282). Briefly, tumor tissues will be removed from the sacrificed animals to a Petri dish containing PBS and dissected into the desired size. The samples will be mixed for 2 h in 4% paraformaldehyde (PFA) in PBS at room temperature. They will be washed once with PBS, and embedded in Tissue-Tek at room temperature, and then kept in the dark at 4° C. for 24 h and slowly frozen at −70° C. Before sectioning, the tissue will be kept at −20° C. for 30 min. Then, 10- to 50-μm-thick sections will be cut with a Reichert-Jung Cryocut 1800 cryostat and collected on poly-L-lysine (1%)-treated microscope slides. During sectioning, the material will be kept at room temperature to avoid several freezing and thawing cycles. Finally, the sections will be rinsed in PBS and mounted in PBS and kept in the dark at 4° C.

To monitor the entry of light emitting *E. coli* and *L. monocytogenes* from the blood stream into the tumor, 27 nude mice will be injected with C6 tumor cells, and 27 nude mice with HCT116 colon carcinoma cells. Twelve days after tumor development, 9 animals from the C6 group and 9 from the HCT116 group will receive an intravenous injection of *E. coli* with the RFP construct. Another 9 animals from each group will receive an intravenous injection of *L. monocytogenes* transformed with the GFP cDNA construct. The third group of 9 animals from each tumor model will receive both *E. coli* and *L. monocytogenes* ($1\times10^6$ cells of each). Five hours, 25 hours, and 5 days after injection, three animals of each treatment group will be sacrificed, their tumors excised, and processed individually as described in the above cryosectioning protocol. After freezing, each tumor will be cut into two halves. One half of the tumor will be used for preparing thick sections (60-75 μm), which will be analyzed under a fluorescence stereomicroscope to observe the distribution of bacteria in the sections of tumors obtained from each time point of the experiment. The regions of interest will be identified, thin sectioned, prepared, and analyzed with laser scanning cytometry and under the confocal microscope followed by image reconstruction.

In parallel experiments, animals with spontaneous tumors, as listed in Table 6, will be obtained and used in intravenous injection experiments with *E. coli* carrying the bacterial lux operon. Two animals of each tumor model will be used, and the luciferase light emission monitored daily under the low light imager. It is expected that the spontaneously occurring tumors can be imaged similarly to the implanted tumors based on bacterial luciferase expression. Two of the spontaneous tumor models, mice with adenocarcinoma of the large intestine and mice with adenocarcinoma of the mammary tissue, will be used for bacterial localization experiments following intravenous injection of *E. coli* expressing RFP and *L. monocytogenes* expressing GFP as described above. It can be expected that these experiments will emphasize the significance of the bacterium-based diagnosis and protein therapy system.

TABLE 6

Spontaneous tumor animal models

| Animal species | Strain name | Tumor description | Source | Reference |
|---|---|---|---|---|
| Mouse | 129/Sv-Madh3$^{mlpar}$ | Spontaneous adenocarcinoma of large intestine | Jackson Laboratories Bar Harbor, ME | Zhu et al., Cell 94 (1988), 703 |
| Mouse | FVB/N-TgN(UPII-SV40T)29Xrw | Spontaneous carcinoma of bladder with metastasis to the liver | Jackson Laboratories Bar Harbor, ME | Zhang et al., Cancer Res. 59 (1999), 3512 |
| Mouse | FVB-neuN(N#202) | Spontaneous adenocarcinoma of mammary tissue | Jackson Laboratories Bar Harbor, ME | Guy et al., PNAS USA 89 (1992), 10578 |
| Rat | F344/CrCrlBR | Spontaneous carcinoma of pituitary | Charles River Laboratories, Wilmington, MA | Hosokawa et al., Toxicol.Pat hol. 21 (1993), 283 |

Example 7

Verification of Bacterium-Mediated Tumor Targeting and Bacterium-Secreted Protein Therapy in Rodents with Implanted or Spontaneous Tumors (A) Rationale As shown in the previous examples, intravenous injection of light-emitting bacteria results in entry, replication, and accumulation only in the tumor regions in animals. This process can be monitored by imaging of light emission in tumors. Placing the endostatin and chimeric toxin expressing gene cassettes in cis configuration with a light-emitting gene cassette provides an indirect detection system in vivo for their temporal and spacial delivery via bacteria The endostatin and chimeric toxin gene cassettes are linked to signal peptide encoding sequences, which facilitate the secretion of these proteins into the extracellular space in the tumor or into the cytosol of infected tumor cells. Both proteins secreted from bacteria into the extracellular space of the tumor are expected to function similarly to directly injected purified proteins. Both proteins secreted from *L. monocytogenes* into the cytosol of the infected tumor cells will resemble the viral delivery system reported earlier for endostatin. The bacterial systems can be used as a constitutive secretion system or as an exogenously added IPTG-activatable secretion system in the tumor. By regulating the expression levels of the therapeutic proteins in bacteria that colonize the tumor, the secreted amount of proteins inhibiting tumor growth can be determined. Without the addition of IPTG, the inhibitory protein secretion from the intravenously injected bacteria will be kept at minimum while in blood circulation. This will provide added safety to the recipient tumorous animals during delivery of bacteria. Using the BSPT system, the onset and duration of the therapy can be controlled by the addition of IPTG. Upon completion of the treatment, the bacterial delivery system can be eliminated by administration of antibiotics, similar to treating a bacterial infection.

(B) Determination of the Effect Of endostatin and *Pseudomonas* exotoxin/TGF Alpha Fusion Protein Secreted by *E. coli* and *L. monocytogenes* on Tumor Growth in Animals with Implanted Tumors The inhibitory effect of endostatin and the cytotoxicity of the chimeric toxin secreted by *E. coli* and *L. monocytogenes* in tumors will be determined as follows. Thirty five nude mice bearing 10-day-old C6 tumors will be injected with bacterial constructs as follows: (a) Five mice with *E. coli* engineered to secrete endostatin; (b) Five mice with *E. coli* engineered to secrete chimeric toxin; (c) Five mice with *L. monocytogenes* engineered to secrete endostatin; (d) Five mice with *L. monocytogenes* engineered to secrete chimeric toxin; (e) Five mice with *E. coli* secreting endostatin and chimeric toxin; (f) control group: five mice injected with *E. coli* expressing bacterial luciferase alone, and five mice with *L. monocytogenes* expressing GFP. At the time of bacteria injection, each tumor volume will be determined. Three days after injection, the replication of bacteria in the tumors will be monitored under a low light imager or under a fluorescence stereomicroscope. The light emission and the tumor volume will be measured daily up to 20 days after bacterial injection. Ten days after injection, one animal from each group will be sacrificed and the levels of the secreted proteins present in the tumor tissue will be analyzed using Western blot analysis. These experiments will result in inhibition of tumor growth in endostatin treated animals or a more dramatic tumor regression in animals treated with chimeric toxin proteins. The tumor growth in control animals is not expected to be affected by the bacteria alone.

In a follow-up experiment, mice with spontaneous adenocarcinoma of mammary tissue (strain FVB-neuN(N#202), Table 6) will be used to study the effect of secreted proteins on tumor growth. An experimental scheme identical to that described for the C6 tumor analysis will be used. At the completion of tumor therapy, the presence of endostatin or chimeric toxin in the tumor tissue will be determined by Western blot analysis. An identical experimental design will be used to assay the effect of IPTG-induction of endostatin and chimeric toxin production in bacteria in C6 tumors as well as in the spontaneously occurring breast tumor mouse model. It is expected that multiple IPTG induction of protein expression in bacteria might be required for successful tumor therapy.

At any stage of tumor treatment, it may be required to remove the light emitting and therapeutic gene containing bacteria from the animal. To carry out this experiment, mice with 12-day-old C6 tumors will be intravenously injected with *E. coli* expressing the bacterial luciferase. Three days after injection, antibiotic therapy will be initiated by intraperitoneal administration of gentamicin (5 mg/kg body weight) twice daily, or the newly discovered clinafloxacin (CL960) (Nichterlein et al., Zentralbl. Bakteriol. 286 (1997), 401) This treatment will be performed for 5 days, and the effect of antibiotics on the bacteria will be monitored by imaging light emission from the animals daily.

By completing the above experiments, it is expected that endostatin and chimeric toxin proteins secreted into the tumors will cause the inhibition of tumor growth and measurable tumor regression. It is anticipated that tumor regression will be achieved in both groups of rodents with implanted tumors and with spontaneously occurring tumors. Experiments with simultaneous application of secreted endostatin and chimeric toxin proteins in tumor treatment may give the most promising results. The removal of the engineered bacteria from the tumor by administration of antibiotics is an added safety measure of the bacterium-secreted protein therapy (BSPT) of the present invention.

The invention claimed is:

1. A method for imaging, monitoring or detecting a tumor in a tumor-bearing subject, the method comprising:
    intravenously administering a composition comprising a vaccinia virus that is a Lister strain variant from the Institute of Viral Preparations (LIVP) to a tumor-bearing subject, wherein the LIVP virus encodes a detectable protein or a protein that induces a detectable signal; and
    imaging, monitoring or detecting the detectable protein or signal following accumulation of the LIVP vaccinia virus in tumor cells of the subject.

2. The method of claim 1, wherein the virus contains DNA encoding a protein or proteins for tumor therapy and/or elimination of metastatic tumors.

3. The method of claim 1, wherein:
    the virus comprises DNA encoding a protein that induces a detectable signal; and
    the signal is one or both of luminescence and fluorescence.

4. The method of claim 2, wherein the protein for therapy or the protein for detection, imaging or monitoring is a cell receptor that binds to a ligand.

5. The method of claim 4, wherein the method further comprises administering to the subject a ligand that binds to the receptor and that is a radionuclide-labelled ligand.

6. The method of claim 4, wherein the method further comprises administering to the subject a ligand that binds to the receptor and that is a paramagnetic- or superparamagnetic-metal-labelled ligand.

7. The method of claim 4, wherein the method further comprises administering to the subject a ligand that binds to the receptor and that is coupled to a toxin.

8. The method of claim 4, wherein the method further comprises administering to the subject a ligand that binds to the receptor and that is coupled to a therapeutic protein.

9. The method of claim 8, wherein the ligand is an antibody.

10. The method of claim 1, wherein the virus encodes a protein that induces a signal detectable by magnetic resonance imaging (MRI) or binds to a contrasting agent, chromophore or to a ligand required for visualization of tissues.

11. The method of claim 3, wherein the protein that induces a detectable signal is a luciferase, red fluorescent protein or green fluorescent protein.

12. The method of claim 11, wherein the virus encodes a protein for the production of substrate for the luciferase.

13. The method of any one of claims 1-10, 11, and 12, wherein tumor detection, imaging or monitoring is carried out by MRI.

14. The method of claim 1, wherein the method further comprises administering to the subject:
    (a) an antimicrobial compound fused to a protein for tumor therapy and/or elimination of metastatic tumors; and/or
    (b) an antimicrobial compound fused to a detectable protein or a protein that induces a detectable signal.

15. The method of claim 2, wherein the protein for tumor therapy and/or elimination of metastatic tumors is endostatin or recombinant chimeric toxin PE37/transforming growth factor alpha (TGF-alpha).

16. The method of claim 2, wherein the protein for tumor therapy and/or elimination of metastatic tumors is a protein that converts a nontoxic prodrug into a toxic drug that is cytotoxic to a tumor.

17. The method of claim 1, wherein said tumor is a bladder tumor, breast tumor, prostate tumor, glioma, tumor, liver tumor, skin tumor, colon tumor, lung tumor, ovarian carcinoma or pancreatic carcinoma.

* * * * *

UNITED STATES PATENT AND TRADEMARK OFFICE
CERTIFICATE OF CORRECTION

Page 1 of 2

PATENT NO. : 8,642,257 B2
APPLICATION NO. : 10/485179
DATED : February 4, 2014
INVENTOR(S) : Szalay et al.

It is certified that error appears in the above-identified patent and that said Letters Patent is hereby corrected as shown below:

IN THE TITLE PAGES:

In Item (56) References Cited, at page 1, column II, line 40, please replace "Kim et al" with —Kirn et al—;

at page 9, column II, line 70, please replace "/?-galactosidase" with —β-galactosidase—;

at page 12, column I, line 67, please replace "[Article in Italian]" with —[Article in Turkish]—;

at page 15, column II, line 65, please replace "[Article in Italian]" with —[Article in Turkish]—;

at page 16, column II, line 70, please replace "D. H. Kim" with —D. H. Kirn—;

at page 18, column I, line 28, please replace "Kim et al." with —Kirn et al.—.

IN THE SPECIFICATION:

At column 4, line 2, please replace "section 61" with —section 6.1—;

at column 4, line 5, please replace "*Vibrio harvoyi*" with —*Vibrio harveyi*—;

at column 4, line 48, please replace "$^{64}$CU" with —$^{64}$Cu—;

at column 4, line 50, please replace "$^{60}$Cu(I)" with —$^{60}$Cu(II)—;

at column 5, line 35, please replace "pancreatictumors" with —pancreatic tumors—;

at column 8, line 36, please replace "*Bacillus meqatherium*" with —*Bacillus megatherium*—;

at column 13, lines 59-60, please replace "*Bifidobacterium* longum" with —*Bifidobacterium longum*—;

at column 19, line 31, please replace "(1992)" with —(1982)—;

at column 31, line 42, please replace "tutor tissues" with —tumor tissues—;

at column 33, line 18, please replace "EGYR" with —EGFR—;

Signed and Sealed this
Twenty-second Day of July, 2014

Michelle K. Lee
*Deputy Director of the United States Patent and Trademark Office*

CERTIFICATE OF CORRECTION (continued)
U.S. Pat. No. 8,642,257 B2 at column 34, line 49, please replace "gluctronyl" with —glucuronyl—;

at column 37, line 8, please replace "*B. coli*" with —*E. coli*—;

at column 37, line 65, please replace "*Listeria* monocytogene" with —*Listeria monocytogenes*—;

at column 38, line 17, please replace "M001" with —M010—;

at column 40, line 34, please replace "Nembutalg" with —Nembutal®—;

at column 42, line 25, please replace "GFF" with —GFP—;

at column 42, line 53, please replace "glioia" with —glioma—;

at column 43, line 44, please replace "ME-49" with —MB-49—;

at column 45, line 14, please replace "pS0D-gfp" with —psod-gfp—;

at column 48, line 2, please replace "BSPT*3" with —BSPT#3—;

at column 48, line 2, please replace "*E. Coli*" with —*E. coli*—;

at column 48, line 51, please replace "Geötz" with —Götz—;

at column 50, line 1, please replace "(20001" with —(2000)—;

at column 50, line 38, please replace "177 (1993), 0.3965" with —177 (1993), 3965—;

at column 50, line 56, please replace "Polyerine" with —Polverini—;

at column 52, line 29, please replace "GEP" with —GFP—.

UNITED STATES PATENT AND TRADEMARK OFFICE
CERTIFICATE OF CORRECTION

| | |
|---|---|
| PATENT NO. | : 8,642,257 B2 |
| APPLICATION NO. | : 10/485179 |
| DATED | : February 4, 2014 |
| INVENTOR(S) | : Szalay et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 359 days.

Signed and Sealed this
Twenty-ninth Day of December, 2015

Michelle K. Lee
*Director of the United States Patent and Trademark Office*